US009611305B2

(12) United States Patent
Ikeda et al.

(10) Patent No.: US 9,611,305 B2
(45) Date of Patent: Apr. 4, 2017

(54) TREATING CARDIOVASCULAR OR RENAL DISEASES

(71) Applicant: Mayo Foundation for Medical Education and Research, Rochester, MN (US)

(72) Inventors: Yasuhiro Ikeda, Rochester, MN (US); Stephen James Russell, Rochester, MN (US); Alessandro Cataliotti, Rochester, MN (US); John C. Burnett, Jr., Rochester, MN (US); Jason M. Tonne, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/370,554

(22) PCT Filed: Jan. 4, 2013

(86) PCT No.: PCT/US2013/020392
§ 371 (c)(1),
(2) Date: Jul. 3, 2014

(87) PCT Pub. No.: WO2013/103896
PCT Pub. Date: Jul. 11, 2013

(65) Prior Publication Data
US 2015/0005371 A1    Jan. 1, 2015

Related U.S. Application Data

(60) Provisional application No. 61/584,006, filed on Jan. 6, 2012.

(51) Int. Cl.
| C07K 14/47 | (2006.01) |
| C07K 14/58 | (2006.01) |
| C12N 15/86 | (2006.01) |
| C12N 7/00 | (2006.01) |

(52) U.S. Cl.
CPC .......... *C07K 14/4705* (2013.01); *C07K 14/58* (2013.01); *C12N 7/00* (2013.01); *C12N 15/86* (2013.01); *C07K 2319/02* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| 3,842,067 A | 10/1974 | Sarantakis |
| 3,862,925 A | 1/1975 | Sarantakis et al. |
| 3,972,859 A | 8/1976 | Fujino et al. |
| 4,034,074 A | 7/1977 | Miles |
| 4,051,842 A | 10/1977 | Hazel et al. |
| 4,098,876 A | 7/1978 | Piasio et al. |
| 4,105,602 A | 8/1978 | Colescott et al. |
| 4,140,122 A | 2/1979 | Kuhl et al. |
| 4,161,521 A | 7/1979 | Veber et al. |
| 4,233,402 A | 11/1980 | Maggio et al. |
| 4,383,529 A | 5/1983 | Webster |
| 4,496,544 A | 1/1985 | Needleman |
| 4,683,195 A | 7/1987 | Mullis et al. |
| 4,728,721 A | 3/1988 | Yamamoto et al. |
| 4,749,688 A | 6/1988 | Haslanger et al. |
| 4,757,048 A | 7/1988 | Lewicki et al. |
| 4,804,650 A | 2/1989 | Lewicki et al. |
| 4,935,492 A | 6/1990 | Lewicki et al. |
| 4,938,763 A | 7/1990 | Dunn et al. |
| 4,996,143 A | 2/1991 | Heller et al. |
| 5,047,397 A | 9/1991 | Scarborough et al. |
| 5,114,923 A | 5/1992 | Seilhamer et al. |
| 5,202,239 A | 4/1993 | Tarnowski et al. |
| 5,212,286 A | 5/1993 | Lewicki et al. |
| 5,226,325 A | 7/1993 | Komurasaki et al. |
| 5,278,201 A | 1/1994 | Dunn et al. |
| 5,278,202 A | 1/1994 | Dunn et al. |
| 5,296,347 A | 3/1994 | LaMotte, III |
| 5,322,930 A | 6/1994 | Tarnowski et al. |
| 5,410,016 A | 4/1995 | Hubbell et al. |
| 5,434,133 A | 7/1995 | Tanaka et al. |
| 5,449,662 A | 9/1995 | Scarborough |
| 5,449,751 A | 9/1995 | Forssmann et al. |
| 5,501,863 A | 3/1996 | Rossling et al. |
| 5,529,914 A | 6/1996 | Hubbell et al. |

(Continued)

FOREIGN PATENT DOCUMENTS

| EP | 0045665 | 9/1985 |
| EP | 0497368 | 8/1992 |

(Continued)

OTHER PUBLICATIONS

US 6,884,780, 04/2005, Drummond et al. (withdrawn)
Cataliotti et al.; Long-Term Cardiac pro-B-Type Natriuretic Peptide Gene Delivery Prevents the Development of Hypertensive Heart Disease in Spontaneously Hypertensive Rats; Circulation; vol. 123; pp. 1297-1305; published online Mar. 14, 2011.*
Tonne et al.; AAV9-Mediated proBNP Delivery Improves Diastolic Performance in a Model of Spontaneous Hypertensive Rats; Molecular Therapy; vol. 18, Supplement 1, Abstract 599; pp. S232-S233; May 2010.*

(Continued)

*Primary Examiner* — Antonio Galisteo Gonzalez
(74) *Attorney, Agent, or Firm* — Fish & Richardson P.C.

(57) ABSTRACT

This document provides methods and materials for treating cardiovascular and/or renal diseases. For example, AAV9 vectors designed to express natriuretic polypeptides, nucleic acid molecules encoding natriuretic polypeptides, methods for making AAV9 vectors, and methods for using such vectors or molecules to treat cardiovascular and/or renal diseases are provided.

2 Claims, 14 Drawing Sheets

(56) References Cited

U.S. PATENT DOCUMENTS

| | | |
|---|---|---|
| 5,560,922 A | 10/1996 | Chien et al. |
| 5,565,322 A | 10/1996 | Heller |
| 5,580,859 A | 12/1996 | Felgner et al. |
| 5,583,108 A | 12/1996 | Wei et al. |
| 5,589,466 A | 12/1996 | Felgner et al. |
| 5,665,704 A | 9/1997 | Lowe et al. |
| 5,674,710 A | 10/1997 | Seilhamer et al. |
| 5,691,310 A | 11/1997 | Vesely |
| 5,698,213 A | 12/1997 | Jamiolkowski et al. |
| 5,767,239 A | 6/1998 | Immer et al. |
| 5,846,932 A | 12/1998 | Lowe et al. |
| 5,848,956 A | 12/1998 | Grettner |
| 5,849,489 A | 12/1998 | Heller |
| 5,948,761 A | 9/1999 | Seilhamer et al. |
| 6,013,630 A | 1/2000 | Shimkets |
| 6,124,430 A | 9/2000 | Mischak et al. |
| 6,162,603 A | 12/2000 | Heller |
| 6,162,902 A | 12/2000 | Mischak et al. |
| 6,165,458 A | 12/2000 | Foldvari et al. |
| 6,312,679 B1 | 11/2001 | Tomalia et al. |
| 6,376,207 B1 | 4/2002 | Mischak et al. |
| 6,407,211 B1 | 6/2002 | Burnett et al. |
| 6,410,044 B1 | 6/2002 | Chudzik et al. |
| 6,551,795 B1 | 4/2003 | Rubenfield et al. |
| 6,586,396 B1 | 7/2003 | Seilhamer et al. |
| 6,613,332 B1 | 9/2003 | Michael et al. |
| 6,812,339 B1 | 11/2004 | Venter et al. |
| 6,818,619 B2 | 11/2004 | Burnett et al. |
| 6,828,107 B2 | 12/2004 | Asada et al. |
| 6,833,447 B1 | 12/2004 | Goldman et al. |
| 6,849,714 B1 | 2/2005 | Bridon et al. |
| 6,887,470 B1 | 5/2005 | Bridon et al. |
| 6,887,481 B1 | 5/2005 | Chan et al. |
| 6,897,030 B2 | 5/2005 | Seilhamer et al. |
| 6,974,861 B2 | 12/2005 | Seilhamer et al. |
| 7,022,673 B2 | 4/2006 | Drummond et al. |
| 7,026,293 B2 | 4/2006 | Kitakaze |
| 7,179,790 B2 | 2/2007 | Seilhamer et al. |
| 7,214,786 B2 | 5/2007 | Kovalic et al. |
| 7,276,481 B2 | 10/2007 | Golembo et al. |
| 7,332,569 B2 | 2/2008 | Cojocaru et al. |
| 7,345,142 B2 | 3/2008 | Cohen et al. |
| 7,384,917 B2 | 6/2008 | Burnett et al. |
| 7,754,852 B2 | 7/2010 | Burnett, Jr. et al. |
| 7,795,221 B2 | 9/2010 | Sharma et al. |
| 7,803,901 B2 | 9/2010 | Burnett, Jr. et al. |
| 7,964,564 B2 | 6/2011 | Burnett, Jr. et al. |
| 8,063,191 B2 | 11/2011 | Burnett, Jr. et al. |
| 8,076,288 B2 | 12/2011 | Levy et al. |
| 8,283,318 B2 | 10/2012 | Chen et al. |
| 8,324,162 B2 | 12/2012 | Simari et al. |
| 8,354,496 B2 | 1/2013 | Pan et al. |
| 8,357,656 B2 | 1/2013 | Simari et al. |
| 8,455,438 B2 | 6/2013 | Burnett, Jr. et al. |
| 8,530,422 B2 | 9/2013 | Chen et al. |
| 8,642,550 B2 | 2/2014 | Dickey et al. |
| 8,741,842 B2 | 6/2014 | Burnett, Jr. et al. |
| 8,835,601 B2 | 9/2014 | Chen et al. |
| 8,912,137 B2 | 12/2014 | Pan et al. |
| 2002/0082219 A1 | 6/2002 | Burnett et al. |
| 2004/0086976 A1 | 5/2004 | Fleer et al. |
| 2004/0123343 A1 | 6/2004 | Rosa et al. |
| 2005/0059600 A1 | 3/2005 | Burnett, Jr. et al. |
| 2006/0019890 A1 | 1/2006 | Kapoun et al. |
| 2006/0025367 A1 | 2/2006 | Simari |
| 2006/0172933 A1 | 8/2006 | James et al. |
| 2006/0183154 A1 | 8/2006 | Shih et al. |
| 2006/0293232 A1 | 12/2006 | Levy et al. |
| 2007/0042957 A1 | 2/2007 | Burnett, Jr. et al. |
| 2007/0281887 A1 | 12/2007 | Pan |
| 2008/0032933 A1 | 2/2008 | Burnett, Jr. et al. |
| 2009/0022729 A1 | 1/2009 | Mackman et al. |
| 2009/0054337 A1 | 2/2009 | Burnett et al. |
| 2009/0069243 A1 | 3/2009 | Burnett et al. |
| 2010/0041612 A1 | 2/2010 | Beinborn |
| 2010/0048468 A1 | 2/2010 | Gegg et al. |
| 2010/0204094 A1 | 8/2010 | Simari et al. |
| 2010/0266704 A1 | 10/2010 | Ahlheim et al. |
| 2010/0317600 A1 | 12/2010 | Immer et al. |
| 2011/0053787 A1 | 3/2011 | Brulliard et al. |
| 2011/0152191 A1 | 6/2011 | Burnett, Jr. et al. |
| 2011/0152194 A1 | 6/2011 | Burnett, Jr. et al. |
| 2011/0223230 A1 | 9/2011 | Hersel et al. |
| 2011/0236353 A1 | 9/2011 | Wilson et al. |
| 2011/0269684 A1 | 11/2011 | Burnett, Jr. et al. |
| 2011/0282030 A1 | 11/2011 | Dickey et al. |
| 2012/0010142 A1 | 1/2012 | Burnett, Jr. et al. |
| 2012/0053123 A1 | 3/2012 | Burnett, Jr. et al. |
| 2012/0108514 A1 | 5/2012 | Burnett, Jr. et al. |
| 2012/0277155 A1 | 11/2012 | VanAntwerp et al. |
| 2013/0143816 A1 | 6/2013 | Pan et al. |
| 2013/0143820 A1 | 6/2013 | Simari et al. |
| 2013/0281375 A1 | 10/2013 | Burnett, Jr. et al. |
| 2013/0296241 A1 | 11/2013 | Chen et al. |
| 2013/0303454 A1 | 11/2013 | Burnett, Jr. et al. |
| 2014/0005358 A1 | 1/2014 | Lee et al. |
| 2014/0066367 A1 | 3/2014 | Chen et al. |
| 2014/0179605 A1 | 6/2014 | Chen et al. |
| 2014/0228294 A1 | 8/2014 | Burnett, Jr. et al. |
| 2014/0274901 A1 | 9/2014 | Ichiki et al. |
| 2014/0357561 A1 | 12/2014 | Chen et al. |

FOREIGN PATENT DOCUMENTS

| | | |
|---|---|---|
| EP | 0533084 | 3/1993 |
| EP | 1743653 | 1/2007 |
| EP | 2292779 | 3/2011 |
| EP | 2292780 | 3/2011 |
| EP | 2298926 | 3/2011 |
| EP | 2345731 | 7/2011 |
| JP | 06-009688 | 1/1994 |
| JP | 10-500969 | 1/1998 |
| JP | 10-152445 | 6/1998 |
| WO | WO 8403285 | 8/1984 |
| WO | WO 8403825 | 10/1984 |
| WO | WO 8909611 | 10/1989 |
| WO | WO 9302556 | 2/1993 |
| WO | WO 9316687 | 9/1993 |
| WO | WO 9524419 | 9/1995 |
| WO | WO 9820165 | 5/1998 |
| WO | WO 9845329 | 10/1998 |
| WO | WO 9912576 | 3/1999 |
| WO | WO 9957318 | 11/1999 |
| WO | WO 0071576 | 11/2000 |
| WO | WO 0144284 | 6/2001 |
| WO | WO 0224895 | 3/2002 |
| WO | WO 03052052 | 6/2003 |
| WO | WO 2004047871 | 6/2004 |
| WO | WO 2004071736 | 8/2004 |
| WO | WO 2005000095 | 1/2005 |
| WO | WO 2005072055 | 8/2005 |
| WO | WO 2006017852 | 2/2006 |
| WO | WO 2006086769 | 8/2006 |
| WO | WO 2006110743 | 10/2006 |
| WO | WO 2007022123 | 2/2007 |
| WO | WO 2007034498 | 3/2007 |
| WO | WO 2007035600 | 3/2007 |
| WO | WO 2008061355 | 5/2008 |
| WO | WO 2008089532 | 7/2008 |
| WO | WO 2009086126 | 7/2009 |
| WO | WO 2012058585 | 5/2012 |
| WO | WO 2014127120 | 8/2014 |

OTHER PUBLICATIONS

Lee, Abstract PT-08 "Design, synthesis, and in vivo pharmacologic actions of a novel peptide integrating human c-type natriuretic peptide, urodilatin, and b-type natriuretic peptide," Clinical Pharmacology & Therapeutics, vol. 85, Suppl, p. S3, 1 page, Feb. 2009.

Lula et al., "Study of angiotensin-(1-7) vasoactive peptide and its beta-cyclodextrin inclusion complexes: complete sequence-specific NMR assignments and structural studies," Peptides, 28:2199-2210, Epub Aug. 19, 2007.

(56) References Cited

OTHER PUBLICATIONS

ClinicalTrials.gov [online] NCT00475852, "A Study Testing the Effectiveness of Nesiritide in Patients With Acute Decompensated Heart Failure." Retrieved from the Internet: <URL: https://clinicaltrials.gov/ct2/show/NCT00475852?term=Acute+Study+of+C>, 4 pages, May 18, 2007.
Hernandez et al., "Acute Study of Clinical Effectiveness of Nesiritide in Decompensated Heart Failure Trial (ASCEND-HF)," Circulation, 122:2217 Abstract 21828, 1 page, 2010.
Medscape [online] "ASCEND-HF: Nesiritide Safe But of Limited Dyspnea Benefit in Acute HF." Retrieved from the Internet: <URL: http://www.medscape.com/viewarticle/732501>, 4 pages, Nov. 14, 2010.
U.S. Appl. No. 60/605,300, filed Aug. 27, 2004, Burnett.
U.S. Appl. No. 61/116,024, filed Nov. 19, 2008, Burnett, Jr. et al.
Abbey and Potter, "Vasopressin-dependent inhibition of the C-type natriuretic peptide receptor, NPR-B/GC-B, requires elevated intracellular calcium concentrations," *J Biol Chem.*, 277(45):42423-42430, Epub Aug. 23, 2002.
Abdallah et al., "Mechanism of cGMP-mediated protection in a cellular model of myocardial reperfusion injury," *Cardiovasc Res.*, 66(1):123-131, Apr. 1, 2005.
Abdallah et al., "Non-viral gene transfer: applications in developmental biology and gene therapy," *Biol Cell.*, 85(1):1-7, 1995.
Abdelhafiz, "Heart failure in older people: causes, diagnosis and treatment," *Age Ageing.*, 31(1):29-36, Jan. 2002.
Agullo et al., "Effect of ischemia on soluble and particulate guanylyl cyclase-mediated cGMP synthesis in cardiomyocytes," *Am J Physiol Heart Circ Physiol.*, 284(6):H2170-H2176, Epub Feb. 13, 2003.
Ahluwalia et al., "Vascular actions of natriuretic peptides. Cyclic GMP-dependent and -independent mechanisms," *Basic Res Cardiol.*, 99(2):83-89. Epub Jan. 23, 2004.
Allen and O'Connor, "Management of acute decompensated heart failure," *Can Med Assoc J.*, 176(6):797-805, Mar. 13, 2007.
Anand-Srivastava, "Natriuretic peptide receptor-C signaling and regulation," Peptides, 26(6):1044-1059, Epub Apr. 8, 2005.
Anyadike et al., "Brain natriuretic peptide reverses the effects of myocardial stunning in rabbit myocardium," *Pharmacology.* 80(1):40-48, Epub May 21, 2007.
Arora et al., "Atrial natriuretic peptide is negatively regulated by microRNA-425," *J Clin Invest.*, 123(8):3378-3382, Epub Jul. 15, 2013.
Atlas and Laragh, "Physiological Actions of Atrial Natriuretic Factor," Atrial Hormones and Other Natriuretic Factors, Mulrow et al., (eds.), *Am. Physiol. Soc.*, Bethesda, MD, pp. 53-76, 1987.
Averill et al., "Cardiac angiotensin-(1-7) in ischemic cardiomyopathy," *Circulation*, 108(17):2141-2146. Epub Sep. 29, 2003.
Baldini et al., "Atrial natriuretic factor inhibits mitogen-induced growth in aortic smooth muscle cells," *J Cell Physiol.*, 193:103-109, Oct. 2002.
Banga, "Theme section: transdermal delivery of proteins," *Pharm. Res.*, 24(7):1357-1359, Jul. 2007.
Barber, "Atrial natriuretic peptide preserves endothelial function during intimal hyperplasia," *J Vasc Res.*, 42:101-110, Mar.-Apr. 2005, Epub Jan. 19, 2005.
Batlle et al., "New aspects of the renin-angiotensin system: angiotensin-converting enzyme 2—a potential target for treatment of hypertension and diabetic nephropathy," *Curr Opin Nephrol Hypertens.*, 17(3):250-257, May 2008.
Baxter, "Natriuretic peptides and myocardial ischaemia," *Basic Res Cardiol.*, Mar. 2004; 99(2):90-93, Epub Jan. 23, 2004.
Benter et al., "Angiotensin-(1-7) prevents diabetes-induced cardiovascular dysfunction," *Am J Physiol Heart Circ Physiol.*, 292(1):H666-H672, Jan. 2007.
Bergijk et al., "A histologic study of the extracellular matrix during the development of glomerulosclerosis in murine chronic graft-versus-host disease," *Am J Pathol.*, 140(5):1147-1156, May 1992.

Best et al., "Dendroaspis natriuretic peptide relaxes isolated human arteries and veins," *Cardiovasc Res.*, 55(2):375-384, Aug. 1, 2002.
Bestle et al., "Cardiovascular, endocrine, and renal effects of urodilatin in normal humans," *Am J Physiol.*, 276(3 Pt 2):R684-R695, Mar. 1999.
Bloch et al., "A serum protease cleaves proANF into a 14-kilodalton peptide and ANF," *Am J Physiol.*, 252(1 Pt 1):E147-E151, Jan. 1987.
Boerrigter and Burnett, Jr., "Cardiorenal syndrome in decompensated heart failure: prognostic and therapeutic implications," *Curr Heart Fail Rep.*, 1(3):113-120, Sep. 2004.
Boerrigter et al., "Abstract 3478: Evidence for Differential Modulation of the Cardiorenal Actions of B-Type Natriuretic Peptide by the Peptidases Dipeptidyl Peptidase IV and Meprin A," *Circulation*, 118:S_432, 2008.
Boerrigter et al., "Targeting heme-oxidized soluble guanylate cyclase in experimental heart failure," *Hypertension*, 49(5):1128-1133. Epub Feb. 26, 2007.
Braunwald, "Shattuck lecture—cardiovascular medicine at the turn of the millennium: triumphs, concerns, and opportunities," *N Engl J Med.*, 337(19):1360-1369, Nov. 6, 1997.
Brenner et al., "Diverse biological actions of atrial natriuretic peptide," *Physiol Rev.*, 70(3):665-699, Jul. 1990.
Brosnihan et al., "Angiotensin-(1-7) dilates canine coronary arteries through kinins and nitric oxide," *Hypertension*, 27(3 Pt 2):523-528, Mar. 1996.
Brosnihan et al., "Angiotensin-(1-7): a novel vasodilator of the coronary circulation," *Biol Res.*, 31(3):227-234, 1998.
Brosnihan, "Effect of the angiotensin-(1-7) peptide on nitric oxide release," *Am J Cardiol.*, 82(10A):17S-19S, Nov. 19, 1998.
Bruneau et al., "BNP gene expression is specifically modulated by stretch and ET-1 in a new model of isolated rat atria," *Am. J. Physiol.*, 273:H2678-H2686, 1997.
Bryan and Potter, "The atrial natriuretic peptide receptor (NPR-A/GC-A) is dephosphorylated by distinct microcystin-sensitive and magnesium-dependent protein phosphatases," *J. Biol. Chem.*, 277:16041-16047, 2002.
Bryan et al., "Renal hyporesponsiveness to atrial natriuretic peptide in congestive heart failure results from reduced atrial natriuretic peptide receptor concentrations," *Am J Physiol Renal Physiol.*, 292(5):F1636-F1644, Epub Jan. 30, 2007.
Burchill et al., "Acute kidney injury in the rat causes cardiac remodelling and increases angiotensin-converting enzyme 2 expression," *Exp Physiol.*, 93(5):622-630. Epub Jan. 25, 2008.
Burger and Burger, "BNP in decompensated heart failure: heart failure: Diagnostic, prognostic and therapeutic potential," *Curr. Opin. Investig. Drugs*, 2(7):929-935, 2001.
Burley and Baxter, "B-type natriuretic peptide limits reperfusion injury via opening of ATP-sensitive potassium channels," *J Mol Cell Cardiol.*, 40(6):967-968, Jun. 2006.
Burley et al., "Cardioprotective actions of peptide hormones in myocardial ischemia," *Heart Fail Rev.*, 12(3-4):279-291, Dec. 2007.
Burley et al., "Cyclic GMP and protein kinase-G in myocardial ischaemia-reperfusion: opportunities and obstacles for survival signaling," *Br J Pharmacol.*, 152(6):855-869. Epub Aug. 13, 2007.
Burnett, Jr., et al., "Alterations in the kidney in heart failure: the cardiorenal axis in the regulation of sodium homeostasis," *Heart failure: a companion to Braunwald's heart disease.* Elsevier Inc, Philadelphia (2004): 279-289.
Burnett, Jr., et al., "Atrial natriuretic peptide elevation in congestive heart failure in the human," *Science*, 231(4742):1145-1147, Mar. 7, 1986.
Burnett, Jr., et al., "Effects of synthetic atrial natriuretic factor on renal function and renin release," *Am. J. Physiol.*, 247(5 Pt 2):F863-F866, Nov. 1984.
Butkowski et al., "Basement membrane collagen in the kidney: regional localization of novel chains related to collagen IV," *Kidney Int.*, 35(5):1195-1202, May 1989.
Cameron and Ellmers, "Minireview: natriuretic peptides during development of the fetal heart and circulation," *Endocrinology*, 144(6):2191-2194, Jun. 2003.

(56) References Cited

OTHER PUBLICATIONS

Canaan-Kuhl et al., "C-type natriuretic peptide inhibits mesangial cell proliferation and matrix accumulation in vivo," *Kidney Int.*, 53(5):1143-1151, May 1998.

Canaan-Kühl et al., "Identification of "B" receptor for natriuretic peptide in human kidney," *Endocrinology.*, 130(1):550-552, Jan. 1992.

Cannone et al., "A genetic variant of the atrial natriuretic peptide gene is associated with cardiometabolic protection in the general community," *J Am Coll Cardiol.*, 58(6):629-636, Aug. 2, 2011.

Cannone et al., "The atrial natriuretic peptide genetic variant rs5068 is associated with a favorable cardiometabolic phenotype in a Mediterranean population," *Diabetes Care.*, 36(9):2850-2856, Epub May 1, 2013.

Carstens et al., "Metabolism and action of urodilatin infusion in healthy volunteers," *Clin Pharmacol Ther.*, 64(1):73-86, Jul. 1998.

Cataliotti et al., "Abstract 6278: Burden of Chronic Renal Insufficiency in the General Population and Added Predictive Power of GFR to BNP and NT-proBNP in Detection of Altered Ventricular Structure and Function," *Circulation*, 118:S_1173, 2008.

Cataliotti et al., "Brain natriuretic peptide enhances renal actions of furosemide and suppresses furosemide-induced aldosterone activation in experimental heart failure," *Circulation*, 109:1680-1685, 2004.

Cataliotti et al., "Chronic actions of a novel oral B-type natriuretic peptide conjugate in normal dogs and acute actions in angiontensin II mediated hypertension," *Circulation*, 118:1729-1736, Epub Oct. 6, 2008.

Cataliotti et al., "CNP production in the kidney and effects of protein intake restriction in nephrotic syndrome," *Am J Physiol Renal Physiol.*, 283(3):F464-F472, Sep. 2002.

Cataliotti et al., "Long-term cardiac pro-B-type natriuretic peptide gene delivery prevents the development of hypertensive heart disease in spontaneously hypertensive rats," *Circulation.*, 123(12):1297-1305, Epub Mar. 14, 2011.

Cataliotti et al., "Oral brain natriuretic peptide: a novel strategy for chronic protein therapy for cardiovascular disease," *Trends Cardiovasc Med.*, 17(1):10-14, Jan. 2007.

Cavero et al., "Cardiorenal Actions of Neutral Endopeptidase Inhibition in Experimental Congestive Heart Failure," *Circulation*, 82:196-201, 1990.

Chan et al., "Phosphodiesterase v inhibition has favorable effects on LV remodeling and potentiates the renal actions of subcutaneously administered BNP without adverse hemodynamic effects in experimental overt congestive heart failure," *Circulation*, 110(17)(Suppl. S):22, Meeting Info.: 77th Scientific Meeting of the American-Heart-Association, Oct. 26, 2004.

Chappell et al., "Pathways of angiotensin-(1-7) metabolism in the kidney," *Nephrol Dial Transplant.*, 16 Suppl 1:22-26, 2001.

Chappell, "Emerging evidence for a functional angiotension-converting enxyme 2-angiotension-(1-7)-MAS receptor axis: more than regulation of blood pressure?" *Hypertension.*, 50(4):596-599, Epub Sep. 4, 2007.

Chauhan et al., "Release of C-type natriuretic peptide accounts for the biological activity of endothelium-derived hyperpolarizing factor," *Proc Natl Acad Sci U S A.*, 100(3):1426-1431, Epub Jan. 27, 2003.

Chaumet-Riffaud et al., "Altered PGE2 and PGF2 alpha production by glomeruli and papilla of sodium-depleted and sodium-loaded rats," *Am. J. Physiol.*, 241:F517-F524, 1981.

Chen and Burnett, Jr., "Clinical application of the natriuretic peptides in heart failure," *European Heart Journal Supplements* (2006) 8 (Supplement E), E18-E25.

Chen and Burnett, Jr., "The natriuretic peptides in heart failure: diagnostic and therapeutic potentials," *Proc Assoc Am Physicians.*, 111(5):406-416, Sep.-Oct. 1999.

Chen et al., "Abstract 1412: A novel designer natriuretic and diuretic peptide based upon an alternatively spliced BNP without vascular vasodilatory actions," *Circulation*, 114(18):270, 2006.

Chen et al., "Abstract 1481: Renal Targeted Protein Therapeutics in Experimental Overt Heart Failure With Renal Dysfunction," *Circulation*, 118:S_334, 2008.

Chen et al., "Equimolar doses of atrial and brain natriuretic peptides and urodilatin have differential renal actions in overt experimental heart failure," *Am. J. Physiol. Regul. Integr. Comp. Physiol.*, 288(5):R1093-1097, print May 2005, epub Dec. 2004.

Chen et al., "KCNQ1 Gain-of-function mutation in familial atrial fibrillation," *Science*, 299:251-254, Jan. 2003.

Chen et al., "Local renal delivery of a natriuretic peptide a renal-enhancing strategy for B-type natriuretic peptide in overt experimental heart failure," *J Am Coll Cardiol.*, 53(15):1302-1308, Apr. 14, 2009.

Chen et al., "Low dose nesiritide and the preservation of renal function in patients with renal dysfunction undergoing cardiopulmonary-bypass surgery: a double-blind placebo-controlled pilot study," *Circulation.*, 116(11 Suppl):I134-I138, Sep. 11, 2007.

Chen et al., "Maximizing the Renal Cyclic 3'-5'-Guanosine Monophosphate System with Type 5 Phosphodiesterase Inhibition and Exogenous Natriuretic Peptide: A Novel Strategy to Improve Renal Function in Experimental Overt Heart Failure," *J. Am. Soc. Nephrology*, 17:2742-2747, 2006.

Chen et al., "Natriuretic peptide receptors and neutral endopeptidase in mediating the renal actions of a new therapeutic synthetic natriuretic peptide dendroaspis natriuretic peptide," *J Am Coll Cardiol.*, 40(6):1186-1191, Sep. 18, 2002.

Chen et al., "Renal response to acute neutral endopeptidase inhibition in mild and severe experimental heart failure," *Circulation.*, 100(24):2443-2448, Dec. 14, 1999.

Chen et al., "Subcutaneous administration of brain natriuretic peptide in experimental heart failure," *J Am Coll Cardiol.*, 36(5):1706-1712, Nov. 1, 2000.

Chen et al., Abstract 909-2, "Subcutaneous BNP administration in symptomatic human heart failure: a novel therapeutic strategy for congestive heart failure," *J Am Coll Cardiol.*, 35(2s1):240A, Feb. 1, 2000, 1 page.

Chrisman and Garbers, "Reciprocal antagonism coordinates C-type natriuretic peptide and mitogen-signaling pathways in fibroblasts," *J Biol Chem.*, 274(7):4293-4299, Feb. 12, 1999.

Clavell et al., "Biological actions of brain natriuretic peptide in thoracic inferior vena caval constriction," *Am. J. Physiol.*, 265:R1416-R1422, 1993.

Cohn et al., "Cardiac remodeling-concepts and clinical implications: a consensus paper from an international forum on cardiac remodeling," *J. Am. Coll. Cardiol.*, 35(3):569-582, 2000.

Coresh et al., "Prevalence of chronic kidney disease in the United States," *JAMA.*, 298(17):2038-2047, Nov. 7, 2007.

Costello-Boerrigter et al., "Amino-terminal pro-B-type natriuretic peptide and B-type natriuretic peptide in the general community: determinants and detection of left ventricular dysfunction," *J Am Coll Cardiol.*, 47(2):345-353, Epub Jan. 4, 2006.

Costello-Boerrigter et al., "Renal and anti-aldosterone actions of vasopressin-2 receptor antagonism and B-type natriuretic peptide in experimental heart failure," *Circ Heart Fail.*, 3(3):412-419. Epub Feb. 22, 2010.

Costello-Boerrigter et al., "Vasopressin-2-receptor antagonism augments water excretion without changes in renal hemodynamics or sodium and potassium excretion in human heart failure," *Am J Physiol Renal Physiol.*, 2006, 290:F273-F278.

Cowie and Mendez, "BNP and congestive heart failure," *Prog Cardiovasc Dis.*, 44(4):293-321, Jan.-Feb. 2002.

Cunningham et al., "Production of an atrial natriuretic peptide variant that is specific for type A receptor," *EMBO J.*, 13(11):2508-2515, Jun. 1, 1994.

Currie et al., "Purification and sequence analysis of bioactive atrial peptides (atriopeptins)," *Science.*, 223(4631):67-69, Jan. 6, 1984.

da Costa Gonçalves et al., "Evidence that the vasodilator angiotensin-(1-7)-Mas axis plays an important role in erectile function," *Am J Physiol Heart Circ Physiol.*, 293(4):H2588-H2596. Epub Jul. 6, 2007.

Darbar et al., "Familial atrial fibrillation is a genetically heterogeneous disorder," *J. Am. Coll. Cardiol.*, 41(12):2185-2192, 2003.

(56) References Cited

OTHER PUBLICATIONS de Bold et al., "A rapid and potent natriuretic response to intravenous injection of atrial myocardial extract in rats," *Life Sci.*, 28(1):89-94, Jan. 5, 1981.

de Bold, "Atrial natriuretic factor of the rat heart. Studies on isolation and properties," *Proc Soc Exp Biol Med.*, 170(2):133-138, Jun. 1982.

De Mello, "Angiotensin (1-7) re-establishes impulse conduction in cardiac muscle during ischaemia-reperfusion. The role of the sodium pump," *J Renin Angiotensin Aldosterone Syst.*, 5(4):203-208, Dec. 2004.

Dean et al., "Synthesis and localization of C-type natriuretic peptide in mammalian kidney," *Am J Physiol.*, 266(3 Pt 2):F491-F496, Mar. 1994.

Deckard and Ebright, "Therapeutic hypothermia after cardiac arrest: What, why, who, and how," *American Nurse Today.*, 6(7):23-28, Jul. 2011.

Del Ry et al., "C-type natriuretic peptide and heart failure," *Pharmacol Res.*, 54(5):326-333. Epub Jul. 8, 2006.

Del Ry et al., "C-type natriuretic peptide plasma levels increase in patients with chronic heart failure as a function of clinical severity," *Eur J Heart Fail.*, 7(7):1145-1148, Dec. 2005.

Del Ry, "Radioimmunoassay for plasma C-type natriuretic peptide determination: a methodological evaluation," *Clinical Chemistry and Laboratory Medicine*, 43(6):641-645, Jun. 2005.

DelliPizzi et al., "Natriuretic action of angiotensin(1-7)," *Br J Pharmacol.*, 111(1):1-3, Jan. 1994.

Delporte et al., "Characterization and regulation of atrial natriuretic peptide (ANP)-R1 receptors in the human neuroblastoma cell line NB-OK-1," *Eur J Pharmacol.*, 207(1):81-88, May 25, 1991.

Di Nisio et al., "Direct thrombin inhibitors," *N Engl J Med.*, 353(10):1028-1040, Sep. 8, 2005.

Dickey et al., "A familial mutation renders atrial natriuretic peptide resistant to proteolytic degradation," *J. Biol. Chem.*, 284: 19196-19202, 2009.

Dickey et al., "Differential regulation of membrane guanylyl cyclases in congestive heart failure: natriuretic peptide receptor (NPR)-B, Not NPR-A, is the predominant natriuretic peptide receptor in the failing heart," *Endocrinology.*, 148(7):3518-3522, Epub Apr. 5, 2007.

Dickey et al., "Novel bifunctional natriuretic peptides as potential therapeutics," *J. Biol. Chem.*, 283(50):35003-35009, Dec. 2008, Epub Oct. 21, 2008.

Dietz et al., "Evidence supporting a physiological role for proANP-(1-30) in the regulation of renal excretion," *Am J Physiol Regul Integr Comp Physiol.*, 280(5):R1510-R1517, May 2001.

Dietz, "Mechanisms of atrial natriuretic peptide secretion from the atrium," *Cardiovasc Res.*, 68(1):8-17, Oct. 1, 2005.

Doi et al., "C-type natriuretic peptide induces redifferentiation of vascular smooth muscle cells with accelerated reendothelialization," *Arterioscler. Thromb. Vasc. Biol.*, 21(6):930-936, 2001.

Dong et al., "Overexpression of ACE2 enhances plaque stability in a rabbit model of atherosclerosis," *Arterioscler Thromb Vasc Biol.*, 28(7):1270-1276, Epub Apr. 10, 2008.

Dorner et al., "Hemodynamic effects of continuous urodilatin infusion: A dose finding study," *Clin. Pharmacol. Ther.*, 64:322-330, 1998.

D'Souza et al., "Autocrine and paracrine actions of natriuretic peptides in the heart," *Pharmacol Ther.*, 101(2):113-129, Feb. 2004.

D'Souza et al., "B-type natriuretic peptide limits infarct size in rat isolated hearts via KATP channel opening," *Am J Physiol Heart Circ Physiol.*, 284(5):H1592-H1600, Epub Jan. 9, 2003.

Edwards et al., "Atrial stretch, not pressure, is the principal determinant controlling the acute release of atrial natriuretic factor," *Circ Res.*, 62(2):191-195, Feb. 1988.

Elsner et al., "Efficacy of prolonged infusion of urodilatin [ANP-(95-126)] in patients with congestive heart failure," *Am Heart J.*, 129(4):766-773, Apr. 1995.

Espiner and Richards, "Atrial natriuretic peptide. An important factor in sodium and blood pressure regulation," *Lancet*, 1(8640):707-710, Apr. 1, 1989.

Espiner et al., "ABCs of natriuretic peptides: growth," *Horm Res*, Feb. 2007; 67(Suppl 1):81-90.

Fan et al., "Down-regulation does not mediate natriuretic peptide-dependent desensitization of natriuretic peptide receptor (NPR)-A or NPR-B: guanylyl cyclase-linked natriuretic peptide receptors do not internalize," *Mol. Pharmacol.*, 67:174-183, 2005.

Fenelon et al., "Examination of the in vivo cardiac electrophysiological effects of nesiritide (human brain natriuretic peptide) in conscious dogs," *J. Cardiac Failure*, 8:320-325, 2002.

Ferrario and Iyer, "Angiotensin-(1-7): a bioactive fragment of the renin-angiotensin system," *Regul Pept.*, 78(1-3):13-18, Nov. 30, 1998.

Ferreira et al., "Angiotensin-(1-7) improves the post-ischemic function in isolated perfused rat hearts," *Braz J Med Biol Res.* 35(9):1083-1090, Epub Aug. 30, 2002.

Ferreira et al., "Angiotensin-(1-7): cardioprotective effect in myocardial ischemia/reperfusion," *Hypertension*, 38(3 Pt 2):665-668, Sep. 2001.

Floege et al., "Age-related glomerulosclerosis and interstitial fibrosis in Milan normotensive rats: a podocyte disease," *Kidney Int.*, 51(1):230-243, Jan. 1997.

Flynn et al., "The amino acid sequence of an atrial peptide with potent diuretic and natriuretic properties," *Biochem. Biophys. Res. Commun.*, 117(3):859-865, 1983.

Fonarow et al., "Factors identified as precipitating hospital admissions for heart failure and clinical outcomes: findings from OPTI-MIZE-HF," *Arch Intern Med.*, 168(8):847-854, Apr. 28, 2008.

Fonarow, "B-type natriuretic peptide: spectrum of application. Nesiritide (recombinant BNP) for heart failure," *Heart Failure Reviews*, 8:321-325, Oct. 2003.

Forfia et al., "Acute phosphodiesterase 5 inhibition mimics hemodynamic effects of B-type natriuretic peptide and potentiates B-type natriuretic peptide effects in failing but not normal canine heart," *J Am Coll Cardiol.*, 49(10):1079-1088, Epub Feb. 26, 2007.

Forssmann et al., "The renal urodilatin system: clinical implications," *Cardiovasc Res.*, 51(3):450-462, Aug. 15, 2001.

Fox et al., "Parental atrial fibrillation as a risk factor for atrial fibrillation in offspring," *JAMA*, 291:2851-2855, 2004.

Fox et al., "Prediction of risk of death and myocardial infarction in the six months after presentation with acute coronary syndrome: prospective multinational observational study (GRACE)," *BMJ.* 333(7578):1091, Epub Oct. 10, 2006.

Fraga-Silva et al., "The antithrombotic effect of angiotensin-(1-7) involves mas-mediated NO release from platelets," *Mol Med.*, 14(1-2):28-35, Jan.-Feb. 2008.

Friedl et al., "Natriuretic peptides and cyclic guanosine 3',5'-monophosphate in asymptomatic and symptomatic left ventricular dysfunction," *Heart.*, 76(2):129-136, Aug. 1996.

Funder and Reincke, "Aldosterone: a cardiovascular risk factor?" *Biochim Biophys Acta.*, 1802(12):1188-1192, Epub Aug 13, 2010.

Furuya et al., "C-type natriuretic peptide inhibits intimal thickening after vascular injury," *Ann N Y Acad Sci.*, 748:517-523, Jan. 17, 1995.

Furuya et al., "C-type natriuretic peptide is a growth inhibitor of rat vascular smooth muscle cells," *Biochem Biophys Res Commun.*, 177(3):927-931, Jun. 28, 1991.

Furuya et al., "Structural requirements of C-type natriuretic peptide for elevation of cyclic GMP in cultured vascular smooth muscle cells," *Biochem Biophys Res Commun.*, 183(3):964-969, Mar. 31, 1992.

Gaddam et al., "Aldosterone and cardiovascular disease," *Curr Probl Cardiol.*, 34(2):51-84, Feb. 2009.

Gagelmann et al., "Urodilatin (CDD/ANP-95-126) is not biologically inactivated by a peptidase from dog kidney cortex membranes in contrast to atrial natriuretic peptide/cardiodilatin (.alpha.-hANP/CDD-99-126)," *FEBS Lett.*, 233(2):249-254, 1988.

Gallagher and Tallant, "Inhibition of human lung cancer cell growth by angiotensin-(1-7)," *Carcinogenesis.*, 25(11):2045-2052, Epub Jul. 29, 2004.

(56) References Cited

OTHER PUBLICATIONS

Gandhi et al., "Causes and consequences of zinc dyshomeostasis in rats with chronic aldosteronism," *J Cardiovasc Pharmacol.*, 52(3):245-252, Sep. 2008.

Gao et al., "Clades of Adeno-associated viruses are widely disseminated in human tissues," *J Virol.*, 78(12):6381-3388, Jun. 2004.

Garbers et al., "Membrane guanylyl cyclase receptors: an update," *Trends Endocrinol Metab.*, 17(6):251-258, Epub Jun. 30, 2006.

Gaspari et al., "Type-C natriuretic peptide prevents development of experimental atherosclerosis in rabbits," *Clin Exp Pharmacol Physiol.*, 27(8):653-655, Aug. 2000.

Genbank Accession No. ADW08083, "Human brain natriuretic polypeptide (BNP)2 mature protein SeqID36," Mar. 24, 2005, 1 page.

Genbank Accession No. AEB63460, "HUMNATPEP_PEA_1_P2 residues 103-162," Oct. 20, 2005, 1 page.

GenBank Accession No. AJ712145 "AJ712145 CMPD01 *Homo sapiens* cDNA clone CMPD10397," Jun. 30, 2004, 1 page.

GenBank Accession No. AY530557 (GI No. 46487760), "Adeno-associated virus isolate rh.25 capsid protein VP1 (cap) gene, complete cds," 2 pages, Jun. 24, 2004.

GenBank Accession No. BC005893, "*Homo sapiens* natriuretic peptide precursor A, mRNA (cDNA clone MGC:14467 IMAGE:4273949), complete cds," Jul. 15, 2006, 2 pages.

GenBank Accession No. BQ130005, "ij83b04.x1 Human insulinoma *Homo sapiens* cDNA clone IMAGE:5777983 3-, mRNA sequence," Jul. 15, 2003, 2 pages.

GenBank Accession No. BQ130258, "ij83b04.y1 Human insulinoma *Homo sapiens* cDNA clone IMAGE:5777983 5- similar to SW:ANFB_HUMAN P16860 Brain Natriuretic Peptide Precursor ;, mRNA sequence," Jul. 15, 2003, 2 pages.

GenBank Accession No. JA062576 (GI No. 328343515), "Sequence 3 from Patent EP2298926," 1 page, Apr. 6, 2011.

GenBank Accession No. JA231827 (GI No. 330729561), "Sequence 3 from Patent EP2292779," 1 page, Apr. 26, 2011.

GenBank Accession No. JA232063 (GI No. 330731135), "Sequence 3 from Patent EP2292780," 1 page, Apr. 26, 2011.

GenBank Accession No. JA400113.1 (GI No. 346220229), "Sequence 3 from Patent EP2345731," 1 page, Sep. 9, 2011.

GenBank Accession No. M25296, "Human natriuretic peptide precursor mRNA, complete cds," Apr. 27, 1993, 1 page.

Gheorghiade et al., "Navigating the crossroads of coronary artery disease and heart failure," *Circulation*, 114(11):1202-1213, Sep. 12, 2006.

Girbes et al., "Renal Function Is the Most Important Determinant of Survival in Patients With Severe Congestive Heart Failure," *J Am Coll Cardiol.*, 31:154A, 1998.

GlaxoSmithKline, "Heart attack information provided by Coreg; Glossary" Coreg.com [online] archived Dec. 21, 2003. Retrieved from the Internet: <URL: http://www.coreg.com/recentmi/miglossary.html>, 5 pages.

Goeddel et al., "Synthesis of human fibroblast interferon by *E. coli*," *Nucleic Acids Res*, 8(18):4057-4074, 1980.

Goetz et al., "Evidence that urodilatin, rather than ANP, regulates renal sodium excretion," *J Am Soc Nephrol.*, 1(6):867-874, Dec. 1990.

Gollob et al., "Somatic mutations in the connexin 40 gene (GJA5) in atrial fibrillation," *N Engl J Med.*, 354(25):2677-2688, Jun. 22, 2006.

Gorelik et al., "Angiotensin 1-7 induces bradykinin-mediated relaxation in porcine coronary artery," *J Pharmacol Exp Ther.*, 286(1):403-410, Jul. 1998.

Grantham and Burnett, Jr., "Natriuretic Peptides in Cardiovascular Disease," *Natriuretic Peptides in Health and Disease*, Samson and Levin (eds.), Humana Press, pp. 309-326., 1997.

Grobe et al, "Chronic angiotensin-(1-7) prevents cardiac fibrosis in DOCA-salt model of hypertension," *Am J Physiol Heart Circ Physiol.*, 290(6):H2417-H2423, Epub Jan. 13, 2006.

Gudbjartsson et al., "Variants conferring risk of atrial fibrillation on chromosome 4q25 ," *Nature*, 448:353-357, 2007.

Gulberg et al., "Increased renal production of C-type natriuretic peptide (CNP) in patients with cirrhosis and functional renal failure," *Gut.*, 47(6):852-857, Dec. 2000.

Ha et al., "Dendroaspis natriuretic peptide protects the post-ischemic myocardial injury," *Regul Pept.*, 133(1-3):13-19. Epub Nov. 11, 2005.

Haber et al., "Application of a radioimmunoassay for angiotensin I to the physiologic measurements of plasma renin activity in normal human subjects," *J Clin Endocrinol Metab.*, 29(10):1349-1355, Oct. 1969.

Haller et al., "Safety issues specific to clinical development of protein therapeutics," *Clin Pharmacol Ther.*, 84(5):624-627, Nov. 2008, Epub Aug. 13, 2008.

Hann, "On the double bond isostere of the peptide bond: preparation of an enkephalin analogue," *J. Chem. Soc. Perkin Trans.*, 1:307-314, 1982.

Harrell et al., "Tutorial in Biostatistics. Multivariable prognostic models: issues in developing models, evaluating assumptions and adequacy, and measuring and reducing errors," *Stat Med.*, 15(4):361-387, Feb. 28, 1996.

Hata et al., "Effects of carperitide on the long-term prognosis of patients with acute decompensated chronic heart failure: the PROTECT multicenter randomized controlled study," *Circ J.*, 72(11):1787-1793, Epub Sep. 24, 2008.

Hawkridge et al., "Quantitative mass spectral evidence for the absence of circulating brain natriuretic peptide (BNP-32) in severe human heart failure," *Proc Natl Acad Sci U S A.*, 102(48):17442-17447, Epub Nov. 17, 2005.

He et al., "Structural determinants of natriuretic peptide receptor specificity and degeneracy," *J Mol Biol.*, 361(4):698-714, Epub Jul. 2006.

Heidenreich et al., "Cost-effectiveness of screening with B-type natriuretic peptide to identify patients with reduced left ventricular ejection fraction," *J Am Coll Cardiol.*, 43(6):1019-1026, Mar. 17, 2004.

Heller et al., "Effect of intrarenal infusion of angiotensin-(1-7) in the dog," *Kidney Blood Press Res.*, 23(2):89-94, 2000.

Heublein et al , "Immunoreactivity and guanosine 3',5'-cyclic monophosphate activating actions of various molecular forms of human B-type natriuretic peptide," *Hypertension*, 49(5):1114-1119, Epub Mar. 19, 2007.

Hillock et al., "B-type natriuretic peptide infusions in acute myocardial infarction," *Heart.*, 94(5):617-622, Epub Jul. 16, 2007.

Hirofumi et al., "Plasma levels of brain natriuretic peptide in normal subjects and patients with chronic congestive heart failure: measurement by immunoradiometric assay (IRMA)," *Clinical Endocrinology*, 41(4):397-403, 1993 [English machine translation].

Hirsch et al., "ANP and Urodilatin: Who Is Who in the Kidney," *Eur J Med Res.*, 11:447-454, 2006.

Hobbs et al., "Natriuretic peptide receptor-C regulates coronary blood flow and prevents myocardial ischemia/reperfusion injury: novel cardioprotective role for endothelium-derived C-type natriuretic peptide," *Circulation*, 110(10):1231-1235, Epub Aug. 30, 2004.

Hodgson-Zingman, "Atrial natriuretic peptide frameshift mutation in familial fibrillation," *N. Engl. J. Med.*, 359(2):158-165, 2008.

Hoenig et al., "The cardiac microvasculature in hypertension, cardiac hypertrophy and diastolic heart failure," *Curr Vasc Pharmacol.*, 6(4):292-300, Oct. 2008.

Holladay et al., "Synthesis of hydroxyethylene and ketomethylene dipeptide isosteres," *Tetrahedron Lett.*, 24(41):4401-4404, 1983.

Horio et al., "Gene expression, secretion, and autocrine action of C-type natriuretic peptide in cultured adult rat cardiac fibroblasts," *Endocrinology.*, 144(6):2279-2284, Jun. 2003.

Hunt et al., "Bioactivity and metabolism of C-type natriuretic peptide in normal man," *J Clin Endocrinol Metab.*, 78(6):1428-1435, Jun. 1994.

Hunt et al., "Hypotension and bradycardia during caloric restriction in mice are independent of salt balance and do not require ANP receptor," *Am. J. Physiol. Heart Circ. Physiol.*, 287(4):H1446-H1451, 2004.

(56) References Cited

OTHER PUBLICATIONS

Hunter et al., "Measurement of the total proANP product in mammals by processing independent analysis," *J Immunol Methods.*, 370(1-2):104-110, Epub Jun. 15, 2011.
Huntley et al., "BNP-induced activation of cGMP in human cardiac fibroblasts: interactions with fibronectin and natriuretic peptide receptors," *J Cell Physiol.*, 209(3):943-949, Dec. 2006.
Ibebuogu et al., "Decompensated heart failure is associated with reduced corin levels and decreased cleavage of pro-atrial natriuretic peptide," *Circ Heart Fail.*, 4(2):114-120, Epub Jan. 7, 2011.
Ichiki and Burnett, Jr., "Protein therapeutics for cardiovascular disease: it is all about delivery," *J Am Coll Cardiol.*, 60(24):2558-2560, Epub Nov. 24, 2012.
Ichiki et al., "Abstract 11349: The natriuretic peptide prohormones are processed into active peptides in the normal human circulation and the processing is preserved in heart failure," *Circulation*, 126:A11349, 2012.
Ichiki et al., "All three NP pre/prohormones are processed in human blood into biologically active mature peptides," 16th Annual Scientific Meeting of Heart Failure Society of America, Sep. 10, 2012 [slideshow].
Ichiki et al., "All three NP pre/prohormones are processed in human blood into biologically active mature peptides," *J Card Fail.*, 18(8):53, Abstract 008, Aug. 2012.
Ichiki et al., "Corin is present in the normal human heart, kidney, and blood, with pro-B-type natriuretic peptide processing in the circulation," *Clin Chem.*, 57(1):40-47, Epub Nov. 12, 2010.
Ichiki et al., "Differential expression of the pro-natriuretic peptide convertases corin and furin in experimental heart failure and atrial fibrosis," *Am J Physiol Regul Integr Comp Physiol.*, 304(2):R102-R109, Nov. 14, 2012.
Ichiki et al., "Pro-Atrial Natriuretic Peptide in vitro and in vivo Normal Canines: A Selective Renal Enhancing Therapeutic," *J Card Fail.*, 19(8):527, Aug. 2013; HFSA 2013: Sep. 23, 2013. 17th Annual Scientific Meeting of the Heart Failure Society of America, Orland FL, USA.
Ichiki et al., "Pro-atrial natriuretic peptide 1-126 is processed in the human circulation to a mature GC-A activating peptide with therapeutic potential in heart failure," ESC Congress 2013, Amsterdam, Netherland, Aug. 31, 2013.
Ichiki et al., "Pro-atrial natriuretic peptide 1-126 is processed in the human circulation to a mature GC-A activating peptide with therapeutic potential in heart failure," *Eur Heart J.*, 34 (suppl 1): doi:10.1093/eurheartj/eht307.66, Aug. 31, 2013 [abstract].
Ichiki et al., "The natriuretic peptide prohormones are processed into active peptides in the normal human circulation and the processing is preserved in heart failure," American Heart Association Scientific meeting, Nov. 7, 2012, [poster], 1 page.
Ichiki et al., "The processing and degradation of preproANP in the circulation in normal human and patients with heart failure," The 77th Annual Scientific Meeting of Japanese Circulation Society (JCS 2013), Yokohama, Japan, Mar. 16, 2013, 1 page.
Igaki et al., "Effects of intravenously administered c-type natriuretic peptide in humans: comparison with atrial natriuretic peptide," *Hypertens Res.*, 1998, 21(1):7-13, 1998.
Ikeda et al., "Natriuretic peptide family as a novel antimigration factor of vascular smooth muscle cells," *Arterioscler Thromb Vasc Biol.*, 17(4):731-736, Apr. 1997.
Inserte et al., "Urodilatin limits acute reperfusion injury in the isolated rat heart," *Cardiovasc Res.*, 45(2):351-359, Jan. 14, 2000.
Itoh et al., "Atrial natriuretic polypeptide inhibits hypertrophy of vascular smooth muscle cells," *J Clin Invest.*, 86(5):1690-1697, Nov. 1990.
Iusuf et al., "Angiotensin-(1-7): pharmacological properties and pharmacotherapeutic perspectives," *Eur J Pharmacol.*, 585(2-3):303-312, Epub Mar. 15, 2008.
Iwata et al., "Angiotensin-(1-7) binds to specific receptors on cardiac fibroblasts to initiate antifibrotic and antitrophic effects," *Am J Physiol Heart Circ Physiol.*, 289(6):H2356-H2363. Epub Jul. 15, 2005.
Ji et al., "Role of angiotensin-converting enzyme 2 and angiotensin(1-7) in 17beta-oestradiol regulation of renal pathology in renal wrap hypertension in rats," *Exp Physiol.*, 93(5):648-657, Epub Feb. 22, 2008.
Jin et al., "Novel Analog of Atrial Natriuretic Peptide Selective for Receptor-A Produces Increased Diuresis and Natriuresis in Rats," *J Clin Invest*, 98(4):969-976, 1996.
Johns et al., "Dendroaspis natriuretic peptide binds to the natriuretic peptide clearance receptor," *Biochem Biomes Res Commun.*, 358(1):145-149, Epub Apr. 19, 2007.
Jougasaki et al., "Augmented cardiac cardiotrophin-1 in experimental congestive heart failure," *Circulation*, 101:14-17, 2000.
Kalra et al., "Cardiorenal disease: a clinical intersection," *International Urol. and Nephrol.*, 37(1):175-184, 2005.
Kalra et al., "C-type natriuretic peptide production by the human kidney is blunted in chronic heart failure," *Clin Sci* (Lond)., 118(1):71-77, Oct. 2, 2009.
Kambayashi et al., "Isolation and sequence determination of human brain natriuretic peptide in human atrium," *FEBS Lett.*, 259(2):341-345, 1990.
Kariya et al., "Antiproliferative action of cyclic GMP-elevating vasodilators in cultured rabbit aortic smooth muscle cells," *Atherosclerosis*, 80(2):143-147, Dec. 1989.
Kasama et al., "Effects of intravenous atrial natriuretic peptide on cardiac sympathetic nerve activity and left ventricular remodeling in patients with first anterior acute myocardial infarction," *J Am Coll Cardiol.*, 49(6):667-674. Epub Jan. 26, 2007.
Kato et al., "Atrial natriuretic peptide promotes cardiomyocyte survival by cGMP-dependent nuclear accumulation of zyxin and Akt," *J Clin Invest.*, 115(10):2716-2730, Oct. 2005.
Keidar et al., "ACE2 of the heart: From angiotensin I to angiotensin (1-7)," *Cardiovasc Res.*, 73(3):463-469. Epub Sep. 19, 2006.
Kenny and Stephenson, "Role of endopeptidase-24.11 in the inactivation of atrial natriuretic peptide," *FEBS Lett.*, 232(1):1-8, May 9, 1988.
Kenny et al., "Hydrolysis of human and pig brain natriuretic peptides, urodilatin, C-type natriuretic peptide and some C-receptor ligands by endopeptidase-24.11," *Biochem J.*, 291 (Pt 1):83-88, Apr. 1, 1993.
Kitakaze et al., "Human atrial natriuretic peptide and nicorandil as adjuncts to reperfusion treatment for acute myocardial infarction (J-WIND): two randomised trials," *Lancet.*, 370(9597):1483-1493, Oct. 27, 2007.
Kitakaze et al., "Large-scale trial using atrial natriuretic peptide or nicorandil as an adjunct to percutaneous coronary intervention for ST-segment elevation acute myocardial infarction," [abstract] *Circulation*, 114:2425-2426, 2006.
Kjems et al., "The influence of GLP-1 on glucose-stimulated insulin secretion: effects on beta-cell sensitivity in type 2 and nondiabetic subjects," *Diabetes*, 52(2):380-386, Feb. 2003.
Koitka et al., "Angiotensin converting enzyme 2 in the kidney," *Clin Exp Pharmacol Physiol.*, 35(4):420-425, Apr. 2008.
Koller et al., "Selective activation of the B natriuretic peptide receptor by C-type natriuretic peptide (CNP)," *Science.*, 252(5002):120-123, Apr. 5, 1991.
Komatsu et al., "C-type natriuretic peptide (CNP) in rats and humans," *Endocrinol.*, 129(2):1104-1106, Aug. 1991.
Kuhn, "Structure, regulation, and function of mammalian membrane guanylyl cyclase receptors, with a focus on guanylyl cyclase-A," *Circ Res.*, 93(8):700-709, Oct. 17, 2003.
Kumar et al., "Expression of Guanylyl Cyclase-A/Atrial Natriuretic Peptide Receptor Blocks the Activation of Protein Kinase C in Vascular Smooth Muscle Cells: Role of cGMP and GMP-Dependent Protein Kinase," *Hypertension*, 29 (1 Pt 2):414-421, 1997.
La Villa et al., "Different effects of atrial and c-type natriuretic peptide on the urinary excretion of endothelin-1 in man," *Clin. Sci.* (*Lond*), 95(5):595-602, 1998.
Lai et al., "Gene expression and synthesis of natriuretic peptides by cultured human glomerular cells," *J Hypertens.*, 17(4):575-583, Apr. 1999.
Lambert et al., "Angiotensin-converting enzyme 2 and new insights into the renin-angiotensin system," *Biochem Pharmacol.*, 75(4):781-786, Epub Aug. 17, 2007.

(56) References Cited

OTHER PUBLICATIONS

Langenickel et al., "Cardiac hypertrophy in transgenic rats expressing a dominant-negative mutant of the natriuretic peptide receptor B," *Proc Natl Acad Sci U S A.*, 103(12):4735-4740, Epub Mar. 14, 2006.
le Tran and Forster, "Angiotensin-(1-7) and the rat aorta: modulation by the endothelium," *J Cardiovasc Pharmacol.*, 30(5):676-682, Nov. 1997.
Leader et al., "Protein therapeutics: A summary and pharmacological classification," *Nat Rev Drug Discov.*, 7:21-39, Jan. 2008.
Lee and Burnett, Jr., "Discovery of a Novel Designer Natriuretic Peptide, CBB-NP" ASCPT American Society for Clinical Pharmacology and Therapeutics, [slideshow], 19 pages, Apr. 5, 2008.
Lee and Burnett, Jr., "Natriuretic peptides and therapeutic applications," *Heart Fail. Rev.*, 12(2):131-142, Jun. 2007.
Lee and Burnett, Jr., Abstract 10, "Discovery of a Novel Synthetic Natriuretic Peptide, CU-NP," *J Card Fail.*, 13(6)(Suppl 2):S74, Aug. 2007.
Lee and Burnett, Jr., Abstract 143, "Design, synthesis, and cardiorenal actions of a novel peptide, CDD-NP," *J Clin Pharmacol*, 48(9):1132, Sep. 2008.
Lee and Burnett, Jr., Abstract 147, "Design, synthesis, and in vivo actions of a novel designer natriuretic peptide, BUA-NP," *J Clin Pharmacol.*, 48(9):1133, [presented as a poster] Thirty-Seventh Annual Meeting of the American College of Clinical Pharmacology in Philadelphia, PA on Sep. 15, 2008.
Lee and Burnett, Jr., Abstract 179 "Design, synthesis, and in vivo pharmacologic actions of a novel designer natriuretic peptide fusing human atrial natriuretic peptide and human B-type natriuretic peptide," *Can J Cardiol.*, vol. 24 Suppl E, p. 85E, [presented as a poster] presented at The Canadian Cardiovascular Congress in Toronto, Canada on Oct. 26, 2008.
Lee and Burnett, Jr., Abstract 851 "Pharmacodynamics of a novel designer natriuretic peptide, BUA-NP, in normal anesthetized dogs," Pulsus, [online] 2009 [retrieved on Dec. 11, 2013]. Retrieved from the Internet: <URL: http://www.pulsus.com/ccc2009/abs/701. htm>, 1 page, Canadian Cardiovascular Congress, 62nd Annual Meeting of the Canadian Cardiovascular Society, 2009.
Lee and Burnett, Jr., Abstract 9, "Engineered mutation of human B-type nautriuretic peptide to preserve renal perfusion pressure," *J Card Fail.*, 14(6) Suppl: S3-S4, Aug. 2008. Presented as an oral presentation at The 12th Annual Scientific Meeting of the Heart Failure Society of America in Toronto, Canada on Sep. 22, 2008.
Lee and Burnett, Jr., Abstract F-PO140, "Renal Actions of a Novel Designer Natiuretic Peptide, CU-NP," *J. Am. Soc. Nephrol.*, 18:136A, 2007.
Lee and Burnett, Jr., Abstract PI-09, "Design, synthesis and biological actions of a novel designer natriuretic peptide, CAA-NP," *Clinical Pharmacology & Therapeutics*, 83(Suppl. 1): S11, Mar. 2008.
Lee and Burnett, Jr., Abstract PT-04, "Discovery of a Novel Designer Natriuretic Peptide, CBB-NP" *Nature*, 83(Suppl. 1):52, Mar. 2008, 1 page.
Lee et al., "Designer natriuretic peptides," *J Invest Med.*, 57(1):18-21, Jan. 2009.
Lee et al., "Pharmacodynamics of a novel designer natriuretic peptide, CD-NP, in a first-in-human clinical trial in healthy subjects," *J Clin Pharmacol.*, 49(6):668-673, Epub Apr. 2009.
Lee et al., "Pharmacokinetic and pharmacodynamic study of a novel chimeric natriuretic peptide, CD-NP, in the normal dog," *BMC Pharmacol.*, 2007, 7(Suppl. 1):P38.
Lee et al., Abstract 144, "Evaluation of a novel designer peptide, CU-NP, in human aortic endothelial cells and in vivo" *J Clin Pharmacol.*, 48( 9):1132, Sep. 2008.
Lee et al., Abstract 145, "Cyclic GMP stimulating actions of two novel peptides, CU-NP and CNP-C, as assessed in isolated canine glomeruli," *J Clin Pharmacol*, 48(9):1133, Sep. 2008.
Lee et al., Abstract 146, "Hemoconcentrating effects of two novel designer natriuretic peptides, CU-NP and CBB-NP," *J Clin Pharmacol*, 48(9):1133, Sep. 2008.

Lee et al., Abstract 1485, "Tissue Specific Activation of cGMP by an Alternatively Spliced Form of BNP," *Circulation*, 118:S_335, 2008.
Lee et al., Abstract 1497, "A Novel Designer Natriuretic Peptide, CAA-NP, As Assessed in Human Aortic Endothelial Cells: Evidence for Involvement of Natriuretic Peptide Receptor-A (NPR-A) and NPR-B in Cyclic GMP Response," *Circulation*, 118:S_337-S_338, 2008.
Lee et al., Abstract 239, "Neurohormonal profile of a novel chimeric natriuretic peptide, CD-NP, as compared to C-type natriuretic peptide, in the normal dog," *J. Cardiac. Failure*, 13(6)Suppl:S144, 2007.
Lee et al., Abstract 2493, "Design synthesis, and pharmacologic actions of a novel designer natriuretic peptide: CU-NP" *Circulation* 116(16) Suppl. S:549-550, Oct. 2007 & 80th Annual Scientific Session of the American Heart Association, Nov. 4-7, 2007.
Lee et al., Abstract 2495, "Pharmacodynamic Profile of a Novel Chimeric Natriuretic Peptide, CD-NP, as Compared to C-Type Natriuretic Peptide," *Circulation*, 116:II_550, 2007.
Lee et al., Abstract 256, "Renal Mechanisms of Action of a Novel Designer Natriuretic Peptide, CU-NP" *J Card Fail.*, 14(6S):S79-S80, Aug. 2008.
Lee et al., Abstract 28, "Renal Cyclic GMP Stimulating Actions of a Novel Chimeric Natriuretic Peptide CD-NP in Isolated Glomeruli: Evidence for NPR-A Activation," *Journal of Cardiac Failure*, 14(6): S11, Aug. 2008, 12th Annual Scientific Meeting, Heart Failure Society of America, (HFSA), Sep. 21-24, 2008, Toronto, Ontario, Canada, 1 page.
Lee et al., Abstract 371, "Cardiorenal and Neurohumoral Actions of a Novel Designer Natriuretic Peptide, CU-NP, in Canine Experimental Heart Failure," *Circulation*, 118:S_293, 2008.
Lee et al., Abstract 5432, "Mutation of Three Amino Acids in the Disulfide-Ring of a CNP Based Chimeric Natriuretic Peptide Alters its Vascular Properties," *Circulation*, 118:S_549, 2008.
Lee et al., Abstract LBII-A-I, "Renal and Neurohumoral Actions of a Novel Chimeric Natriuretic Peptide, CD-NP," 2007, Late-breaking abstract accepted for the Annual Meeting of the American Society for Clinical Pharmacology and Therapeutics Meeting, 1 page, Mar. 21-24, 2007.
Lee et al., Abstract P140, "A Novel New Generation Designer Natriuretic Peptide, CBB-NP, Exerts Favorable Cardiorenal and Neurohumoral Actions," *Circulation*, 118:S_1475, 2008.
Lee et al., Abstract P1949, "A first-in-human clinical trial of a novel chimeric natriuretic peptide, CD-NP, in healthy subjects," *Eur Heart J*, 29(Abstract Supplement):299, 2008.
Lee et al., Abstract PI-08 "Renal actions of a novel designer natriuretic peptide, CU-NP, as compared to C-type natriuretic peptide," *Clinical Pharmacology & Therapeutics*, 83(Suppl. 1): S11, Mar. 2008.
Lee et al., Poster #8, "Design, synthesis and cardiorenal actions of two novel peptides derived from human B-type natriuretic peptide" ICRH's Young Investigators Forum, May 21-23, 2009, 1 page, Retrieved from the Internet: <URL: http://www.f2fe.com/yiforum/2009/fwyi09/5a%20Poster%20Abstracts%- 20Day%201.pdf>, 1 page.
Lee, "Engineered Mutation of Human B-Type Natriuretic Peptide to Preserve Renal Perfusion Pressure," [oral presentation slides] Jay N. Cohn New Investigator Clinical/Integrative Physiology Award Competition, The Annual Scientific Meeting of the Heart Failure Society of America, Sep. 22, 2008, 24 pages.
Levey et al., "A more accurate method to estimate glomerular filtration rate from serum creatinine: a new prediction equation. Modification of Diet in Renal Disease Study Group," *Ann Intern Med.*, 130(6):461-470, Mar. 16, 1999.
Levey, "Nondiabetic Kidney Disease," *N Engl J Med.*, 347(19):1505-1511, Nov. 7, 2002.
Levin et al., "Natriuretic peptides," *N Engl J Med.*, 339(5):321-328, Jul. 30, 1998.
Lewko et al., "C-type natriuretic peptide as a podocyte hormone and modulation of its cGMP production by glucose and mechanical stress," *Kidney Int.*, 66(3):1001-1008, Sep. 2004.

(56) References Cited

OTHER PUBLICATIONS

Li et al., "Angiotensin-(1-7) augments bradykinin-induced vasodilation by competing with ACE and releasing nitric oxide," *Hypertension.*, 29(1 Pt 2):394-400, Jan. 1997.
Lim et al., "In-vivo evaluation of an in situ polymer precipitation delivery system for a novel natriuretic peptide," *PLoS One.*, 8(2): e52484, Feb. 2013.
Lim et al., "Sustained delivery of a novel natriuretic peptide for three weeks with in situ polymer precipitation delivery system," *J Card Fail.*, 18(8):563, Aug. 2012 [abstract].
Lin et al., "Human atrial natriuretic peptide gene delivery reduces blood pressure in hypertensive rats," *Hypertension*, 26(6 Pt 1):847-853, Dec. 1995.
Lisy and Burnett, Jr., "The Design, Synthesis and Cardiorenal Actions of a New Chimeric Natriuretic Peptide CD-NP," *J Am Coll Cardiol.*, 41(6 Suppl 1):312A, Abstract 860-1, 1 page, 2003.
Lisy et al., "A new natriuretic peptide present in canine plasma and heart," *J Card Fail*, 4 (3) Suppl. 1, Abstract No. Y3, p. 1, 1998.
Lisy et al., "Abstract 2166: Design, synthesis and unique biological actions of CD-NP: A novel CNP-like chimeric natriuretic peptide," *Circulation*, 114(18)Suppl. S: 440, 2006.
Lisy et al., "Design, Synthesis, and Actions of a Novel Chimeric Natriuretic Peptide: CD-NP," *J Am Coll Cardiol.*, 52(1): 60-68, Jul. 2008.
Lisy et al., "Design, synthesis, and cardiorenal actions of a novel small natriuretic peptide: CT-DNP," *J Am Coll Cardiol.*, Feb. 1, 2005; 45(3):419A, Abstract 1128-120.
Lisy et al., "Renal actions of synthetic dendroaspis natriuretic peptide," *Kidney Int.*, 56(2):502-508, Aug. 1999.
Lisy et al., "The new designer peptide CD-NP unloads the heart, suppresses renin and is natriuretic in vivo," *J Card Fail.*, 9(5)Suppl 1:S32, abstract 112, Oct. 2003.
Lisy et al., "Therapeutic Action of a New Natriuretic and Vasoactive Peptide DNP in Experimental Severe Congestive Heart Failure," *Circulation*, V. 100 (18) Supplement 1, Abstract No. 3354,(Nov. 2, 1999),pp. 1-636.
Lisy et al., "Therapeutic actions of a new synthetic vasoactive and natriuretic peptide, dendroaspis natriuretic peptide, in experimental severe congestive heart failure," Congestive Heart Failure, *Hypertension*, 37, Obtained from Chemical Abstracts, 135(2):130 Abstract 14664, Jul. 9, 2001, 3 pages.
Lisy et al., "Therapeutic actions of a new synthetic vasoactive and natriuretic peptide, dendroaspis natriuretic peptide, in experimental severe congestive heart failure," *Hypertension.*, 37(4):1089-1094, Apr. 2001.
Lisy et al., "Unique Renal and Systemic Hemadynamic Action of a New Natriuretic Peptide in Experimental Heart Failure," *JACC*, Abstract No. 1199-17, p. 202A, Feb. 1999.
Lloyd-Jones et al., "Lifetime risk for development of atrial fibrillation: The framingham heart study," *Circulation*, 110:1042-1046, 2004.
Longenecker et al., "Validation of Comorbid Conditions on the End-Stage Renal Disease Medical Evidence Report: The CHOICE Study," *J. Am. Soc. Nephrol.*, 2000, 11:520-529.
Loot et al., "Angiotensin-(1-7) attenuates the development of heart failure after myocardial infarction in rats," *Circulation.*, 105(13):1548-1550, Apr. 2, 2002.
Luchner et al., "Angiotensin II in the evolution of experimental heart failure," *Hypertension*, 28(3):472-477, Sep. 1996.
Lüss et al., "Renal effects of ularitide in patients with decompensated heart failure," *Am Heart J.*, 155(6):1012.e1-8, Jun. 2008.
Malik et al., "Recent advances in protein and peptide drug delivery systems," *Curr Drug Deliv.*, 4(2):141-151, Apr. 2007.
Mangiafico et al., "Neutral endopeptidase inhibition and the natriuretic peptide system: an evolving strategy in cardiovascular therapeutics," *Eur Heart J.*, 34(12):886-893c, Epub Aug. 31, 2012.
Mann, "Cardiac remodeling as therapeutic target: treating heart failure with Cardiac Support Devices," *Heart Failure Reviews*, 10(2):93-94, 2005.

Margulies and Burnett, Jr , "Inhibition of cyclic GMP phosphodiesterases augments renal responses to atrial natriuretic factor in congestive heart failure," *J. Cardiac Failure*, 1:71-80, 1994.
Margulies et al., "Angiotensin inhibition potentiates the renal responses to neutral endopeptidase inhibition in dogs with congestive heart failure," *J. Clin. Invest.*, 88(5):1636-1642, Nov. 1991.
Margulies et al., "Induction and prevention of radiocontrast-induced nephropathy in dogs with heart failure," *Kidney Int.*, 38(6):1101-1108, Dec. 1990.
Marques et al., "An oral formulation of angiotensin-(1-7) produces cardioprotective effects in infarcted and isoproterenol-treated rats," *Hypertension*, 57(3):477-483, Epub Jan. 31, 2011.
Martin et al., "Abstract 1484: New Insights into the Kidney-Heart Connection: Mild Renal Insufficiency Induces Cardiac Fibrosis and Diastolic Dysfunction Followed by Late Systolic Impairment," *Circulation*, 118:S_334-S_335, 2008.
Martin et al., "CD-NP: a novel engineered dual guanylyl cyclase activator with anti-fibrotic actions in the heart," *PLoS One*, 7(12):e52422, Epub Dec. 18, 2012.
Martin et al., "Specific roles for atrial natriuretic peptide and brain natriuretic peptide as biomarkers in left ventricular dysfunction and coronary artery disease," *European Heart Journal*, vol. 25, p. 338, abstract 1949, Aug. 2004.
Martin et al., "Specific roles for the natriuretic peptides as biomarkers in coronary artery disease and left ventricular dysfunction," *J Card Fail.*, 10(4)Suppl: p. S47, abstract 107, Aug. 2004, presented at The 8th Annual Scientific Meeting of the HFSA, Toronto, Ontario, Canada, Sep. 12-15, 2004, 1 page.
Mathur et al., "Nesiritide—A new agent for acute decompensated heart failure," *Medical Journal of Armed Forces India*, 61(4): 375-376, 2005.
Mattingly et al., "Presence of C-type natriuretic peptide in human kidney and urine," *Kidney Int.*, 46(3):744-747, Sep. 1994.
McCurley et al., "Furosemide and the progression of left ventricular dysfunction in experimental heart failure," *J Am Coll Cardiol.*, 44(6):1301-1307, 2004.
McDonagh et al., "Biochemical detection of left-ventricular systolic dysfunction," *Lancet*, 351:9-13, 1998.
McKee et al., "The natural history of congestive heart failure: the Framingham study," *N Engl J Med.*, 285(26):1441-1446, Dec. 23, 1971.
McKie et al., "A human atrial natriuretic peptide gene mutation reveals a novel peptide with enhanced blood pressure-lowering, renal-enhancing, and aldosterone-suppressing actions," *J Am Coll Cardiol.*, 54(11):1024-1032, Sep. 8, 2009.
McKie et al., "A novel atrial natriuretic peptide based therapeutic in experimental angiotensin II mediated acute hypertension," *Hypertension*, 56:1152-1159, 2010.
Mckie et al., "CD-NP: An innovative designer natriuretic peptide activator of particulate guanylyl cyclase receptors for cardiorenal disease," *Curr. Heart Fail. Reports*, 7(3):93-99, 2010.
Menon et al., "Angiotensin-(1-7) inhibits growth of human lung adenocarcinoma xenografts in nude mice through a reduction in cyclooxygenase-2," *Cancer Res.*, 67(6):2809-2815, Mar. 15, 2007.
Mentzer, "Effects of perioperative nesiritide in patients with left ventricular dysfunction undergoing cardiac surgery:the NAPA Trial," *J Am Coll Cardiol.*, 49(6):716-726, Epub Dec. 11, 2006.
Michel et al, "Two N-terminally truncated forms of C-type natriuretic peptide from habu snake venom," *Peptides.*, 21(5):609-615, May 2000.
Miller et al., "Amphiphilic conjugates of human brain natriuretic peptide designed for oral delivery: in vitro activity screening," *Bioconjug Chem.*, 17(2):267-274, Mar.-Apr. 2006.
Miller et al., "Comparison of novel pro-BNP(1-108) and standard BNP assays in heart failure patients," *Clin Chim Acta.*, 413(9-10):920-926, Epub Feb. 16, 2012.
Misono et al., "Rat atrial natriuretic factor: isolation, structure and biological activities of four major peptides," *Biochem Biophys Res Commun.*, 123(2):444-451, Sep. 17, 1984.

(56) References Cited

OTHER PUBLICATIONS

Mitrovic et al., "Effects of the renal natriuretic peptide urodilatin (ularitide) in patients with decompensated chronic heart failure: a double-blind, placebo-controlled, ascending-dose trial," *Am Heart J.*, 150(6):1239, Dec. 2005.
Mitrovic et al., "Haemodynamic and clinical effects of ularitide in decompensated heart failure," *Eur Heart J.*, 27(23):2823-2832, Epub Oct. 30, 2006.
Mizuiri et al., "Expression of ACE and ACE2 in individuals with diabetic kidney disease and healthy controls," *Am J Kidney Dis.*, 51(4):613-623. Epub Mar. 4, 2008.
Moalem et al., "Atrial natriuretic peptide reverses the negative functional effects of stunning in rabbit myocardium," *Regul Pept.*, 132(1-3):47-52. Epub Oct. 11, 2005.
Molling, "Naked DNA for vaccine or therapy," *J. Mol. Med.*, 75:242-246, 1997.
Morley, "Modulation of the action of regulatory peptides by structural modification," *Trends Pharm. Sci.*, 463-468, 1980.
Mukoyama et al., "Brain natriuretic peptide as a novel cardiac hormone in humans. Evidence for an exquisite dual natriuretic peptide system, atrial natriuretic peptide and brain natriuretic peptide," *J Clin Invest.*, 87(4):1402-1412, Apr. 1991.
Naruko et al., "C-type natriuretic peptide and natriuretic peptide receptors are expressed by smooth muscle cells in the neointima after percutaneous coronary intervention," *Atherosclerosis*, 181(2):241-250, 2005.
Nemer et al., "Gene structure of human cardiac hormone precursor, pronatriodilatin," *Nature*, 312(5995):654-656, Dec. 13-19, 1984.
Newton-Cheh et al., "Association of common variants in NPPA and NPPB with circulating natriuretic peptides and blood pressure," *Nat Genet.*, 41(3):348-353, Epub Feb. 15, 2009.
Ng et al., "Diagnosis of heart failure using urinary natriuretic peptides," *Clin Sci (Lond).*, 106(2):129-133, Feb. 2004.
Ngo et al., "Computational Complexity, Protein Structure Prediction, and the Levinthal Paradox," The Protein Folding Problem and Tertiary Structure Prediction, Merz and Grand, Eds, Birkhauser, Boston, pp. 433-506, 1994.
Nicholls, "The natriuretic peptides in heart failure," *J. Int. Med.*, 235:515-526, Jun. 1994.
Niederkofler et al., "Detection of endogenous b-type natriuretic peptide at very low concentrations in patients with heart failure," *Circ Heart Fail.*, 1(4):258-264, Epub Oct. 14, 2008.
Nieminen et al., "Executive summary of the guidelines on the diagnosis and treatment of acute heart failure: the Task Force on Acute Heart Failure of the European Society of Cardiology," *Eur Heart J.*, 26(4):384-416, Epub Jan. 28, 2005.
Nir et al., "CNP is present in canine renal tubular cells and secreted by cultured opossum kidney cells," *Am J Physiol.*, 267(6 Pt 2):R1653-R1657, Dec. 1994.
Nishida et al., "Effects of brain natriuretic peptide on hemodynamics and renal function in dogs," *Jpn J Physiol.*, 40(4):531-540, 1990.
Nomura et al., "Multicenter prospective investigation on efficacy and safety of carperitide as a first-line drug for acute heart failure syndrome with preserved blood pressure: COMPASS: Carperitide Effects Observed Through Monitoring Dyspnea in Acute Decompensated Heart Failure Study," *Circ J.*, 72(11):1777-1786, Epub Oct. 3, 2008.
O'Connor et al., "Effect of nesiritide in patients with acute decompensated heart failure," *N Engl J Med.*, 365(1):32-43, Jul. 7, 2011.
Ogawa et al., "Crystal structure of hormone-bound atrial natriuretic peptide receptor extracellular domain: rotation mechanism for transmembrane signal transduction," *J Biol Chem.*, 279(27):28625-28631, Epub Apr. 26, 2004.
Ogawa et al., "Human c-type natriuretic peptide, characterization of the gene and peptide," *Hypertension*, 19(6 Pt 2):809-813, Jun. 1992.
Ogawa et al., "Molecular cloning of the complementary DNA and gene that encode mouse brain natriuretic peptide and generation of transgenic mice that overexpress the brain natriuretic peptide gene," *J Clin Invest.*, 93(5):1911-1921, May 1994.
Oikawa et al., "Cloning and sequence analysis of cDNA encoding a precursor for human atrial natriuretic polypeptide," *Nature*, 309(5970):724-726, Jun. 21-27, 1984.
Okawa et al., "Preischemic infusion of alpha-human atrial natriuretic peptide elicits myoprotective effects against ischemia reperfusion in isolated rat hearts," *Mol Cell Biochem.*, 248(1-2):171-177, Jun. 2003.
Okolicany et al., "Clearance receptor and neutral endopeptidase-mediated metabolism of atrial natriuretic factor," *Am J Physiol.*, 263(3 Pt 2):F546-F553, Sep. 1992.
Olivetti et al., "Cardiomyopathy of the aging human heart. Myocyte loss and reactive cellular hypertrophy," *Circ Res.*, 68(6):1560-1568, Jun. 1991.
Olson et al., "Kv1.5 channelopathy due to KCNA5 loss-of-function mutation causes human atrial fibrillation," *Hum Mol Genet.*, 15(14):2185-2191, Epub Jun. 13, 2006.
Olson et al., "Sodium channel mutations and susceptibility to heart failure and atrial fibrillation," *JAMA.*, 293(4):447-454, Jan. 26, 2005.
Osawa et al., "C-Type natriuretic peptide inhibits proliferation and monocyte chemoattractant protein-1 secretion in cultured human mesangial cells," *Nephron.*, 86(4):467-472, Dec. 2000.
Osman et al., "Molecular identification and immunohistochemical localization of atrial natriuretic peptide in the heart of the dromedary camel (*Camelus dromedarius*)." *Comp Biochem Physiol A Mol Integr Physiol.*, 139(4):417-424, Dec. 2004.
Owan et al., "The effects of nesiritide on renal function and diuretic responsiveness in acutely decompensated heart failure patients with renal dysfunction," *J Card Fail.*, 14(4):267-275, May 2008.
Padilla et al., "Intravenous administration of the natriuretic peptide urodilatin at low doses during coronary reperfusion limits infarct size in anesthetized pigs," *Cardiovasc Res.*, 51(3):592-600, Aug. 15, 2001.
Pagel-Langenickel et al., "Natriuretic peptide receptor B signaling in the cardiovascular system: protection from cardiac hypertrophy," *J Mol Med (Berl).*, 85(8):797-810. Epub Apr. 12, 2007.
Pan et al., "Alternatively spliced forms of human BNP: Discovery, localization, and function," *Circulation*, vol. 110, No. 17, Suppl. III, p. III-96, Abstract 452, Oct. 26, 2004.
Pan et al., "Biodesign of a renal-protective peptide based on alternative splicing of B-type natriuretic peptide," *Proc. Natl. Acad. Sci. USA*, 106(27):11282-11287, Epub Jun. 18, 2009.
Pan et al., "Interplay of angiotensin II and angiotensin(1-7) in the regulation of matrix metalloproteinases of human cardiocytes," *Exp Physiol.*, 93(5):599-612, Epub Feb. 22, 2008.
Pardoll and Beckerleg, "Exposing the immunology of naked DNA vaccines," *Immunity*, 3(2):165-169, Aug. 1995.
Park et al., "Therapeutic potential of atrial natriuretic peptide administration on peripheral arterial diseases," *Endocrinology.*, 149(2):483-491, Epub Nov. 8, 2007.
Parkhomenko, [Statin treatment for high-risk patients: From expectations to clinical practice] "Primenenie statinov u bolnykh vysokogo riska: put ot ozhidaniya k klinicheskoy praktike." [Ukranian Medical Journal] Ukr.Med.Chasopis, IX/X vol. 5, No. 79, pp. 67-71, 2010 [English translation].
Parrott et al., "Comparison of changes in ejection fraction to changes in impedance cardiography cardiac index and systolic time ratio," *Congest Heart Fail.*, 10(2 Suppl 2):11-13, Mar.-Apr. 2004.
Pawson et al., "Assembly of cell regulatory systems through protein interaction domains," *Science*, 300(5618):445-452, Apr. 18, 2003.
Peacock, "The B-type natriuretic peptide assay: a rapid test for heart failure," *Cleve Clin J Med.*, 69(3):243-251, Mar. 2002.
Peiró et al., "Endothelial dysfunction through genetic deletion or inhibition of the G protein-coupled receptor Mas: a new target to improve endothelial function," *J Hypertens.*, 25(12):2421-2425, Dec. 2007.
Pencina et al., "Evaluating the added predictive ability of a new marker: from area under the ROC curve to reclassification and beyond," *Stat Med.*, 27(2):157-172; discusion 207-12, Jan. 30, 2008.
Pörsti et al., "Release of nitric oxide by angiotensin-(1-7) from porcine coronary endothelium: implications for a novel angiotensin receptor," *Br J Pharmacol.*, 111(3):652-654, Mar. 1994.

(56) References Cited

OTHER PUBLICATIONS

Potter et al., "Natriuretic peptides, their receptors, and cyclic guanosine monophosphate-dependent signaling functions," *Endocr Rev.*, 27(1):47-72, Epub Nov. 16, 2005.
Potter, "Natriuretic peptide metabolism, clearance and degradation," *FEBS J.*, 278(11):1808-1817, Epub Apr. 7, 2011.
Prausnitz, "A peptide chaperone for transdermal drug delivery," *Nat. Biotechnol.*, 24(4):416-417, Apr. 2006.
Preston et al., "Synergistic effects of ANP and sildenafil on cGMP levels and amelioration of acute hypoxic pulmonary hypertension," *Exp Biol Med (Maywood).*, 229(9):920-925, Oct. 2004.
Publication Committee for the VMAC Investigators, "Intravenous nesiritide vs nitroglycerin for treatment of decompensated congestive heart failure: a randomized controlled trial," *JAMA.*, 287(12):1531-1540, Mar. 27, 2002; Erratum in *JAMA.*, 288(5):577, Aug. 7, 2002.
PubMed search for atrial natriuretic peptide; Nov. 24, 2009; 5 pages.
PubMed search for brain natriuretic peptide; Nov. 24, 2009; 3 pages.
PubMed search for C-type natriuretic peptide; Nov. 24, 2009; 4 pages.
PubMed search for DNP; Nov. 24, 2009; 4 pages.
Ralat et al., "Insulin-degrading enzyme modulates the natriuretic peptide-mediated signaling response," *J Biol Chem.*, 286(6):4670-4679. Epub Nov. 22, 2010.
Rastegar et al., "Atrial natriuretic peptide reduces the severe consequences of coronary artery occlusion in anaesthetized dogs," *Cardiovasc Drugs Ther.*, 14(5):471-479, Oct. 2000.
Redfield et al., "Cardiorenal and neurohumoral function in a canine model of early left ventricular dysfunction," *Circulation*, 87(6):2016-2022, Jun. 1993.
Remuzzi et al., "Nephropathy in Patients with Type 2 Diabetes," *N Engl J Med.*, 346(15):1145-1151, Apr. 11, 2002.
Ren et al., "Brain natriuretic peptide limits myocardial infarct size dependent of nitric oxide synthase in rats," *Clin Chim Acta.*, 377(1-2):83-87, Epub Oct. 5, 2006.
Ren et al., "Vasodilator action of angiotensin-(1-7) on isolated rabbit afferent arterioles," *Hypertension*, 39(3):799-802, Mar. 1, 2002.
Richards et al., "Atrial natriuretic hormone has biological effects in man at physiological plasma concentrations," *J Clin Endocrinol Metab.*, 67(6):1134-1139, Dec. 1988.
Richards et al., "BNP in hormone-guided treatment of heart failure," *Trends Endocrinol Metab.*, 13(4):151-155, May-Jun. 2002.
Rifkin et al., "Albuminuria, impaired kidney function and cardiovascular outcomes or mortality in the elderly," *Nephrol Dial Transplant.*, 25(5):1560-1567, Epub Dec. 15, 2009.
Ronco et al., "Cardio-renal syndromes: report from the consensus conference of the acute dialysis quality initiative," *Eur Heart J.*, 31(6):703-711, print Mar. 2010, Epub Dec. 25, 2009.
Rose and Giles, "Natriuretic peptide C receptor signalling in the heart and vasculature," *J Physiol.*, 586(2):353-366, Epub Nov. 15, 2007.
Rose et al., "C-type natriuretic peptide activates a non-selective cation current in acutely isolated rat cardiac fibroblasts via natriuretic peptide C receptor-mediated signaling," *J Physiol.*, 580(Pt 1):255-274, Epub Jan. 4, 2007.
Rossi et al., "Natriuretic peptide levels in atrial fibrillation: a prospective hormonal and Doppler-echocardiographic study," *J Am Coll Cardiol.*, 35(5):1256-1262, Apr. 2000.
Rule et al., "The association between age and nephrosclerosis on renal biopsy among healthy adults," *Ann Intern Med.*, 152(9):561-567, May 4, 2010.
Ruskoaho, "Cardiac hormones as diagnostic tools in heart failure," *Endocr Rev.*, 24(3):341-356, Jun. 2003.
Sabbatini et al., "C-type natriuretic peptide stimulates pancreatic exocrine secretion in the rat: Role of vegal afferent and efferent pathways, " *Eur. J. Pharmacol.*, 2007, 577:192-202.
Sabbatini et al., "Atrial natriuretic factor stimulates exocrine pancreatic secretion in the rat through NPR-C receptors," *Am J Physiol Gastrointest Liver Physiol.*, 285(5):G929-G937, Epub Jun. 26, 2003.
Sabrane et al., "Vascular endothelium is critically involved in the hypotensive and hypovolemic actions of atrial natriuretic peptide," *J Clin Invest.*, 115(6):1666-1674, Jun. 2005.
Sackner-Bernstein et al., "Risk of worsening renal function with nesiritide in patients with acutely decompensated heart failure," *Circulation*, 111(12):1487-1491, Epub Mar. 21, 2005.
Sagnella, "Practical implications of current natriuretic peptide research," *J Renin Angiotension Aldosterone Syst.*, 1(4):304-315, Dec. 2000.
Sampaio et al., "Systemic and regional hemodynamic effects of angiotensin-(1-7) in rats," *Am J Physiol Heart Circ Physiol.*, 284(6):H1985-H1994, Epub Feb. 6, 2003.
Sangaralingham et al., "The aging heart, myocardial fibrosis, and its relationship to circulating C-type natriuretic Peptide," *Hypertension*, 57(2):201-207, Epub Dec. 28, 2010.
Sangaralingham et al., "Urinary C-type natriuretic peptide excretion: a potential novel biomarker for renal fibrosis during aging," *Am J Physiol Renal Physiol.*, 301(5):F943-F952, Epub Aug. 24, 2011.
Sangawa et al., "Atrial natriuretic peptide protects against ischemia-reperfusion injury in the isolated rat heart," *Ann Thorac Surg.*, 77(1):233-237, Jan. 2004.
Santiago et al., "Lifetime overproduction of circulating Angiotensin-(1-7) attenuates deoxycorticosterone acetate-salt hypertension-induced cardiac dysfunction and remodeling," *Hypertension*, 55(4):889-896, Epub Mar. 8, 2010.
Santos et al., "Angiotensin-(1-7) is an endogenous ligand for the G protein-coupled receptor Mas," *Proc Natl Acad Sci U S A.*, 100(14):8258-8263, Epub Jun. 26, 2003.
Santos et al., "Mas deficiency in FVB/N mice produces marked changes in lipid and glycemic metabolism," *Diabetes*, 57(2):340-347, Epub Nov. 19, 2007.
Santos et al., "Recent advances in the angiotensin-converting enzyme 2-angiotensin(1-7)-Mas axis," *Exp Physiol.*, 93(5):519-527, Epub Feb. 29, 2008.
Sarzani et al., "Renin-angiotensin system, natriuretic peptides, obesity, metabolic syndrome, and hypertension: an integrated view in humans," *J Hypertens.*, 26(5):831-843, May 2008.
Sato et al., "Continuous low-dose human atrial natriuretic peptide promotes diuresis in oliguric patients after living donor liver transplantation," *Transplant Proc.*, 38(10):3591-3593, Dec. 2006.
Scarborough et al., "Truncated atrial natriuretic peptide analogs. Comparison between receptor binding and stimulation of cyclic GMP accumulation in cultured vascular smooth muscle cells," *J Biol Chem.*, 261(28):12960-12964, Oct. 5, 1986.
Schiavone et al., "Release of vasopressin from the rat hypothalamo-neurohypophysial system by angiotensin-(1-7) heptapeptide," *Proc Natl Acad Sci U S A.*, 85(11):4095-4098, Jun. 1988.
Schirger et al., "Presence of Dendroaspis natriuretic peptide-like immunoreactivity in human plasma and its increase during human heart failure," *Mayo Clin Proc.*, 74(2):126-130, Feb. 1999.
Schirger et al., "Vascular actions of brain natriuretic peptide: modulation by atherosclerosis and neutral endopeptidase inhibition," *J Am Coll Cardiol.*, 35(3):796-801, Mar. 1, 2000.
Schoenfeld et al., "Agonist selectivity for three species of natriuretic peptide receptor-A," *Mol Pharmacol.*, 47(1):172-180, Jan. 1995.
Schulz-Knappe et al., "Isolation and structural analysis of "urodilatin," a new peptide of the cardiodilatin-(ANP)-family, extracted from human urine," *Klin Wochenschr.*, 66(17):752-759, Sep. 1, 1988.
Schweitz et al., "A new member of the natriuretic peptide family is present in the venom of the green mamba (*Dendroaspis angusticeps*)," *J Biol Chem.*, 267(20):13928-13932, Jul. 15, 1992.
Scotland et al., "C-type natriuretic peptide inhibits leukocyte recruitment and platelet-leukocyte interactions via suppression of P-selectin expression," *Proc Natl Acad Sci U S A.*, 102(40):14452-14457, Epub Sep. 22, 2005.

(56) References Cited

OTHER PUBLICATIONS

Sezai et al., "Efficacy of continuous low-dose hANP administration in patients undergoing emergent coronary artery bypass grafting for acute coronary syndrome," *Circ J.*, 71(9):1401-1407, Sep. 2007.
Sezai et al., "Efficacy of continuous low-dose human atrial natriuretic peptide given from the beginning of cardiopulmonary bypass for thoracic aortic surgery," *Surg Today.*, 36(6):508-514, 2006.
Sezai et al., "Low-dose continuous infusion of human atrial natriuretic peptide during and after cardiac surgery," *Ann Thorac Surg.*, 69(3):732-738, Mar. 2000.
Silver, "The natriuretic peptide system: kidney and cardiovascular effects," *Curr Opin Nephrol Hypertens.*, 15(1):14-21, Jan. 2006.
Singh et al., "Novel snake venom ligand dendroaspis natriuretic peptide is selective for natriuretic peptide receptor-A in human heart: downregulation of natriuretic peptide receptor-A in heart failure," *Circ Res.*, 99(2):183-190. Epub Jun. 15, 2006.
Skrzypiec-Spring et al., "Isolated heart perfusion according to Langendorff—still viable in the new millennium," *J Pharmacol Toxicol Methods.*, 55(2):113-126, Epub May 26, 2006.
Smith and Waterman, "Comparison of Biosequences," *Adv. Appl. Math.*, 2:482-489, 1981.
Soeki et al., "C-type natriuretic peptide, a novel antifibrotic and antihypertrophic agent, prevents cardiac remodeling after myocardial infarction," *J Am Coll Cardiol.*, 45(4):608-616, Feb. 15, 2005.
Spatola et al., "Structure-activity relationships of enkephalins containing serially replaced thiomethylene amide bond surrogates," *Life Sci.*, 38(14):1243-1249, Jan. 28, 1986.
Spatola, *Vega Data*, vol. 1, No. 3, chapter 5, pp. 267-268, 1983, [Table of Contents].
Stein and Levin, "Natriuretic peptides: physiology, therapeutic potential, and risk stratification in ischemic heart disease, " *Am Heart J.*, 135(5 Pt 1):914-923, May 1998.
Steiner et al., "Pulmonary hypertension: inhaled nitric oxide, sildenafil and natriuretic peptides," *Curr Opin Pharmacol.*, 5(3):245-250, Jun. 2005.
Steiner et al., "Radioimmunoassay for cyclic nucleotides. III. Effect of ischemia, changes during development and regional distribution of adenosine 3',5'-monophosphate and guanosine 3',5'-monophosphate in mouse brain," *J Biol Chem.*, 247(4):1121-1124, Feb. 25, 1972.
Steiner et al., "Radioimmunoassay for cyclic nucleotides. I. Preparation of antibodies and iodinated cyclic nucleotides," *J Biol Chem.*, 247(4):1106-1113, Feb. 25, 1972.
Steiner et al., "The measurement of cyclic nucleotides by radioimmunoassay," *Adv Biochem Psychopharmacol.*, 3:89-111, 1970.
Stevens et al., "A functional role for endogenous atrial natriuretic peptide in a canine model of early left ventricular dysfunction," *J Clin Invest.*, 95(3):1101-1108, Mar. 1995.
Stevens et al., "A Modified Model of Tachycardia-Induced Cardiomyopathy: Insights into Humoral and Renal Adaptations," *Pathophysiology of Tachycardia-Induced Heart Failure*, 1996, Futura Publishing Co., Inc. NY, pp. 133-151.
Stevenson et al., "Idiotypic DNA vaccines against B-cell lymphoma," *Immunol Rev.*, 145:211-228, Jun. 1995.
Stingo et al., "Cardiovascular and renal actions of C-type natriuretic peptide," *Am J Physiol.*, 262(1 Pt 2):H308-H312, Jan. 1992.
Stingo et al., "Presence of C-type natriuretic peptide in cultured human endothelial cells and plasma," *Am J Physiol.*, 263(4 Pt 2):H1318-H1321, Oct. 1992.
Su et al., "Angiotensin-(1-7) inhibits angiotensin II-stimulated phosphorylation of MAP kinases in proximal tubular cells," *Kidney Int.*, 69(12):2212-2218, Epub May 3, 2006.
Sudoh et al., "A new natriuretic peptide in porcine brain," *Nature*, 332(6159):78-81, Mar. 3, 1988.
Sudoh et al., "C-type natriuretic peptide (CNP): a new member of natriuretic peptide family identified in porcine brain," *Biochem Biomes Res Commun.*, 168(2):863-870, Apr. 30, 1990.
Suga et al., "Characterization of natriuretic peptide receptors in cultured cells," *Hypertension*, 19(6 Pt 2):762-765, Jun. 1992.

Suga et al., "Endothelial production of C-type natriuretic peptide and its marked augmentation by transforming growth factor-beta. Possible existence of vascular natriuretic peptide system," *J Clin Invest.*, 90(3):1145-1149, Sep. 1992.
Suga et al., "Receptor selectivity of natriuretic peptide family, atrial natriuretic peptide, brain natriuretic peptide, and C-type natriuretic peptide," *Endocrinology.*, 130(1):229-239, Jan. 1992.
Supaporn et al., "Blunted cGMP response to agonists and enhanced glomerular cyclic 3',5'-nucleotide phosphodiesterase activities in experimental congestive heart failure," *Kidney Int.*, 50(5):1718-1725, Nov. 1996.
Suwa et al., "Multicenter prospective investigation on efficacy and safety of carperitide for acute heart failure in the 'real world' of therapy," *Circ J.*, 69(3):283-290, Mar. 2005.
Suzuki et al., "The role of the natriuretic peptides in the cardiovascular system," *Cardiovascular Res.*, 51(3):489-494, Aug. 15, 2001.
Takagi et al., "Alpha-human atrial natriuretic peptide, carperitide, reduces infarct size but not arrhythmias after coronary occlusion/reperfusion in dogs," *J Cardiovasc Pharmacol.*, 36(1):22-30, Jul. 2000.
Takata et al., "The beneficial effect of atrial natriuretic peptide on arrhythmias and myocardial high-energy phosphates after reperfusion," *Cardiovascular Res.*, 32(2):286-293, Aug. 1996.
Tallant et al., "Angiotensin-(1-7) inhibits growth of cardiac myocytes through activation of the mas receptor," *Am J Physiol Heart Circ Physiol.*, Oct. 2005 289(4):H1560-H1566, Epub Jun. 10, 2005.
Talwar et al., "Plasma cardiotrophin-1 following acute myocardial infarction: relationship with left ventricular systolic dysfunction," *Clin Sci (Lond).*, 102(1):9-14, Jan. 2002.
Tao et al., "Biological effects of C-type natriuretic peptide in human myofibroblastic hepatic stellate cells," *J Biol Chem.*, 274(34):23761-23769, Aug. 20, 1999.
Tawaragi et al., "Gene and precursor structures of human C-type natriuretic peptide," *Biochem Biophys Res Commun.*, 175(2):645-651, Mar. 15, 1991.
Teixeira et al., "Differential effects of the phosphodiesterase type 5 inhibitors sildenafil, vardenafil, and tadalafil in rat aorta," *J Pharmacol Exp Ther.*, 316(2):654-661, Epub Oct. 4, 2005.
Trask and Ferrario, "Angiotensin-(1-7): pharmacology and new perspectives in cardiovascular treatments," *Cardiovasc Drug Rev.*, 25(2):162-174, Summer 2007.
Tremblay et al., "Biochemistry and physiology of the natriuretic peptide receptor guanylyl cyclases," *Mol Cell Biochem.*, 230(1-2):31-47, Jan. 2002.
Tripathy et al , "Immune responses to transgene-encoded proteins limit the stability of gene expression after injection of replication-defective adenovirus vectors," *Nature Med.*, 2:545-550, 1996.
Tripathy et al., "Long-term expression of erythropoietin in the systemic circulation of mice after intramuscular injection of a plasmid DNA vector," *Proc Natl Acad Sci U S A*, 93:10876-10880, 1996.
Tripathy et al., "Stable delivery of physiologic levels of recombinant erythropoietin to the systemic circulation by intramuscular injection of replication-defective adenovirus," *Proc Natl Acad Sci U S A.*, 91(24):11557-11561, Nov. 22, 1994.
Tsuruda et al., "Brain natriuretic Peptide is produced in cardiac fibroblasts and induces matrix metalloproteinases," *Circ Res.*, 91(12):1127-1134, Dec. 13, 2002.
Tsuruda et al., "Cardiotrophin-1 Stimulation of Cardiac Fibroblast Growth : Roles for Glycoprotein 130/Leukemia Inhibitory Factor Receptor and the Endothelin Type A Receptor," *Cir Res.*, 90(2):128-134. Feb. 2002.
Tsurumi et al., "Direct intramuscular gene transfer of naked DNA encoding vascular endothelial growth factor augments collateral development and tissue perfusion," *Circulation.*, 94(12):3281-3290, Dec. 15, 1996.
Ueda et al., "Angiotensin(1-7) potentiates bradykinin-induced vasodilatation in man," *J Hypertens.*, 19(11):2001-2009, Nov. 2001.
Ueno et al., "Local expression of C-type natriuretic peptide markedly suppresses neointimal formation in rat injured arteries through an autocrine/paracrine loop," *Circulation*, 96(7):2272-2279, Oct. 7, 1997.

(56) References Cited

OTHER PUBLICATIONS

Valli et al., "Review of 10 years of the clinical use of brain natriuretic peptide in cardiology," *J Lab Clin Med.*, 134(5):437-444, Nov. 1999.
van den Akker, "Structural insights into the ligand binding domains of membrane bound guanylyl cyclases and natriuretic peptide receptors," *J Mol Biol.*, 311(5):923-937, Aug. 31, 2001.
Van den Berg et al., "Depletion of atrial natriuretic peptide during longstanding atrial fibrillation," *Europace*, 6(5):433-437, 2004.
Veronese and Mero, "The impact of PEGylation on biological therapies," *Biodrugs*, 22(5):315-329, 2008.
Veronese and Pasut, "PEGylation, successful approach to drug delivery," *Drug Discov Today.*, 10(21):1451-1458, Nov. 1, 2005.
Vesely et al, "Elimination of up to 80% of human pancreatic adenocarcinomas in athymic mice by cardiac hormones," *In Vivo.*, 21(3):445-451, May-Jun. 2007.
Vesely et al., "Five cardiac hormones decrease the number of human small-cell lung cancer cells," *Eur J Clin Invest.*, 35(6):388-398, Jun. 2005.
Vesely et al., "Four cardiac hormones cause cell death of melanoma cells and inhibit their DNA synthesis.," *Am J Med Sci.*, 334(5):342-349, Nov. 2007.
Vesely et al., "Four cardiac hormones eliminate up to two-thirds of human breast cancers in athymic mice," *In Vivo*, 21(6):973-978, Nov.-Dec. 2007.
Vesely et al., "Four peptide hormones decrease the number of human breast adenocarcinoma cells," *Eur J Clin Invest.*, 35(1):60-69, Jan. 2005.
Vesely et al., "Urodilatin and four cardiac hormones decrease human renal carcinoma cell numbers," *Eur J Clin Invest.*, 36(11):810-819, Nov. 2006.
Vesely, "Atrial natriuretic peptides in pathophysiological diseases," *Cardiovasc Res.*, 51(4):647-658, Sep. 2001.
Vesely, "Natriuretic peptides and acute renal failure," *Am J Physiol Renal Physiol.*, 285(2):F167-F177, Aug. 2003.
Vieira and Messing, "Production of single-stranded plasmid DNA," *Methods Enzymol.*, 153:3-11, 1987.
Villar et al., "Definitive role for natriuretic peptide receptor-C in mediating the vasorelaxant activity of C-type natriuretic peptide and endothelium-derived hyperpolarising factor," *Cardiovasc Res.*, 74(3):515-525, Epub Mar. 3, 2007.
von Geldern et al., "Small atrial natriuretic peptide analogues: design, synthesis, and structural requirements for guanylate cyclase activation," *J Med Chem.*, 35(5):808-816, Mar. 6, 1992.
Wakui, "Experimental study on myocardial protection by adjunct use of carperitide (hANP) in cardiac surgery," *Ann Thorac Cardiovasc Surg.*, 11(1):12-20, Feb. 2005.
Walther et al., "Natriuretic peptide system in fetal heart and circulation," *J. Hypertens.*, 20(5):786-791, 2002.
Wang et al., "AlbuBNP, a recombinant B-type natriuretic peptide and human serum albumin fusion hormone, as a long-term therapy of congestive heart failure," *Pharm Res.*, 21(11):2105-2111, Nov. 2, 2004.
Wang et al., "Chronic administration of angiotensin-(1-7) attenuates pressure-overload left ventricular hypertrophy and fibrosis in rats," *Di Yi Jun Yi Da Xue Xue Bao.* 25(5):481-487, May 2005.
Wang et al., "Natural history of asymptomatic left ventricular systolic dysfunction in the community," *Circulation*, 108(8):977-982, Epub Aug. 11, 2003.
Wang et al., "Plasma natriuretic peptide levels and the risk of cardiovascular events and death," *N Engl J Med.*, 350(7):655-663, Feb. 12, 2004.
Weber et al., "Myocardial fibrosis: functional significance and regulatory factors," *Cardiovasc Res.*, 27(3):341-348, Mar. 1993.
Wei et al., "Action of C-type natriuretic peptide in isolated canine arteries and veins," *Am J Physiol.*, 264(1 Pt 2):H71-H73, Jan. 1993.
Wei et al., "Angiotensin peptides modulate bradykinin levels in the interstitium of the dog heart in vivo," *J Pharmacol Exp Ther.*, 300(1):324-329, Jan. 2002.

Wei et al., "Atrial and pulmonary endothelin mRNA is increased in a canine model of chronic low cardiac output," *Am J Physiol.*, 273(2 Pt 2):R838-R844, Aug. 1997.
Wei et al., "Circulating beta-atrial natriuretic factor in congestive heart failure in humans," *Circulation*, 88(3):1016-1020, Sep. 1993.
Wei et al., "Natriuretic Peptide System in Human Heart Failure," *Circulation*, 88(3):1004-1009, Sep. 1993.
Wei et al., "Vasonatrin peptide: a unique synthetic natriuretic and vasorelaxing peptide," *J Clin Invest.*, 92(4):2048-2052, Oct. 1993.
Weinfeld et al., "Aggravated renal dysfunction during intensive therapy for advanced chronic heart failure," *Am Heart J.*, 138:285-290, 1999.
Weinstein and Anderson, "The aging kidney: physiological changes," *Adv Chronic Kidney Dis.*, 17(4):302-307, Jul. 2010.
Wennberg et al , "Inhibition of Nitric Oxide (NO), but not Neutral Endopeptidase (NEP), Augments CNP-mediated Coronary Relaxation in CHF," *J Am Coll Cardiol.*, 29:305A, 1997.
Wermeling et al., "Microneedles permit transdermal delivery of a skin-impermeant medication to humans," *Proc Natl Acad Sci U S A.*, 105(6):2058-2063, Feb. 12, 2008.
Wolff et al., "Direct Gene Transfer into Mouse Muscle in Vivo," *Science*, 1990, 247:1465-1468.
Wozakowska-Kaplon. "ANP and B-type peptide: Twins or kins? A different predictive value in atrial fibrillation Natriuretic peptides: Useful biomarkers in predicting the possibility of restoration and maintenance of sinus rhythm in patients with atrial fibrillation undergoing cardioversion," *J Cardiology*, 145 (2):234-235, 2010.
Xu et al., "Endothelial dysfunction and elevated blood pressure in MAS gene-deleted mice," *Hypertension.*, 51(2):574-580, Epub Jan. 7, 2008.
Yamamoto et al., "Effect of endogenous natriuretic peptide system on ventricular and coronary function in failing heart," *Am. J. Physiol.*, 273:H2406-H2414, 1997.
Yamamoto et al., "Ventricular remodeling during development and recovery from modified tachycardia-induced cardiomyopathy model," *Am. J. Physiol.*, 271:R1529-R1532, 1996.
Yan et al., "Corin, a mosaic transmembrane serine protease encoded by a novel cDNA from human heart," *J Biol Chem.*, 274(21):14926-14935, May 21, 1999.
Yan et al., "Corin, a transmembrane cardiac serine protease, acts as a pro-atrial natriuretic peptide-converting enzyme," *Proc Natl Acad Sci U S A.*, 97(15):8525-8529, Jul. 18, 2000.
Yang and Fogo, "Cell senescence in the aging kidney," *J Am Soc Nephrol.*, 21(9):1436-1439, Epub Aug. 12, 2010.
Yang et al., "Atrial natriuretic peptide administered just prior to reperfusion limits infarction in rabbit hearts," *Basic Res Cardiol.*, 101(4):311-318, Epub Apr. 8, 2006.
Yang et al., "Developing particle-mediated gene-transfer technology for research into gene therapy of cancer," *Mol. Med. Today*, 2(11):476-481, Nov. 1996.
Yasue et al., "Localization and mechanism of secretion of B-type natriuretic peptide in comparison with those of A-type natriuretic peptide in normal subjects and patients with heart failure," *Circulation*, 90(1):195-203, Jul. 1994.
Yellon and Hausenloy, "Myocardial reperfusion injury," *N Engl J Med.*, 357(11):1121-1135, Sep. 13, 2007.
Zhao et al., "Beneficial effects of phosphodiesterase 5 inhibition in pulmonary hypertension are influenced by natriuretic Peptide activity," *Circulation*, 107:234-237, 2003.
Zhou et al., "The aging kidney," *Kidney Int.*, 74(6):710-720, Epub Jul. 9, 2008.
Zierer et al., "Potential renal protective benefits of intra-operative BNP infusion during cardiac transplantation," *Transplant Proc.*, 38(10):3680-3684, Dec. 2006.
International Search Report and Written Opinion for PCT/US2013/020392 mailed Apr. 18, 2013, 6 pages.
International Preliminary Report on Patentability for PCT/US2013/020392 mailed Jul. 17, 2014, 5 pages.

* cited by examiner

Fig. 1
A
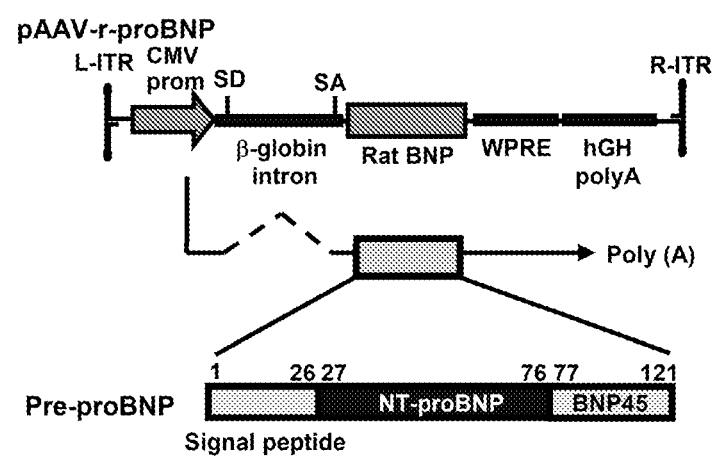
B
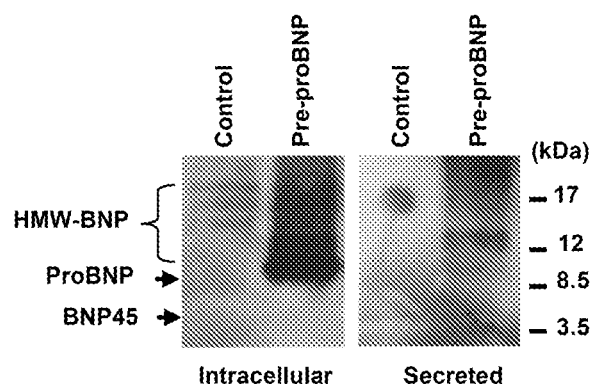
C
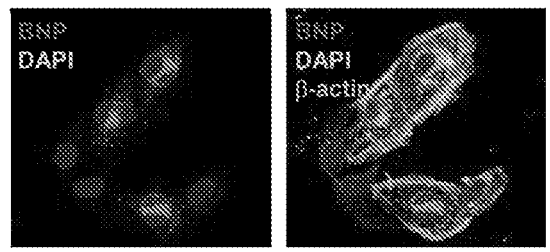

Fig. 3
A
|      | Untreated   | Treated      |
|------|-------------|--------------|
| irBNP45 | 60.6±15.1 | 433.3±17.0* |
| WBC  | 7.22±1.17   | 8.58±2.37    |
| RBC  | 10.5±0.31   | 10.9±0.22    |
| HGB  | 17.4±0.80   | 17.9±0.33    |
| HCT  | 48.4±1.32   | 49.8±1.94    |
| PLT  | 898±42.7    | 933±65.9     |
| ALB  | 5.13±0.29   | 5.28±0.38    |
| ALP  | 503±28.5    | 546±39.0     |
| ALT  | 68.0±1.83   | 69.8±2.87    |
| AMY  | 889±59.8    | 881±64.5     |
| TBIL | 0.20±0      | 0.23±0.05    |
| BUN  | 18.0±1.41   | 18.3±0.5     |
| PHOS | 5.3±0.29    | 5.95±1.29    |
| CRE  | 0.45±0.06   | 0.45±0.1     |
| GLU  | 186±16.5    | 208±12.8     |
| TP   | 6.90±0.22   | 7.15±0.24    |
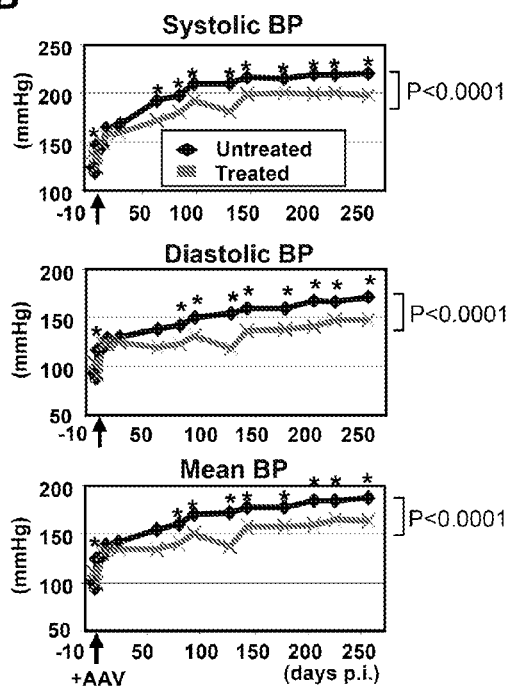
B
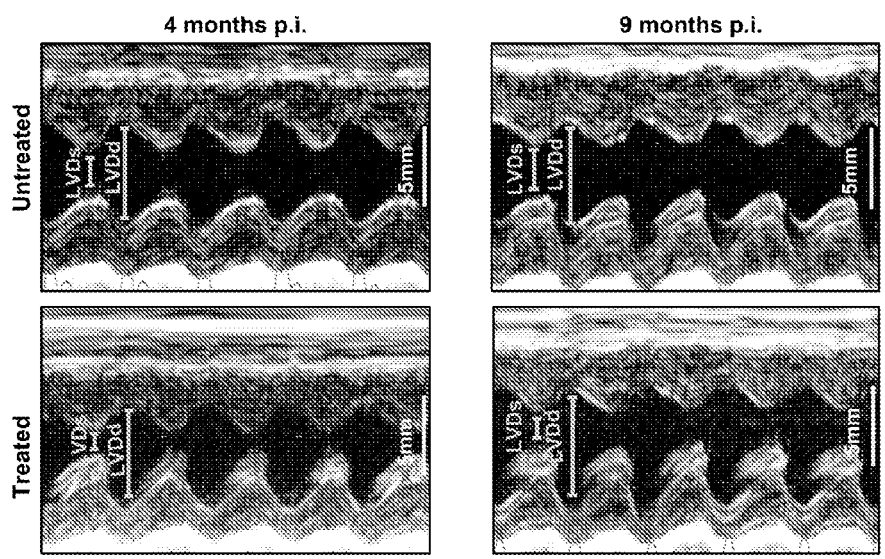
C

Fig. 4
|  | 9 months p.i. | |
| --- | --- | --- |
|  | Untreated | Treated |
| HR (arterial) | 318±33.3 | 320±45.7 |
| SBP (arterial) | 184±13.7 | 121±11.7* |
| DBP (arterial) | 148±24.2 | 103±5.6* |
*P<0.05 vs respective untreated rats (n=4)
B
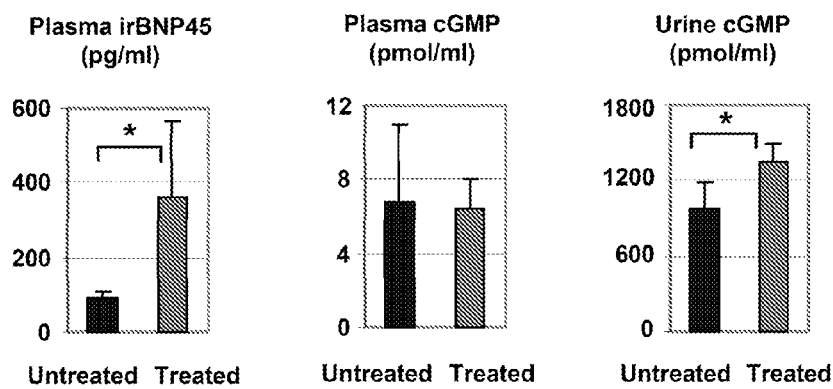
C
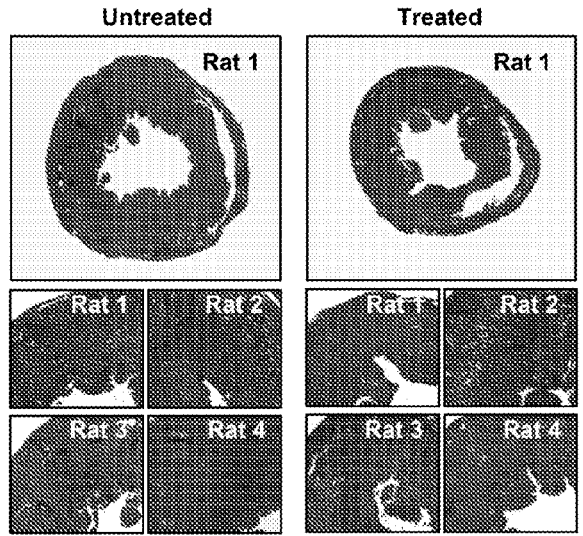
D
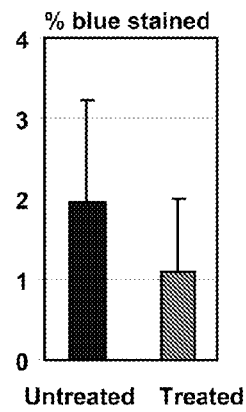

Fig. 5
A
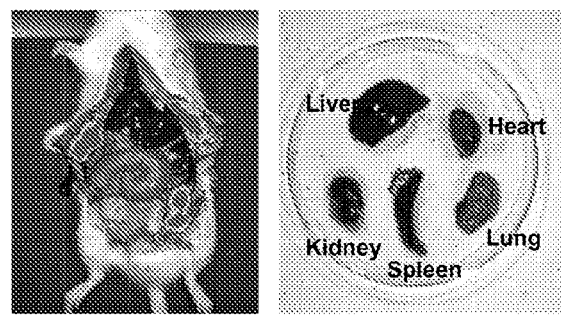
B
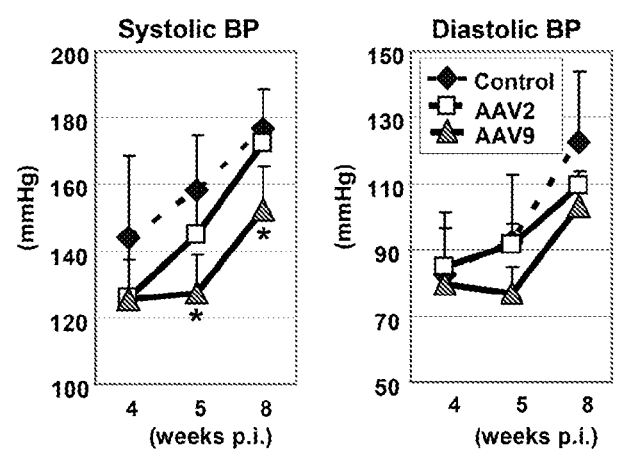
C
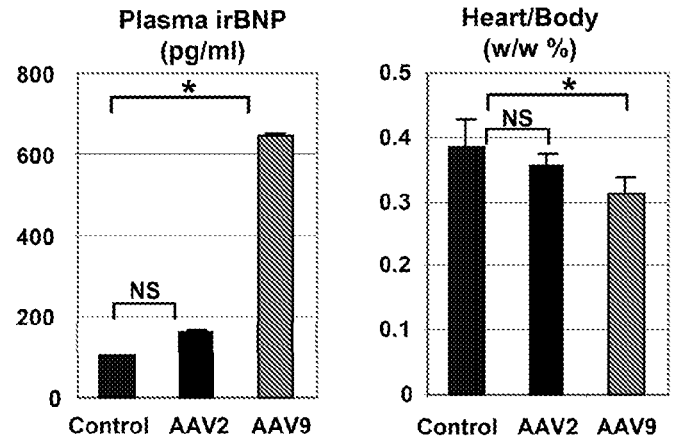

Fig. 6
A
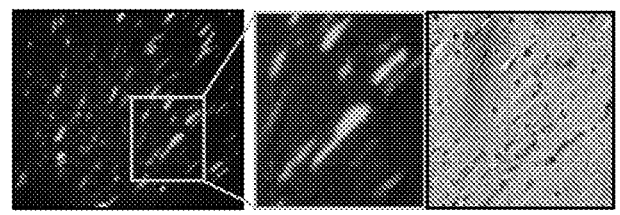
B
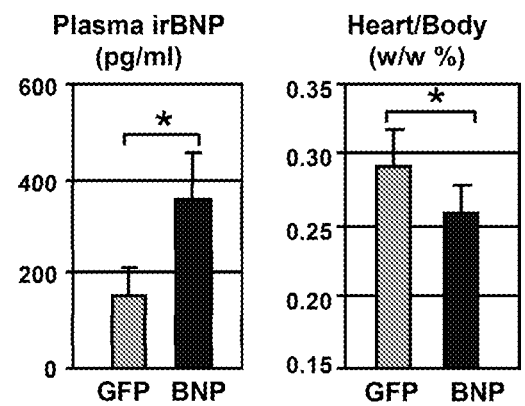
C
| | 4 weeks p.i. | |
|---|---|---|
| | Controls | BNP Treated |
| HR (arterial) | 311±30.8 | 317±29.7 |
| SBP (arterial) | 100±11.1 | 99.8±7.7 |
| DBP (arterial) | 85.8±10.8 | 80.0±8.6 |
No significant difference was observed between BNP vector treated and GFP vector-treated rats (n=6).

Figure 11

|  | Control (n=7) | proBNP (n=6) |
|---|---|---|
| HR | 359±24.2 | 385±18.9 |
| SWTd | 2.63±0.28 | 2.28±0.20* |
| PWTd | 2.28±0.13 | 2.26±0.23 |
| LVDd | 8.67+0.88 | 7.81±0.76 |
| SWTs | 3.84±0.38 | 3.35±0.19* |
| PWTs | 2.93±0.35 | 3.43±0.33* |
| LVDs | 6.00±1.35 | 4.69±0.56 |
| LV Mass diastole | 2.16±0.36 | 1.77±0.14* |
| EF (Cube) | 66.4±12.6 | 78.2±3.3* |
| EF (Teich) | 63.7±12.8 | 76.2±3.2* |
| %FS | 31.4±8.5 | 40±3.0* |

Figure 13

| Parameters for cardiac functions | Control | AAV9 proBNP |
|---|---|---|
| IVSd | 2.22 | 1.66* |
| LVIDd | 7.25 | 7.85* |
| LVPWd | 1.84 | 1.69 |
| IVSs | 3.19 | 2.83 |
| LVIDs | 4.45 | 4.88 |
| LVPWs | 2.57 | 2.46 |
| EFcube | 75.6 | 75.7 |
| EFteich | 73.4 | 73.3 |
| %FS | 38.5 | 38.0 |
| LVd Mass | 1.49 | 1.37 |
| VLs Mass | 1.41 | 1.38 |
| HR | 352.8 | 378.7 |
| Cardiac Output | 0.22 | 0.29* |

Figure 14 pre-pro-ANP amino acid sequence
(NCBI Reference Nucleotide Sequence: NM_006172.3)

MSSFSTTTVSFLLLLAFQLLLGQTRANPMYNAVSNADLMDFKNLLDHLEEKM
PLEDEVVPPQVLSEPNEEAGAALSPLPEVPPWTGEVSPAQRDGGALGRGPW
DSSDRSALLKSKLRALLTAPRSLRRSSCFGGRMDRIGAQSGLGCNSFRY

ANP pre-pro-mANP (frame-shifted mutant ANP) amino acid sequence

MSSFSTTTVSFLLLLAFQLLLGQTRANPMYNAVSNADLMDFKNLLDHLEEKM
PLEDEVVPPQVLSEPNEEAGAALSPLPEVPPWTGEVSPAQRDGGALGRGPW
DSSDRSALLKSKLRALLTAPRSLRRSSCFGGRMDRIGAQSGLGCNSFRYRI
TAREDKQGWA mANP (= fsANP)

Synthesized mANP-encoding nucleotide sequence (codon usage-optimized)

ATGAGCTCCTTTTCCACTACTACTGTGTCCTTTCTGCTGCTGCTGGCCTTCCAGCTGCTGCTGGGCCAAACCCGGCTAACCC
AATGTACAACGCCGTCAGCAATGCTGATCTGATGGATTTTAAGAATCTGCTGGATCACCTGGAGGAAAAGATGCCTCTGG
AAGACGAAGTGGTCCCTCCTCAAGTCCTGTCCGAACCTAACGAGGAAGCCGGCGCTGGGAAGCCCTCGAGCCTCTCCGAAGT
CCCACCCTGGACAGGGAGGTCAGCCCAGAAGCAAACTGAGGGCTGTGCTGCGCCCCTAGAAGCCTCAGGAGAAGCTCTGTTC
GACCGGAGCGCTCTGCTGAAAAGCAAACTGAGGGCTCTGCTGACCGCCCCTAGAAGCCTCAGGAGAAGCTCTGCTTC
GGCGAAGGATGACCGGATTGGGGCACAAAGCGCCTGGTAACTCCTTCCGGTATAGGATTACAGTAGAGAA
GATAAACAGGGCTGGGCTTAA

TREATING CARDIOVASCULAR OR RENAL DISEASES

CROSS-REFERENCE TO RELATED APPLICATIONS

This application is a National Stage application under 35 U.S.C. 371 of International Application No. PCT/US2013/020392, having an International Filing Date of Jan. 4, 2013, which claims the benefit of priority to U.S. Provisional Application Ser. No. 61/584,006, filed on Jan. 6, 2012. The disclosure of the prior application is considered part of (and is incorporated by reference in) the disclosure of this application.

STATEMENT AS TO FEDERALLY SPONSORED RESEARCH

This invention was made with government support under grant number HL098502 awarded by the National Institute of Health. The government has certain rights in the invention.

1. TECHNICAL FIELD

This document relates to methods and materials involved in treating cardiovascular and/or renal diseases. For example, this document relates to adeno-associated virus serotype 9 (AAV9) vectors designed to express natriuretic polypeptides, nucleic acid molecules encoding natriuretic polypeptides, methods for making AAV9 vectors, and methods for using such vectors or molecules to treat cardiovascular and/or renal diseases.

2. BACKGROUND INFORMATION

Hypertension is a highly common condition that, if not controlled, progresses toward more severe cardiovascular and renal morbidity. Its major clinical phenotype is hypertensive heart disease (HHD), which is characterized by diastolic dysfunction, cardiac remodeling, and fibrosis. Over time, diastolic dysfunction evolves into systolic impairment, which leads to the worsening of overall cardiac function and to increased morbidity and mortality.

SUMMARY

This document provides methods and materials for treating cardiovascular and/or renal diseases. For example, this document provides AAV9 vectors designed to express natriuretic polypeptides, nucleic acid molecules encoding natriuretic polypeptides, methods for making AAV9 vectors, and methods for using such vectors or molecules to treat cardiovascular and/or renal diseases. AAV9 was isolated from human tissues and shown to have serological characteristics distinct from previously described serotypes (Gao et al., *J. Virol.*, 78:6381-6388 (2004)).

As described herein, AAV9 vectors can be designed to have a nucleic acid sequence that encodes a natriuretic polypeptide such as an atrial natriuretic polypeptide (ANP), a B-type natriuretic polypeptide (BNP), a C-type natriuretic polypeptide (CNP), or a chimeric natriuretic polypeptide called CDNP. Such AAV9 vectors can be administered to a mammal (e.g., a human patient identified as suffering from a cardiovascular and/or renal disease) to treat that mammal's cardiovascular and/or renal disease. For example, an AAV9 vector provided herein can successfully deliver nucleic acid to cardiac cells for expression (e.g., sustained expression) of a natriuretic polypeptide without any short- or long-term toxicological effects and any signs of tolerance. In some cases, the sustained cardiac natriuretic polypeptide (e.g., BNP or CDNP) overexpression can reduce blood pressure (BP) and improve left ventricular (LV) function after a single administration (e.g., a single intravenous injection). In some cases, the AAV9 vectors provided herein can be used to reduce or prevent the development of hypertensive heart disease (HHD). Having the ability to deliver and express natriuretic polypeptide in cardiac cells as described herein can allow patients and clinicians to treat cardiovascular and/or renal diseases in an efficient and effective manner.

In general, one aspect of this document features an AAV9 vector comprising, or consisting essentially of, a nucleic acid sequence encoding a natriuretic polypeptide. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide.

In another aspect, this document features a composition comprising, or consisting essentially of, an AAV9 vector in combination with a pharmaceutically acceptable delivery vehicle. The AAV9 vector comprises, or consists essentially of, a nucleic acid sequence encoding a natriuretic polypeptide. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide.

In another aspect, this document features a method for a cardiovascular or renal disease. The method comprises, or consists essentially of, administering a vector or a composition to a mammal. The vector can be an AAV9 vector comprising, or consisting essentially of, a nucleic acid sequence encoding a natriuretic polypeptide, and the composition can comprise, or consist essentially of, an AAV9 vector in combination with a pharmaceutically acceptable delivery vehicle. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide. The mammal can be a human.

In another aspect, this document features a method for prolonging survival time for a mammal with hypertensive heart disease. The method comprises, or consists essentially of, administering a vector or a composition to the mammal. The vector can be an AAV9 vector comprising, or consisting essentially of, a nucleic acid sequence encoding a natriuretic polypeptide, and the composition can comprise, or consist essentially of, an AAV9 vector in combination with a pharmaceutically acceptable delivery vehicle. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide. The mammal can be a human.

In another aspect, this document features a method for improving cardiac function in a mammal with hypertensive heart disease. The method comprises, or consists essentially of, administering a vector or a composition to the mammal under conditions wherein cardiac function is improved at least five months following the administration. For example, cardiac function can be improved for a period of time extending from about five months following the administration to about twelve months following the administration, from about five months following the administration to about ten months following the administration, or from about five months following the administration to about six months following the administration). The vector can be an AAV9 vector comprising, or consisting essentially of, a nucleic acid sequence encoding a natriuretic polypeptide, and the composition can comprise, or consist essentially of, an AAV9 vector in combination with a pharmaceutically acceptable delivery vehicle. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide. The mammal can be a human.

In another aspect, this document features a method for improving cardiac function in a mammal with polycystic kidney disease. The method comprises, or consists essentially of, administering a vector or a composition to the mammal under conditions wherein cardiac function is improved at least two months following the administration. For example, cardiac function can be improved for a period of time extending from about two months following the administration to about twelve months following the administration, from about two months following the administration to about ten months following the administration, or from about two months following the administration to about five months following the administration). The vector can be an AAV9 vector comprising, or consisting essentially of, a nucleic acid sequence encoding a natriuretic polypeptide, and the composition can comprise, or consist essentially of, an AAV9 vector in combination with a pharmaceutically acceptable delivery vehicle. The natriuretic polypeptide can be a human BNP polypeptide. The natriuretic polypeptide can be a CDNP polypeptide. The natriuretic polypeptide can be a B-CDNP polypeptide. The natriuretic polypeptide can be a C-CDNP polypeptide. The mammal can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1. Generation of pre-proBNP-expressing AAV9 vector. (A) Schematic representation of the AAV9 vector encoding rat pre-proBNP. SD; splice donor, SA; splice acceptor, WPRE; woodchuck hepatitis virus post-transcriptional regulatory elements. CMV, Cytomegalovirus; SD, splice donor; SA, splice acceptor; WPRE, woodchuck hepatitis virus posttranscriptional regulatory element. (B) Verification of proBNP expression in 293T cells transfected with pAAV-r-proBNP. Immunoreactive BNPs in cell lysates and culture supernatants were detected by anti-rat BNP45 antibody. HMW, high molecular weight. (C) Immunostaining of rat BNP in pAAV-r-proBNP-transfected mouse cardiomyocytes (HL1 cells). When the plasmid encoding for the full length of pre-proBNP was introduced in HL1 cells, immunoreactive BNP signals were detected supra-nuclearly and in cytoplasmic secretory vesicles.

FIG. 3. Effects of long-term BNP overexpression in SHR. (A) No apparent toxicity observed in SHR at 4 months after proBNP-expressing AAV9 vector-administration. Toxicological and pharmacological parameters of the treated and untreated SHR were shown (n=4). No toxicity was observed in the rats, while plasma immunoreactive BNP45 was significantly elevated in the AAV9 vector-treated group. WBC, white blood cells; RBC, red blood cell; HGB, hemoglobin; HCT, hematocrit; PLT, platelets; ALB, albumin; ALP, alkaline phosphatase; ALT, alanine transferase; AMY, amylase; TBIL, total bilirubin; BUN, blood urea nitrogen; PHOS, phosphorus; CRE, creatinine; GLU, glucose; TP, total protein. (B) BP measurements of proBNP-expressing AAV9 vector-administered SHR. BP in treated and untreated SHR were measured by tail-cuff method (n=8). *P<0.05 vs respective untreated controls. (C) M-mode echocardiography of untreated and AAV9-proBNP treated SHR at four and nine months post AAV9 vector injection. AAV9 vector-treated SHR had significantly improved diastolic functions at four months and both diastolic and systolic functions at nine months as compared with untreated SHR. LVDs, left ventricular end-systolic dimension; LVDd, left ventricular end-diastolic dimension.

FIG. 4. Effects of long-term BNP overexpression on cardiac remodeling. (A) Intra-arterial measurements of heart rate (HR), systolic blood pressure (SBP), and diastolic blood pressure (DBP) in anesthetized, treated and untreated, SHR are indicated±SD. (B) Plasma immunoreactive BNP45, plasma cGMP, and urinary cGMP are shown (n=4). Error bars indicate±SD. *P<0.05 vs respective untreated controls. (C) Cross sections were stained by Mason's trichrome staining for muscle fibers (red staining) and collagen/fibrosis (blue staining). Representative images of whole section of treated and untreated SHR (upper panels) and higher magnifications of heart images of rats (n=4, lower panels) are shown. (D) Connective tissue deposition was evaluated as percent blue signals/red signals by KS400 Image Analysis software. The averages of four heart samples in treated and untreated SHR groups are shown.

FIG. 5. Effects of non-cardiac BNP overexpression in SHR. (A) Distribution of luciferase activities in firefly luciferase-expressing AAV2 vector-administered SHR organs was monitored by Xenogen Living Image. Strong luciferase expression was evident in peritoneum by AAV2 in SHR (left panel), while no detectable luciferase expression was observed in heart (right panels). (B) BP measurements of proBNP-expressing AAV2 and AAV9 vector-administered SHR. BP in AAV2-treated (n=5), AAV9-treated (n=3), and untreated SHR (n=5) were measured by tail-cuff method. Error bars indicate±SD. *P<0.05 vs respective untreated controls. (C) Plasma immunoreactive BNP45 and the heart weight/body weight ratios are shown. Error bars indicate±SD. *P<0.05 vs respective untreated controls.

FIG. 6. Effects of AAV9 vector-mediated long-term BNP expression in normal Wistar rats. (A) Efficient cardiac transgene expression upon systemic AAV9 vector-administration. Normal rats were injected by GFP-carrying AAV9 vector. Four weeks after injection, heart sections were analyzed for GFP expression. (B) Plasma immunoreactive BNP and the heart weight/body weight ratios are shown. Error bars indicate±SD. *P<0.05 vs respective untreated controls. (C) Intra-arterial measurements of heart rate (HR), systolic blood pressure (SBP), and diastolic blood pressure (DBP) in anesthetized, treated and untreated, SHR are indicated±SD.

FIG. 11 is a table demonstrating that sustained cardiac proBNP over-expression by the AAV9 vector improved cardiac function and structure in mammals with established hypertensive heart disease.

FIG. 13 is a table demonstrating that sustained cardiac proBNP over-expression by the AAV9 vector improved cardiac function and structure in mammals with polycystic kidney disease.

FIG. 14 contains amino acid sequences for ANP, pre-pro-ANP (SEQ ID NO:13), mANP, and pre-pro-mANP (SEQ ID NO:14) as well as a codon optimized nucleic acid sequence that encodes pre-pro-mANP (SEQ ID NO:15).

DETAILED DESCRIPTION

This document provides methods and materials for treating cardiovascular and/or renal diseases. For example, this document provides AAV9 vectors designed to express natriuretic polypeptides, nucleic acid molecules encoding natriuretic polypeptides, methods for making AAV9 vectors, and methods for using such vectors or molecules to treat cardiovascular and/or renal diseases. In some cases, an AAV8 vector can be used in place of an AAV9 vector described herein to obtain an AAV8 vector designed to express one or more natriuretic polypeptides. Such AAV8 vectors can be uses as described herein with respect to AAV9 vectors.

As described herein, an AAV9 vector can be configured to include a nucleic acid sequence that encodes a natriuretic polypeptide. Examples of natriuretic polypeptides that can be expressed using an AAV9 vector as described herein include, without limitation, ANP (e.g., human ANP), BNP (e.g., human BNP), CNP (e.g., human CNP), CDNP, DNP, mANP, and ASBNP. The core amino acid sequence of CDNP can be as follows: GLSKGCFGLKLDRIGSMSGL-GCPSLRDPRPNAPSTSA (SEQ ID NO:6). The amino acid sequence for ANP, pre-pro-ANP, mANP, and pre-pro-mANP can be as set forth in FIG. 14. In some cases, the nucleic acid sequence encoding a natriuretic polypeptide can be codon optimized. For example, a codon optimized nucleic acid sequence designed to encode pre-pro-mANP as set forth in FIG. 14 can be using to make an AAV9 or AAV8 vector provided herein.

In some cases, an AAV9 vector can be configured to include two or more different nucleic acid sequences that encode natriuretic polypeptides. For example, an AAV9 vector can be configured to include a nucleic acid sequence that encodes human BNP and a nucleic acid sequence that encodes CDNP.

In some cases, the one or more natriuretic polypeptides to be expressed using an AAV9 vector can include the N-terminal region of a natural natriuretic polypeptide that includes non-active components of an active natriuretic polypeptide such as a signal peptide sequence and other sequences that can be involved in polypeptide processing, folding, and stabilization. Examples of such N-terminal regions include, without limitation, those set forth in SEQ ID NO: 1, 4, or 5. In some cases, one or more of the following sequences can be used as an N-terminal region of a natriuretic polypeptide to be expressed using an AAV9 vector: BNP signal peptide+NT-proBNP, CNP signal peptide+NT-proCNP, and ANP signal peptide+NT-proANP. Examples of amino acid sequences encoding a natriuretic polypeptide that includes such an N-terminal region include, without limitation, those amino acid sequences set forth in SEQ ID NO: 3, 7, 8, or 13.

Figure 12:
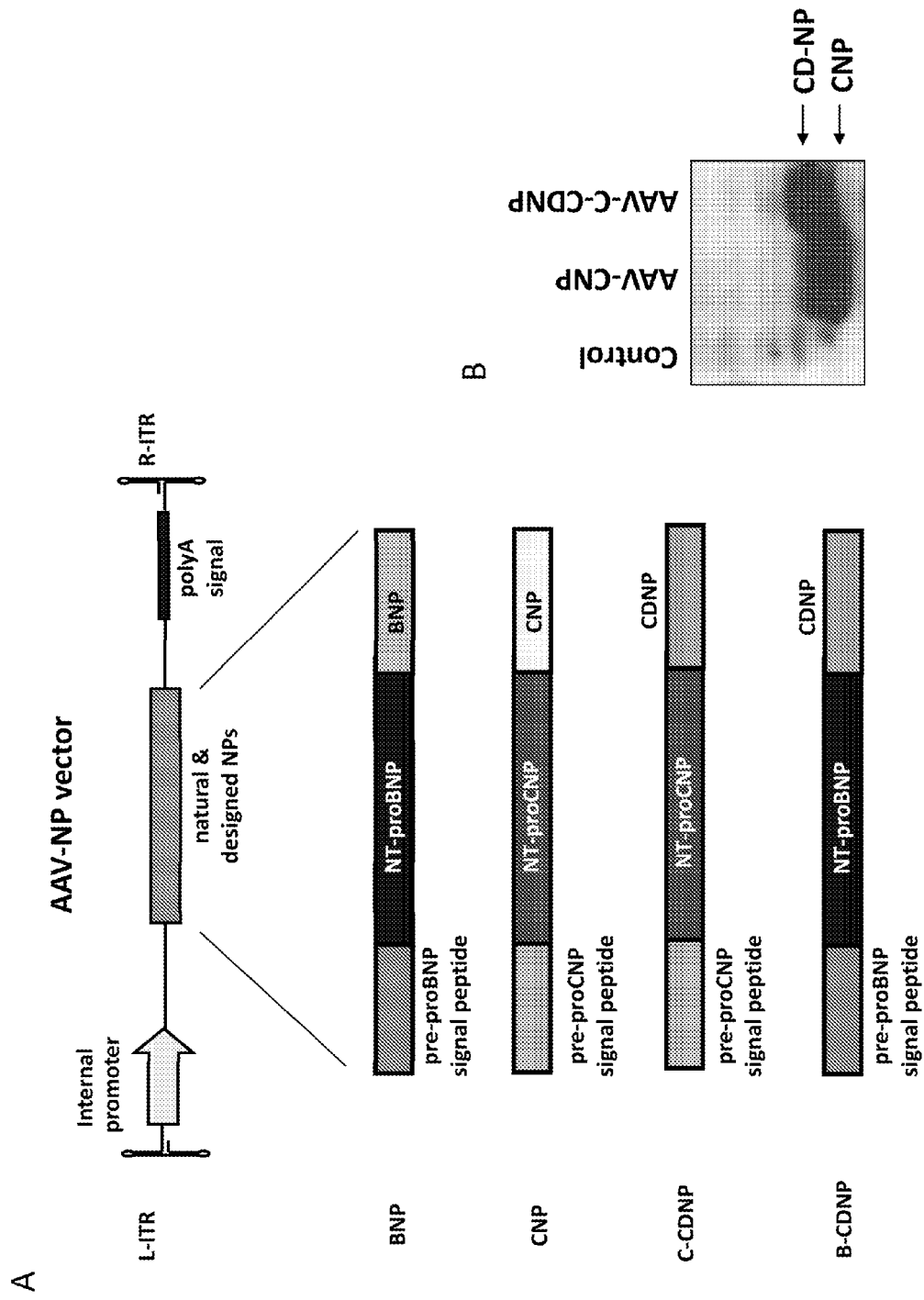
FIG. 12A contains schematics of various AAV vectors that can be designed to express the indicated natriuretic polypeptides.
FIG. 12B is a photograph of a Western blot analysis demonstrating the expression of CNP from an AAV9-CNP vector and the expression of CDNP from an AAV9-C-CDNP vector.

A nucleic acid sequence (e.g., a nucleic acid sequence optimized for human codon usage) encoding a natriuretic polypeptide described herein can be inserted into any appropriate AAV9 viral vector. For example, a nucleic acid sequence encoding a human CDNP can be inserted into an AAV9 vector having a nucleic acid sequence as set forth in GenBank® Accession No. AY530557 (GI No. 46487760), JA400113.1 (GI No. 346220229), JA232063 (GI No. 330731135), JA231827 (GI No. 330729561), or JA062576 (GI No. 328343515). In some cases, an AAV9 vector can have the sequence as described elsewhere. See, e.g., WO2003/052052, U.S. Patent Application Publication No. 20110236353, EP2345731, EP2292780, EP2292779, or EP2298926. In some cases, an AAV vector (e.g., AAV9 or AAV8 vectors) can be designed to express BNP, CNP, or CDNP as set forth in FIG. 12A.

In some cases, a promoter sequence can be operably linked to a nucleic acid sequence that encodes a natriuretic polypeptide (e.g., BNP, pre-proBNP, CDNP, B-CDNP, or C-CDNP) to drive expression of the natriuretic polypeptide. Examples of such promoter sequences include, without limitation, CMV, EF1alpha, BNP, CNP, ANP, MYH6, and MYH7 promoters. In some cases, a promoter sequence that is active under conditions of elevated blood pressure with minimal, or no, activity under conditions of normal or low blood pressure can be operably linked to a nucleic acid sequence that encodes a natriuretic polypeptide (e.g., BNP, pre-proBNP, CDNP, B-CDNP, or C-CDNP) to drive expression of the natriuretic polypeptide under conditions of elevated blood pressure. Examples of such blood pressure sensitive promoter sequences include, without limitation, BNP and ANP promoters.

In one aspect, this document provides AAV9 vectors containing a nucleic acid sequence that encodes a natriuretic polypeptide. Such AAV9 vectors can infect cardiac cells and direct the expression of the natriuretic polypeptide by the infected cells.

Any appropriate method can be used to insert nucleic acid (e.g., nucleic acid encoding a natriuretic polypeptide) into the genome of an AAV9 vector. For example, standard molecule biology techniques such as restriction enzyme cutting, ligations, and homologous recombination can be used to insert nucleic acid into the genome of an AAV9 vector. Any appropriate method can be used to identify AAV9 vectors containing a nucleic acid molecule that encodes a natriuretic polypeptide. Such methods include, without limitation, PCR and nucleic acid hybridization techniques such as Northern and Southern analysis. In some cases, immunohistochemistry and biochemical techniques can be used to determine if an AAV9 vector contains a particular nucleic acid molecule by detecting the expression of a polypeptide encoded by that particular nucleic acid molecule.

In another aspect, this document provides nucleic acid molecules that encode a natriuretic polypeptide. For example, a nucleic acid molecule provided herein can be a single nucleic acid molecule that encodes the N-terminal region of a natural natriuretic polypeptide that includes one or more non-active components of an active natriuretic polypeptide such as a signal peptide sequence and other sequences that can be involved in polypeptide processing, folding, and stabilization upstream of an active component of a natriuretic polypeptide. In some cases, such a nucleic acid molecule can have a nucleic acid sequence that encodes a natriuretic polypeptide set forth in SEQ ID NO: 3, 7, 8, or 13.

In some cases, a nucleic acid molecule provided herein can include a promoter sequence operably linked to the nucleic acid sequence encoding a natriuretic polypeptide. For example, a nucleic acid molecule provided herein can include a promoter sequence that is active under conditions of elevated blood pressure operably linked to a nucleic acid sequence encoding a natriuretic polypeptide (e.g., CDNP).

The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

This document also provides methods for treating cardiovascular and/or renal diseases (e.g., to reduce blood pressure, cardiomyocyte hypertrophy, cardiac fibrosis, or renal fibrosis, or to improve systolic and diastolic dysfunctions). For example, an AAV9 vector provided herein can be administered to a mammal having a cardiovascular and/or renal disease to reduce blood pressure within the mammal.

An AAV9 vector provided herein can be produced in human cell lines, such as 293T cells, or other types of cells such as insect cells, which can be concentrated typically by at least 100-fold, or even by as much as 5,000- to 10,000-fold, through ultracentrifugation. A viral titer typically is assayed by measuring the viral vector copy numbers in concentrated/purified vector preparations.

An AAV9 vector provided herein can be administered to a patient (e.g., human patient) by, for example, direct injection into a group of cardiac cells or intravenous delivery to cardiac cells. An AAV9 vector provided herein can be administered to a patient in a biologically compatible solution or a pharmaceutically acceptable delivery vehicle such as saline, by administration either directly into a group of cardiac cells or systemically (e.g., intravenously). Suitable pharmaceutical formulations depend in part upon the use and the route of entry. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient, an effective dose can be determined by setting as a lower limit the concentration of virus proven to be safe and escalating to higher doses of up to $10^{13}$ vector genome copies (vg)/kg, while monitoring for a response (e.g., a reduction in blood pressure) along with the presence of any deleterious side effects. Escalating dose studies can be used to obtain a desired effect for a given viral treatment.

An AAV9 vector provided herein can be delivered in a dose ranging from, for example, about $10^3$ vg/kg to about $10^{13}$ vg/kg. A therapeutically effective dose can be provided in repeated doses. Repeat dosing is appropriate in cases in which observations of clinical symptoms or monitoring assays indicate that the degree of viral activity (e.g., natriuretic polypeptide expression) is declining. Repeat doses can be administered by the same route as initially used or by another route. A therapeutically effective dose can be delivered in several discrete doses (e.g., days, weeks, months, or years apart).

An AAV9 vector provided herein can be directly administered to cardiac cells. For example, a virus can be injected directly into heart tissue. In some cases, ultrasound guidance can be used in such a method. In some cases, an AAV9 vector provided herein can be delivered systemically. For example, systemic delivery can be achieved intravenously via injection. The course of therapy with an AAV9 vector provided herein can be monitored by evaluating changes in clinical symptoms.

The invention will be further described in the following examples, which do not limit the scope of the invention described in the claims.

EXAMPLES

Example 1

Long-Term Cardiac proBNP Gene Delivery Prevents the Development of Hypertensive Heart Disease in Spontaneously Hypertensive Rats SHR and Wistar Rats Four week-old SHR and five week-old Wistar rats were purchased from Charles River. SHR served as a model of progressive HHD. Strains of rats, number of animals, treatment, and duration of treatment in each experiment was summarized in Table 1. All animal studies were approved by the Institutional Animal Care and Use Committee.

TABLE 1

Summary of the rats used.

| Study | Strain | Treatment | Number | Duration (weeks) |
|---|---|---|---|---|
| Cardiac delivery | SHR | AAV9-Luc | 2 | 3 |
| Toxicology | SHR | Untreated | 3 | 3 |
|  | SHR | AAV9-Luc | 3 | 3 |
|  | SHR | AAV9-BNP | 3 | 3 |
| Pharmacokinetics/dynamics | SHR | Untreated | 8 | 40 |
|  | SHR | AAV9-BNP | 8 | 40 |
| Non-cardiac delivery | SHR | Untreated | 5 | 8 |
|  | SHR | AAV2-BNP | 5 | 8 |
|  | SHR | AAV9-BNP | 3 | 8 |
| Normotensive rat study | Wistar | AAV9-GFP | 6 | 4 |
|  | Wistar | AAV9-BNP | 6 | 4 |

SHR, spontaneously hypertensive rats;
Luc, luciferase;
GFP, green fluorescent protein.

Cell Culture

HEK 293T cells were maintained in Dulbecco's modified Eagle's medium supplemented with 10% calf serum, 50 U/mL penicillin, and 50 µg/mL streptomycin. A murine atrial cardiomyocyte cell line, HL-11, was obtained from Dr. William C. Claycomb (Louisiana State University Medical Center, New Orleans) and cultured in Claycomb's medium with 10% FBS, 100 µM norepinephrine, and 4 mM L-glutamine on 0.02% gelatin/fibronectin-coated flasks or plates.

Transfection, Immunoblotting and Immunostaining

Fugene6 (Roche) was used for transfection. For immunoblotting, immuno-reactive rat BNPs were detected using rabbit anti-rat BNP1-45 antibody (AssayPro) and HRP-conjugated anti-rabbit IgG antibody. Immunostaining of immuno-reactive rat BNP was performed using the same anti-rat BNP1-45 antibody and FITC-conjugated anti-rabbit IgG antibody.

IVIS Imaging

The cardiac luciferase expression was monitored by Xenogen IVIS biophotonic imaging machine. Upon luciferin administration through IP, anesthetized rats were euthanized, and the organs were harvested immediately. Harvested tissues were placed on the 10-cm plates on the imaging chamber, and a background photo of the tissues and a color overlay of the emitted photon data were obtained.

Toxicological and Pharmacological Tests

For toxicological and pharmacological tests, hematological parameters (VetScan HM2 Hematology System; 50 µL blood in EDTA for WBC counts, WBC histogram, Hb, Hct, MCV, MCH, MCHC, RDW, graphic RBC histogram, PLT count, MPV, PCT, PDW and Graphic platelet histogram) and chemistry (VetScan Classic; 100 µL blood in lithium heparin; ALB, ALP, ALT, AMY, BUN, CA++, CRE, GLOB, GLU, K+, Na+, PHOS, TBIL, TP) were measured.

Plasmids

The codon-optimized rat pre-proBNP was synthesized by GenScript, and cloned into a lentiviral vector, pSIN-CSGWd1NotI. The BamHI-XhoI short fragment, which contained rat pre-proBNP and WPRE post-transcriptional regulatory element, was then cloned into the mammalian expression plasmid, pAAV-MCS (Stratagene), resulting in pAAV-rat-pre-proBNP.

AAV9 and AAV2 Vectors

The AAV9 vector stocks were produced in human 293T cells using the helper-free transfection method according to the manufacturer's protocol (Stratagene). For AAV9 vector production, AAV9 capsid-expressing plasmid pRep2Cap9 (obtained from Dr. Hiroyuki Nakai) was used, while AAV2 vector was made with the AAV2 capsid-expressing plasmid, pAAV-RC (Stratagene). Firefly luciferase-, humanized recombinant green fluorescent protein (GFP)-, or rat proBNP-encoding AAV genome constructs were packaged. Three days after transfection, AAV9 vector-producing 293T cells were harvested for vector purification. The cells were lysed by freeze and thaw cycling, followed by ultracentrifuge concentration (62,500 rpm for 2 hours) through Optiprep Density Gradient Medium (Sigma). The resulting AAV9 vectors were desalted and further concentrated using Amicon Ultra-15 100 k filtration (Amicon). The titers (genomic copy numbers/mL) of concentrated AAV9 vector stocks were determined by quantitative PCR using plasmid DNA standards, AAV genomic sequence-specific primers, and a fluorescent probe.

Non-Invasive Tail Blood Pressure Measurement

The blood pressure (BP) of conscious rats was measured by the CODA High-Throughput Non-Invasive Tail BP System (Kent Scientific).

Echocardiography (ECHO) for Non-Invasive Assessment of Ventricular Function and Structure To evaluate cardiac function and structure, both standard ECHO and Two-Dimensional Speckle-Derived Strain ECHO (2DSE) examinations were performed at four and nine months post injections in the BNP-treated and the untreated SHR. Standard ECHO and 2DSE also were performed in normal Wistar rats at 4 weeks after AAV9 injections. All ECHO examinations were performed by a skilled sonographer blinded to the treatment.

Standard ECHO was performed as follows. After removing chest hair, ultrasonic scans was performed in all rats in supine position using a Vivid 7 system (GE Healthcare, Milwaukee, Wis.) equipped with a 10S ultrasound probe (11.5 MHz) with ECG monitoring. M-mode images and gray scale 2D images (300-350 frames/sec) of the parasternal long-axis and mid-LV was recorded for off-line analysis. LV end-diastolic (LVDd) and end-systolic (LVDs) dimensions and septal diastolic (SWTd) and posterior wall diastolic (PWTd) and systolic (PWTs) thicknesses were measured from M-mode images. LV mass was calculated according to uncorrected cube assumptions as LV mass=$1.055 \times [(LVDd+SWTd+PWTd)^3-(LVDd)^3]$, where 1.055 is the specific gravity of myocardium. LV mass was corrected for body weight (LVMi) for analysis. End-systolic (ESV), end-diastolic and stroke volumes (SV), and ejection fraction (EF) was calculated using the Teichholz formula: LV volume=$7 \times [(LVDd)^3/(2.4+LVDd)]$. Relative wall thickness (RWT) was calculated as RWT=(SWTd+PWTd)/LVDd. All parameters represented the average of three beats.

2DSE was performed as follows. Using EchoPAC software (EchoPAC PC—2D strain, BTO 6.0.0, GE Healthcare, Milwaukee, Wis.), which included a high resolution speckle tracking analysis library for off-line analysis, endocardial border was carefully manually traced at end-systole in LV short-axis views at the middle level (i.e., at the level of papillary muscles). Ideal width of circular region of interest was chosen in order to include the entire myocardial wall. Speckle tracking was performed by the software and global strain, and circumferential strain rate parameters were measured computing the mean of the six middle LV segments. The analysis included peak circumferential systolic strains (sS) and strain rates (sSR) for evaluation of myocardial systolic function and peak early circumferential strain rates (dSR-E) for evaluation of myocardial diastolic function. All parameters represented the average of three beats. Using standard ECHO and 2DSE, significant improvement were detected in both systolic and diastolic function in a rat model of cardiac dysfunction when compared to the untreated SHR.

Acute Experiment Procedure

Rats for the acute protocol were anesthetized with isoflurane (1.5% in oxygen). Placement of PE-50 tubing into the carotid artery for BP monitoring and blood sampling were performed. A portion of the neck skin was removed, and the carotid artery were isolated and cleared. A cut was made with micro-scissors, and a PE-50 tubing was introduced into the vessel for direct BP monitoring. Blood was drawn to evaluate toxicological reactions in AAV9-BNP transduced rats and to measure BNP and cGMP. At the end of the experiments, rat organs were harvested for further analysis.

Masson's Trichrome Staining

The sections of frozen cardiac samples were assessed by Trichrome staining for collagen contents. Percent blue signals were analyzed by KS400 Image Analysis Software (version 3.0, Zeiss).

Sample Size and Statistical Analysis

Groups were compared by unpaired t-test, and changes within-groups were assessed by paired t-test. Comparisons of BP values between groups were performed by two-way ANOVA for repeated measurements. Data were expressed as mean±SD. Significance was accepted for $p<0.05$.

Results

In Vitro Expression and Localization of proBNP

After successfully engineering AAV9 encoding for the rat pre-proBNP, which included the signal peptide (SP), NT-proBNP, and BNP1-45 domains (FIG. 1A), the protein expression of BNP was verified in 293T cells. Non-glycosylated proBNP (10 kDa) and high molecular weight (HMW, 12-24 kDa) glycosylated proBNP were detected in the cell lysates by Western blotting analysis. Of note, HMW forms of BNP were predominantly secreted (FIG. 1B). When the pre-proBNP was expressed in mouse cardiomyocytes (HL-1 cells obtained from Dr. William C. Claycomb) and analyzed by immunostaining with an anti-rat BNP1-45 antibody, clear supranuclear localization of immunoreactive BNP (red staining) as well as discrete cytoplasmic body signals (red staining) were detected (FIG. 1C).

In Vivo Cardiac Specific Tropism of AAV9 Vector-Mediated Gene Transfer

Figure 2:
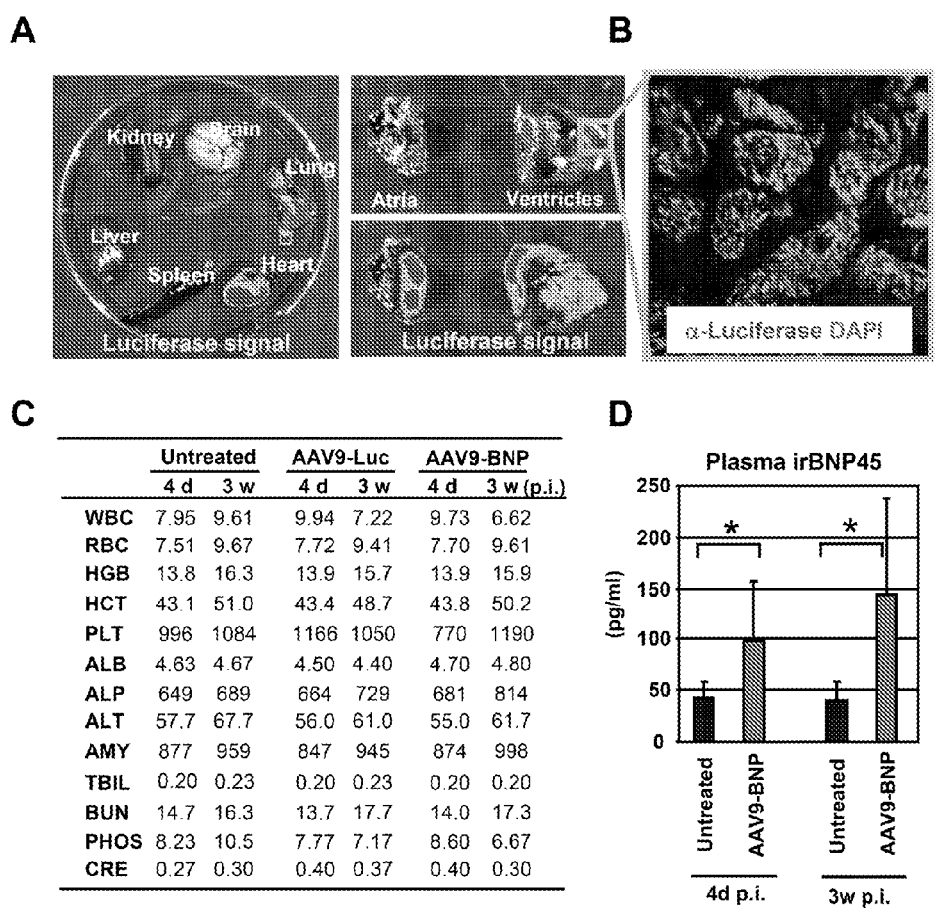
FIG. 2. AAV9 vector facilitates efficient cardiac gene delivery in spontaneously hypertensive rats (SHR). (A) Distribution of luciferase activities in firefly luciferase-expressing AAV9 vector-administered SHR organs was monitored by Xenogen IVIS Living Image. Strong luciferase expression in heart demonstrated efficient cardiac gene delivery by AAV9 in SHR (n=2) (left panel). Higher magnifications of Luciferase signals were found in both atria and ventricles (right panels). (B) Detection of luciferase by immunostaining Luciferase in the sections of heart ventricles were detected by anti-firefly luciferase antibody, confirming the efficient cardiac luciferase gene expression upon AAV9 vector-mediated gene transfer. (C) No apparent toxicity observed in AAV9 vector-administered SHR. Toxicological and pharmacological parameters in vector-injected SHR (n=3) were measured at 4 days and 3 weeks after vector administration. Averages of three rats were shown. *P<0.05 vs respective untreated controls. WBC, white blood cells; RBC, red blood cell; HGB, hemoglobin; HCT, hematocrit; PLT, platelets; ALB, albumin; ALP, alkaline phosphatase; ALT, alanine transferase; AMY, amylase; TBIL, total bilirubin; BUN, blood urea nitrogen; PHOS, phosphorus; CRE, creatinine. (D) Sustained BNP expression in the proBNP-expressing vector-administered rats (n=3). The levels of plasma immunoreactive BNP were measured at 4 days and 3 weeks after vector administration by the rat BNP45 ELISA. Error bars indicate±SD. *P<0.05 vs respective untreated controls.

The rat pre-proBNP- or firefly luciferase-expressing vectors were packaged in AAV9 capsid, and the influence of AAV9 vector-mediated gene delivery was examined in SHR. Four week-old SHR (n=2) were used. Three weeks after tail intravenous injection of AAV9 carrying luciferase ($10^{12}$ genome copy/animal), the tissue specificity of the AAV9 vector was determined by luciferase expression in the SHR, which demonstrated high levels of luciferase expression in myocardium (FIG. 2A-B). To confirm luciferase expression in the heart, the heart section was stained with anti-luciferase antibody, and the signals were detected predominately in the cardiomyocytes (FIG. 2B). When AAV9-luciferase (n=3) and AAV9-pre-proBNP (n=3) were injected and the acute (4 days) and chronic (3 weeks) toxicological responses were compared to those of the untreated SHR (n=3), no notable toxicity was observed among these three groups of rats (FIG. 2B). However, plasma BNP, by rat BNP1-45 ELISA, was significantly higher in the AAV9-pre-proBNP-treated SHR compared with untreated SHR both at four days and three weeks after injections (FIG. 2D), thus confirming the sustained BNP expression upon AAV9 vector-mediated gene delivery.

Effects of Sustained proBNP Expression in SHR

The effects of sustained proBNP expression in SHR through cardiac proBNP delivery by AAV9 vector were monitored. Four months after AAV9-pre-proBNP injections in SHR, there was no toxicological reaction compared to untreated SHR. Importantly, plasma immune reactive BNP was significantly higher in the AAV9-pre-proBNP-treated group compared with the untreated SHR (FIG. 3A). Tail cuff BP measurements indicated significant reduction in SBP, DBP, and MAP in the AAV9-pre-proBNP-treated SHR as compared with untreated SHR. Indeed, in the AAV9-pre-proBNP, SBP was significantly reduced one month after injection and followed by a reduction in both DBP and MAP at two months post-injection as compared with the untreated SHR. These reductions in SBP, DBP, and MAP in conscious rats remained throughout the nine month study (FIG. 3B).

Echocardiographic parameters in untreated SHR and in AAV9 pre-proBNP treated SHR were summarized in Table 2. While no difference was detected in HR between AAV9 pre-proBNP treated and untreated SHR both at four and nine months post injection, echo analysis indicated a significant improvement of diastolic function at four and nine months as well as systolic function at nine months post injection in AAV9 pre-proBNP treated SHR as compared with untreated SHR (FIG. 3C). Of note, EF, PWTd, LVDd, and dSR-E circumferential were improved, and LVMi was lower at nine months in the AAV9 pre-proBNP treated SHR even when compared to four months untreated SHR (Table 2).

TABLE 2

Echocardiographic parameters in untreated (n = 8) and BNP treated SHR (n = 8).

| | 4 Month p.i. | | 9 Months p.i. | |
|---|---|---|---|---|
| | Untreated | BNP Treated | Untreated | BNP Treated |
| HR | 403 ± 27.3 | 392 ± 22.3 | 381 ± 25.2 | 393 ± 13 |
| SWTd | 2.09 ± 0.1 | 1.86 ± 0.1* | 2.71 ± 0.1† | 2.17 ± 0.2*† |
| PWTd | 2.03 ± 0.1 | 1.86 ± 0.2* | 2.16 ± 0.3 | 1.87 ± 0.1*‡ |
| LVDd | 6.77 ± 0.2 | 6.71 ± 0.1 | 7.56 ± 0.6† | 7.57 ± 0.4†‡ |
| LVDs | 3.83 ± 0.4 | 3.47 ± 0.1* | 4.66 ± 0.6† | 3.96 ± 0.3*† |
| Ejection Fraction | 80 ± 4.1 | 85 ± 1.8* | 74 ± 4.5† | 83 ± 2.1*†‡ |
| LV Mass Index | 0.44 ± 0.01 | 0.4 ± 0.02* | 0.49 ± 0.01 | 0.4 ± 0.01*†‡ |
| sSR Circumferential | −4.6 ± 0.7 | −4.75 ± 0.6 | −3.74 ± 0.4† | −5.04 ± 0.4* |
| dSR-E Circumferential | 2.41 ± 0.8 | 4.07 ± 1.5* | 2.09 ± 0.8 | 3.25 ± 0.9*‡ |

TABLE 2-continued

Echocardiographic parameters in untreated (n = 8) and BNP treated SHR (n = 8).

|  | 4 Month p.i. | | 9 Months p.i. | |
|---|---|---|---|---|
|  | Untreated | BNP Treated | Untreated | BNP Treated |
| sSR-Radial | 7.17 ± 1.1 | 6.77 ± 0.8 | 6.34 ± 1.6 | 8.13 ± 1.9*† |
| dSR-E Radial | −3.29 ± 1.2 | −5.72 ± 2.5* | −2.41 ± 1.3 | −4.57 ± 2.1*† |

*$P < 0.05$ vs respective Untreated;
†$P < 0.05$ vs four months within group;
‡$P < 0.05$ between nine months BNP-treated and four months Untreated.
HR, heart rate;
SWTd, septal wall thickness at end diastole;
PWTd, posterior wall thickness at end diastole;
LVDd, left ventricular end-diastolic dimension;
LVDs, left ventricular end-systolic dimension;
sSR, systolic strain rate;
dSR, diastolic strain rate.

At nine months post-injection, four rats per group were sacrificed for acute experiments. Direct intra-carotid systolic and diastolic blood pressure was reduced in the AAV9 pre-proBNP treated anesthetized SHR (FIG. 4A), while no significant differences were found in weights and heart rates between treated and untreated rats. The heart weight corrected for the body weight was significantly reduced in the BNP-treated as compared with the control SHR (0.37±0.01 vs 0.43±0.02, respectively, $p<0.05$). Plasma BNP was higher in the BNP-treated as compared with the control SHR (FIG. 4B). Although plasma cGMP was not different, urinary cGMP was greater in the BNP-treated as compared with the control SHR (FIG. 4B). Connective tissue (assessed by Mason's trichrome staining) tended to increase in heart sections of untreated SHR as compared with AAV9-preproBNP treated SHR (FIG. 4C-D).

Non-Cardiac BNP-Transduction by AAV2 Vector

The effects of non-cardiac proBNP gene delivery on BP, plasma BNP levels, and heart weight in SHR were assessed. For non-cardiac gene delivery, conventional AAV2 vectors were administered through intra-peritoneal injection. One month after administration of AAV2 vector carrying luciferase, high levels of luciferase expression were found in peritoneum, but not in heart (FIG. 5A), confirming efficient, but non-cardiac, gene delivery by AAV2 vector. To assess the influence of non-cardiac proBNP gene delivery, SHR were injected with pre-proBNP-carrying AAV2 vector and compared with untreated (n=5) and AAV9-pre-proBNP vector-administered rats (n=3). Tail cuff BP measurements indicated that AAV2-pre-proBNP administration had no significant effects on SBP and DBP. In contrast, SBP was significantly reduced five and eight weeks after injection of the AAV9-pre-proBNP vector (FIG. 5B). The pre-proBNP gene delivery by AAV9, but not AAV2, showed significantly higher plasma level of BNP (FIG. 5C) and significant reduction in the heart weight/body weight ratio (FIG. 5C), suggesting the requirement of cardiac pre-proBNP delivery for efficient BNP release and the anti-hypertrophic effects of BNP in SHR.

Effects of Sustained proBNP Expression in Normotensive Rats

To investigate whether the beneficial effects on both cardiac structure and function observed in the BNP-treated SHR were mainly due to the sustained BP effects, AAV9 encoding for GFP or pre-proBNP was injected in normal Wistar rats (n=12). Six rats per group underwent echocardiographic examination 4 weeks after injections and were sacrificed for acute experiments thereafter. Normal rats treated with AAV9 carrying GFP (n=6) showed wide spread GFP expression in cardiomyocytes 4 weeks after injection, further confirming the cardiac transduction of the AAV9 vector (FIG. 6A). Echocardiographic examination by strain analysis demonstrated that at 4 weeks post injection, AAV9-pre-proBNP treated normal rats (n=6) had a significantly improved systolic function compared with AAV9-GFP as indicated by a thinner SWTd, and higher sSR circumferential, while LVMi was only slightly reduced (p=0.07, NS) (Table 3). AAV9-pre-proBNP treated normal rats had significantly higher plasma level of BNP compared to the GFP-control rats (FIG. 6B). Although direct intra-carotid BP measurement found similar SBP, DBP, and MAP between the two groups, the heart weight corrected for the body weight was significantly reduced in the BNP-treated as compared with the GFP-control rats (FIGS. 6B and 6C).

TABLE 3

Echocardiographic parameters in control (n = 6) and BNP treated (n = 6) normal rats.

|  | 4 Weeks p.i. | |
|---|---|---|
|  | Controls | BNP Treated |
| HR | 407 ± 27.2 | 408 ± 24.5 |
| SWTd | 2.03 ± 0.15 | 1.80 ± 0.11* |
| PWTd | 1.66 ± 0.09 | 1.77 ± 0.19 |
| LVDd | 7.0 ± 0.67 | 7.1 ± 0.53 |
| LVDs | 3.84 ± 0.67 | 3.94 ± 0.37 |
| Ejection Fraction | 83 ± 1.72 | 83 ± 4.17 |
| LV Mass Index | 0.35 ± 0.01 | 0.33 ± 0.01 |
| sSR Circumferential | −5.37 ± 0.5 | −6.54 ± 0.8* |
| dSR-E Circumferential | 5.09 ± 0.7 | 5.98 ± 1.0 |
| sSR-Radial | 7.63 ± 1.5 | 9.08 ± 1.7 |
| dSR-E Radial | −5.59 ± 1.3 | −7.84 ± 2.7 |

*$P < 0.05$ vs respective Controls.
HR, heart rate;
SWTd, septal wall thickness at end diastole;
PWTd, posterior wall thickness at end diastole;
LVDd, left ventricular end-diastolic dimension;
LVDs, left ventricular end-systolic dimension;
sSR, systolic strain rate;
dSR, diastolic strain rate.

These results demonstrate successful in vivo cardiomyocyte transduction via a AAV9 vector that facilitated sustained cardiac proBNP overexpression. Long-term proBNP delivery led to reduced BP and improved LV function and structure in an HHD rat model without any short- or long-term toxicological adverse effects or development of tolerance. Although long-term proBNP delivery improved both systolic and diastolic function, the effect on diastolic performance was more remarkable and preceded the improvement in systolic function in this HHD model. Importantly, the effects on cardiac structure and function occurred independently of BP lowering effects in normal Wistar rats.

These results also demonstrated that rat BNP is released from pre-proBNP-expressing 293T cells as a HMW form.

In addition, rat proBNP overexpression was associated with significant and sustained BP reduction in SHR. Indeed, SBP, DBP and MAP were lower in the BNP-treated as compared with the control SHR from two months up to nine months post-AAV9 injection. This reduction of BP was rather modest and occurred without changes in HR. Of note, BP was reduced at the vector dose used in the current study, while it did not completely normalized BP, which remained elevated throughout the period of observation. It is possible that a higher vector dose would result in a more profound BP reduction. Although the use of telemetry would have helped in better assessing BP changes, a significant BP lowering effect of BNP was confirmed in unconscious BNP-treated SHR compared to the untreated SHR via direct intra-arterial BP measurements at the time of the acute experiments (9 months).

Plasma immunoreactive rat BNP45 was elevated in the BNP-treated as compared with the control SHR at four days, three weeks, and four and nine months post-injection, confirming a sustained overexpression of BNP in the heart. At nine months post-injection, plasma cGMP was not different between the BNP-treated and the control SHR. In contrast, urinary cGMP was increased in the BNP-treated as compared with the control SHR. Thus, the lack of elevation of plasma cGMP may be explained by the increased urinary cGMP excretion.

Chronic overexpression of proBNP prevented the development of HHD, which began at four weeks of age in the SHR. Indeed, AAV9 induced proBNP production resulted in a sustained and significant reduction (up to nine months) of SBP and DBP. Thorough echo analysis demonstrated a significant improvement of diastolic function at four months post transfection in the BNP-treated group as compared with the untreated SHR. Importantly, at nine months, untreated SHR also developed signs of impaired systolic function which was prevented in the BNP-treated SHR. Of note, global cardiac function and remodeling were not only improved in the BNP-treated SHR compared to untreated SHR of the same age but also, BNP-treated SHR at nine months showed improved diastolic function and reduced cardiac hypertrophy even when compared with the untreated SHR at four months of age. This finding further supports the beneficial role of BNP in preventing cardiac dysfunction and remodeling. Of note, all these favorable actions occurred without signs of any short- or long-term toxicological side effects and BNP maintained its biological actions up to nine months post injection without developing tolerance. It should be noted that, although sustained, the BP reduction was minimal, thus further studies are required to address the pathogenic role of BNP in hypertension.

In SHR transduced with non-cardiac AAV2 vector, no increase in plasma immunoreactive BNP was observed. This could be due to a less efficient intracellular processing and/or release of rat BNP in non-cardiac cells. Furthermore, in these AAV2-transduced SHR, changes in heart weight compared to untreated controls were not observed. The work described herein used a comparable vector dose for both the AAV2 and AAV9 studies.

The work was extended to normal rats to investigate the anti-hypertrophic actions of BNP overexpression in the absence of hypertension. In this model, age induced systolic impairment was significantly ameliorated in the BNP-treated rats by echo strain analysis at 4 weeks. Also, cardiac mass was reduced in the BNP-treated rats as compared with the controls and heart weight/body weight was significantly lower in the BNP-treated rats as compare to the controls. Importantly, the improved cardiac function and the reduced cardiac mass were observed after 4 weeks post injections of the AAV9 vector and occurred despite any difference in BP (measured directly intra-carotid) between the BNP-treated and the control group.

Taken together, the results provided herein demonstrate that the use of chronic supplementation of the cardiorenal protective hormone BNP can be employed in hypertension to prevent the progression toward more severe stages of HHD and the onset of heart and renal failure. Instead of oral delivery, a gene transfection strategy was used to facilitate a nine month delivery of bioactive BNP with single intravenous injection of the AAV9 vector. As indicated herein, chronic overexpression of BNP in SHR reduced BP, decreased LVH, tended to reduce fibrosis, and improved systolic and diastolic function.

In summary, the results provided herein demonstrate the successful cardiac delivery of the AAV9 vector, which mediated sustained cardiac proBNP overexpression without any short- or long-term toxicological effects and any signs of tolerance. Importantly, sustained cardiac BNP overexpression reduced BP and improved LV function in a model of progressive HHD after a single intravenous injection. Although long-term proBNP delivery improved both systolic and diastolic function, the effect on diastolic performance was more remarkable and appeared earlier during the development of HHD. Ultimately, sustained overexpression of BNP in SHR prevented the development of HHD as nine month old BNP-treated SHR had a significantly improved cardiac function and structure even when compared with four month old untreated SHR. Non-cardiac BNP-overexpression was not associated with increase in plasma BNP, changes in BP, and reduced heart weight. The direct cardiac effects of overexpressed BNP seem to be, at least in part, independent of BP lowering action as indicated by the improved systolic function and reduced heart weight in the normotensives rats despite no changes in BP.

Figure 9:
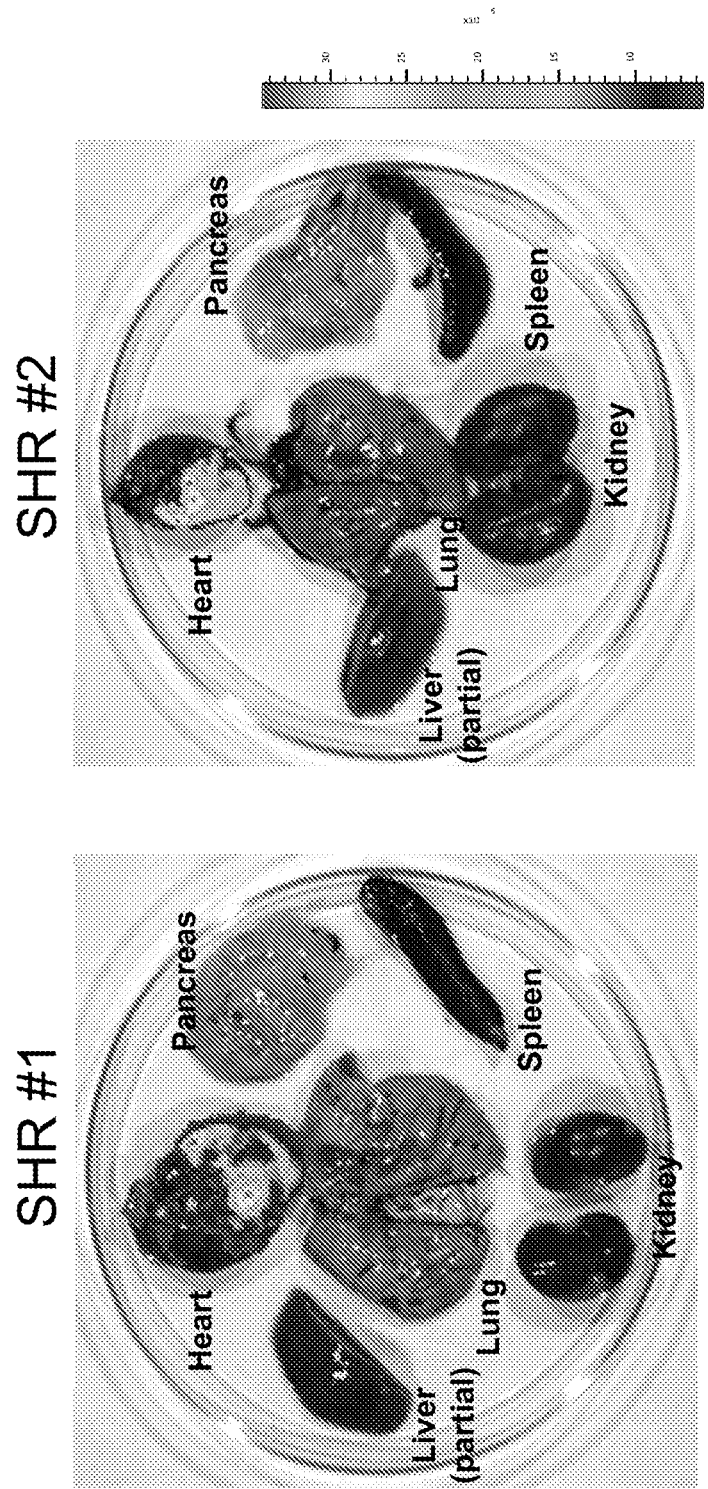
FIG. 9 contains photographs of tissues from spontaneously hypertensive rats 18 months after being exposed to an AAV9 vector designed to express luciferase. The tissues were assessed for luciferase activity. In both cases, the heart tissue exhibited high levels of luciferase activity.

In addition, an AAV9 vector designed to express luciferase achieved long-term cardiac luciferase expression in SHR rats at least for 18 months (FIG. 9). Generation of AAV9 vectors expressing CNP and CDNP as set forth in FIG. 12A was verified by Western blotting (FIG. 12B) using an anti-CNP antibody.

Example 2

Use of Natriuretic Polypeptides to Reduce Heart Volume

To deliver rat BNP-45 to rat cardiac cells, a cardio-tropic AAV9 vector was designed to express a rat proBNP polypeptide having a rat N-terminus proBNP amino acid sequence (called an NT-proBNP region) upstream of a rat BNP-45 amino acid sequence. The amino acid sequence for the rat NT-proBNP region with its signal peptide of the rat proBNP polypeptide was MDLQKVLPQMILLLLFLNL-SPLGGHSHPLG-SPSQSPEQSTMQKLLELIREK-SEEMAQRQLSKDQGPTKELLKRVLR (SEQ ID NO:1). The amino acid sequence for the rat BNP-45 of the rat proBNP polypeptide was SQDSAFRIQERLRNSK-MAHSSSCFGQKIDRIGAVSRLGCDGLRLF (SEQ ID NO:2). The amino acid sequence for the rat pre-proBNP polypeptide was MDLQKVLPQMI-LLLLFLNLSPLGGH-SHPLGSPSQSPEQSTMQKLLELIREKSEEMAQRQL-SKDQGPT KELLKRVLRSQDSAFRIQERLRNSK-MAHSSSCFGQKIDRIGAVSRLGCDGLRLF (SEQ ID NO:3).

To deliver CDNP to rat cardiac cells, two cardio-tropic AAV9 vectors were designed. One AAV9 vector was designed to express a polypeptide designated B-CDNP, and the other AAV9 vector was designed to express a polypeptide designated C-CDNP. The B-CDNP polypeptide included a human N-terminus proBNP amino acid sequence (called an NT-proBNP region) upstream of the CDNP amino acid sequence, while the C-CDNP polypeptide included a human N-terminus proCNP amino acid sequence (called an NT-proCNP region) with its signal peptide upstream of the CDNP amino acid sequence. The amino acid sequence for human NT-proBNP region with its signal peptide of the B-CDNP polypeptide was with its signal peptide MDPQTAPSRALLLLLFL-HLAFLGGRSHPLGSPGSAS-DLETSGLQEQRNHLQGKLSELQVEQTSLEPLQESPRP TGVWKSREVATEGIRGHRKMVLYTLRAPR (SEQ ID NO:4), and the amino acid sequence for the rat NT-proCNP region with its signal peptide of the C-CDNP polypeptide was MHLSQLLACALLLTLLSLRPSEAKPGAPPKVPRT-PPAEELAEPQ-AAGGGGKKGDKAPGGGANLK-GDRSRLLRDLRVDTKSRAAWARLLGEHPNAR KYK-GANKK (SEQ ID NO:5). The amino acid sequence for CDNP of the B-CDNP and C-CDNP polypeptides was GLSKGCFGLKLDRIGSMSGLGCPSLRDPRPNAPSTSA (SEQ ID NO:6). The amino acid sequence for B-CDNP polypeptide was MDPQTAPS-RALLLLLFLHLAFLGGR-SHPLGSPGSASDLETSGLQEQRNHLQG-KLSELQVEQTSL EPLQESPRPTGVWKSREVATEGIR-GHRKMVLYTLRAPRGLSKGCFGLKLDRIGSM SGLGCPSLRDPRPNAPSTSA (SEQ ID NO:7), and the amino acid sequence for C-CDNP polypeptide was MHLSQLLACALLLTLLSLRPSEAKPGAPPKVPRTP-PAE-ELAEPQAAGGGQKKGDKAPGGGANLK-GDRSRLLRDLRVDTKSRAAWARLLQ EHPNARKYK-GANKKGLSKGCFGLKLDRIGSMSGLGCPSLRDPRP-NAPSTSA (SEQ ID NO:8).

The nucleic acid sequences encoding B-CDNP and C-CDNP were codon-optimized for expression in human cells. The nucleic acid sequence encoding B-CDNP was as follows 5'-ATGGACCCACAGACAGCTCCCAG-TAGGGCTTTGCTTCTT-TTGCTTTTCCTGCACCTG-GCTTTTCTGGGCGGACGATCCCATCCACTGGGTAG CCCTGGCTCCGCCTCAGATCTGGAGACTAGTG-GACTGCAGGAGCAGCGCAAT CACTTGCA-GGGCAAACTGTCCGAGCTGCAGGTGGAACAAAC-GAGCCTCGAGC CCCTGCAGGAGAGCCCTAGACCTACCGGGGTGTG-GAAGTCTCGAGAGGTAGC GACAGAAGGCATTA-GAGGGCACAGGAAGATGGTACTGTATACTCT-GAGGGCC CCAAGGGGACTGAGCAAGGGCTGTTTTGGCCT-GAAGCTGGATCGGATTGGCA GCATGTCCGGC-CTGGGCTGCCCTTCCCTGCGGGACCCACGGC-CAAATGCCCCC TCCACCAGCGCCTAA-3' (SEQ ID NO:9), while the nucleic acid sequence encoding C-CDNP was as follows 5'-ATGCATCTGTCCCAACTGCTGGCTT-GTGCTCTCC-TGCTGACTCTGCTGAGCCTCCGGC-CTAGCGAGGCCAAGCCTGGAGCACCACC TAAGGTCCCCAGGACTCCTCCAGCCGAAGAACTG-GCTGAGCCTCAGGCTGCC GGGGGCGGGCA-GAAGAAAGGAGACAAAGCCCCTG-GAGGGGGCGGGGCTAAT CTCAAGGGCGATAGGTCCAGACTGCTGAGGGATCT-GAGAGTGGACACAAAGT CCAGGGCCGC-CTGGGCACGGCTCCTGCAAGAGCAC-CCTAACGCTCGGAAGTA CAAAGGGGCCAATAAGAAGGGCCTCAG-CAAAGGCTGCTTTGGCCTGAAACTG GACAGAAT-TGGCTCCATGTCCGGCCTCGGCTGCCCTTCCCT-GCGGGACCCTCG GCCCAATGCCCCTTCCACTAGCGCTTAA-3'(SEQ ID NO: 10).

Figure 7:
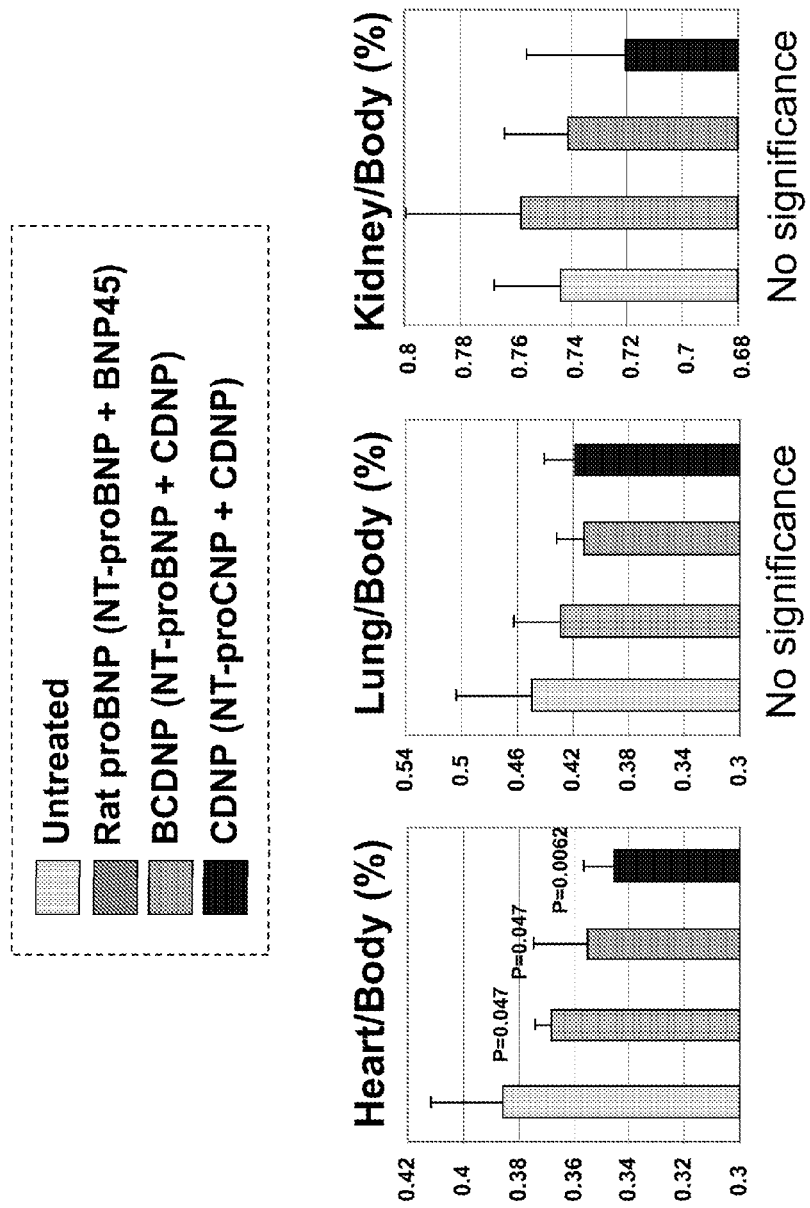
FIG. 7 contains graphs plotting heart, lung, or kidney weights as a percentage of body weight for untreated SHR or SHR treated with a AAV9 viral vector designed to express proBNP or proCDNP.
Figure 8:
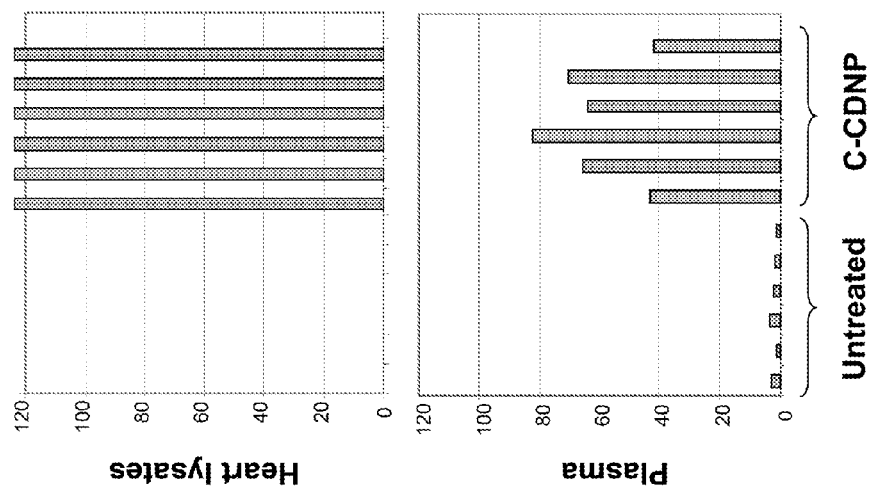
FIG. 8 contains graphs plotting the levels of CDNP in heart and circulation, which were measured by an ELISA kit detecting NT-proCNP.

Spontaneously hypertensive rats (SHR) were divided into groups of six rats each. One group included rats that were untreated, while the other groups were treated with a single intravenous injection of AAV9 vectors designed to express the rat proBNP polypeptide, the B-CDNP polypeptide, or the C-CDNP polypeptide. After five weeks, the rats were examined to determine the weights of their hearts, lungs, and kidneys. No significant difference was detected for the lungs and kidneys between the treated and untreated animals (FIG. 7). There, however, was a statistically significant difference in the weight of the hearts for the treated animals as compared to the weight of the hearts for the untreated animals (FIG. 7). Administration of AAV9-C-CDNP facilitated long-term cardiac CDNP expression for five weeks in six treated rats as compared to six untreated rats (FIG. 8).

These results demonstrate that a single intravenous administration of a natriuretic polypeptide-carrying AAV9 vector can protect the heart from excessive fibrosis and hypertrophy in mammals with hypertension and/or with renal dysfunction. These results also demonstrate that the methods and materials provided herein can be used for long-term natriuretic polypeptide treatment (e.g., long-term CNDP treatment) of patients with cardiovascular and/or renal diseases (e.g., those patients with severe cardiac hypertrophy and dysfunction).

Figure 10:
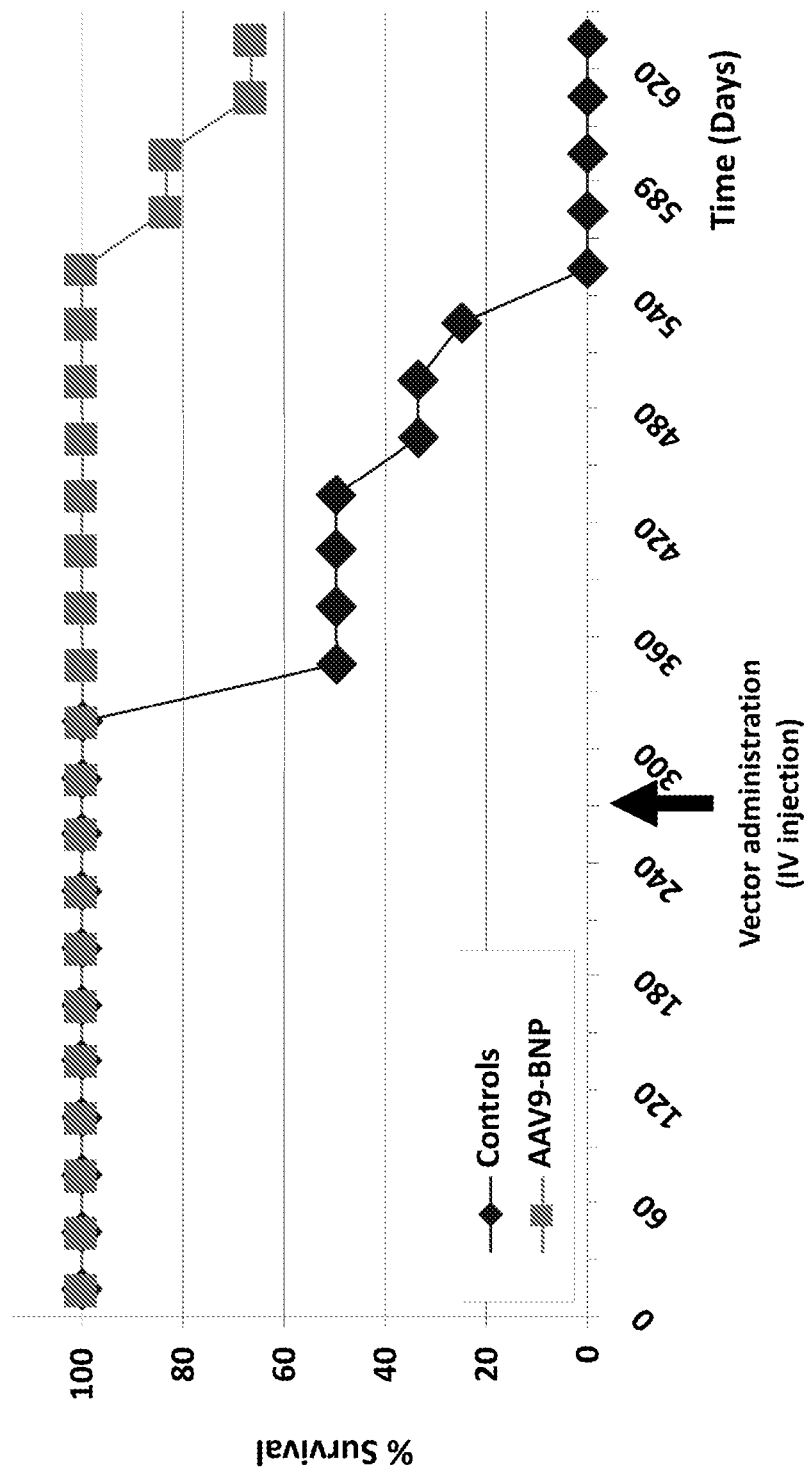
FIG. 10 is graph plotting percent survival of 9 month-old SHR rats with established hypertensive heart disease that were treated with an AAV9 vector designed to express BNP. Controls were comparable rats not treated with the AAV9 vector.

In another set of experiments, an AAV9 vector designed to express BNP was used to mediate cardiac BNP expression and extend the survival of rats with established hypertensive heart disease (FIG. 10). Briefly, 9 month-old SHR rats with established hypertensive heart disease were treated with the AAV9 vector expressing rat proBNP. Treated and untreated rats were monitored for survival. AAV9 vector-mediated cardiac BNP expression extended the survival of rats with established hypertensive heart disease (FIG. 10).

Sustained cardiac proBNP over-expression by the AAV9 vector improved cardiac function and structure in established hypertensive heart disease (FIG. 11). Aged SHR rats (9 months old) with impaired cardiac functions were randomly assigned to two groups, and 6 rats were intravenously injected with proBNP-expressing AAV9 vector ($1 \times 10^{12}$ genome particles/rat). The effects of sustained proBNP expression on cardiac functions/remodeling were analyzed at 5 months post injection. When compared to controls, septum wall thickness and LV mass were significantly reduced, while ejection fraction was significantly higher in BNP-treated rats (FIG. 11).

Expression of proBNP using an AAV9 vector designed to express proBNP resulted in improved cardiac functions in a rat model of polycystic kidney disease (FIG. 13). Short-term (2 months) AAV9-proBNP treatment significantly improved the cardiac function in a rat model of polycystic kidney disease (PKD). Briefly, four week old PCK rats (a rat model of PKD) were treated with the proBNP-encoding AAV9 vector. Two months after systemic vector administration, statistically significant improvements in cardiac structure and functions (output) were observed (FIG. 13).

Example 3

Design of BNP and CDNP Viral Vectors for Human Use to Treat Cardiovascular and/or Renal Diseases To deliver human BNP to human cardiac cells, a cardiotropic AAV9 vector was designed to express a human proBNP polypeptide having a human N-terminus proBNP amino acid sequence (called an NT-proBNP region) upstream of a human BNP-32 amino acid sequence. The amino acid sequence for the signal peptide and NT-proBNP region of the human proBNP polypeptide was MDPQTAPSRALLLLLFLHLAFLGGRSHPLG-SPGSAS-DLETSGLQEQRNHLQGKLSELQVEQTSLE-PLQESPRPTGVWKSREVATE GIRGHRKMVLYTL-RAPR (SEQ ID NO:4). The amino acid sequence for the human BNP-32 of the human proBNP polypeptide was SPKMVQGSGCFGRKMDRI-SSSSGLGCKVLRRH (SEQ ID NO:11). The amino acid sequence for the human proBNP polypeptide was MDPQTAPSRALLLLLFLHLAFLGGR-SHPLGSPG-SASDLETSGLQEQRNHLQG-KLSELQVEQTSLEPLQESPRPTGVWKSREVATEGIR GHRKMVLYTLRAPRSPKMVQGSGCFGRKM-DRISSSSGLGCKVLRRH (SEQ ID NO:12).

To deliver CDNP to human cardiac cells, two cardiotropic AAV9 vectors were designed. One AAV9 vector was designed to express a polypeptide designated human B-CDNP, and the other AAV9 vector was designed to express a polypeptide designated human C-CDNP. The human B-CDNP polypeptide was designed to include a human N-terminus proBNP amino acid sequence (called an NT-proBNP region) upstream of the CDNP amino acid sequence, while the C-CDNP polypeptide was designed to include a human N-terminus proCNP amino acid sequence (called an NT-proCNP region) upstream of the CDNP amino acid sequence. The amino acid sequence for the human NT-proBNP region with signal peptide of the human B-CDNP polypeptide was MDPQTAPSRA-LLLLLFL-HLAFLGGRSHPLGSPGSASDLETSGLQEQRNHLQG-KLSELQVEQTSLEP LQESPRPTGVWKSREVATEGIR-GHRKMVLYTLRAPR (SEQ ID NO:4), and the amino acid sequence for the human NT-proCNP region of the human C-CDNP polypeptide was MHLSQLLACALLLTLLSL-RPSEAKPGAPPKVPRTPPAE-ELAEPQAAGGGGKK-GDKAPGGGGANLKGDRSRLLRDLRVDTK-SRAAWARLLG EHPNARKYKGANKK (SEQ ID NO:5). The amino acid sequence for CDNP of the human B-CDNP and human C-CDNP polypeptides was GLSKGCFGLKL-DRIGSMSGLGCPSLRDPRPNAPSTSA (SEQ ID NO:6). The amino acid sequence for human B-CDNP polypeptide was MDPQTAPSRALLLLLFLHLAFLGGRSHPLGS-PG-SASDLETSGLQEQRNHLQGKLSELQVEQTSLE-PLQESPRPTGVWKSREVATEG IRGHRKMVLYTL-RAPRGLSKGCFGLKLDRIGSMSGLGCPSLRDPRPN-APSTSA (SEQ ID NO:7), and the amino acid sequence for human C-CDNP polypeptide was MHLSQLLA-CALLLTLLSLRPSEAKPGAPPKVPRTPPAEELAE-PQAAGGGGQKKGDK APGGGGANLKGDRSRLLRDL-RVDTKSRAAWARLLQEHPNARKYKGANKKGLS KGCFGLKLDRIGSMSGLGCPSLRDPRPNAPSTSA (SEQ ID NO:8).

The nucleic acid sequences encoding human B-CDNP and human C-CDNP were codon-optimized for expression in human cells. The nucleic acid sequence encoding human B-CDNP was as follows 5'-ATGGACCCACAGACA-GCTCCCAGTAGGG-CTTTGCTTCTTTTGCTTTTCCT-GCACCTGGCTTTTCTGGGCGGACGATCCCATC CACTGGGTAGCCCTGGCTCCGCCTCAGATCTGGA-GACTAGTGGACTGCAGGA GCAGCGCAATCACTT-GCAGGGCAAACTGTCCGAGCTGCAGGTG-GAACAAACG AGCCTCGAGCCCCTGCAGGAGAG-CCCTAGACCTACCGGGGTGTGGAAGTCTC GAGAG-GTAGCGACAGAAGGCATTAGAGGGCACAG-GAAGATGGTACTGTATA CTCTGAGGGC-CCCAAGGGGACTGAGCAAGGGCTGTTTGGCCTG-AAGCTGGA TCGGATTGGCAGCATGTCCGGC-CTGGGCTGCCCTTCCCTGCGGGACCCACGGC CAAATGCCCCTCCACCAGCGCCTAA-3' (SEQ ID NO:9), while the nucleic acid sequence encoding human C-CDNP was as follows 5'-ATGCATCTGTCCCAA-CTGCTGGCTTGTGCTCTCCTGCTGACTCTGCT-GAGCCTCCGGCCTAGCGAGGC CAAGCCTGGA-GCACCACCTAAGGTCCCCAGGACTCCTCCAGC-CGAAGAACTG GCTGAGCCTCAGGCTGC-CGGGGGCGGGCAGAAGAAAGGAGACAAAGCCCCT GGAGGGGGCGGGGCTAATCTCAAGGGCGATAG-GTCCAGACTGCTGAGGGATC TGAGAGTGGACA-CAAAGTCCAGGGCCGCCTGGGCACGGCTCCTG-CAAGAGCA CCCTAACGCTCGGAAGTA-CAAAGGGGCCAATAAGAAGGGCCTCAGCAAAGG CTGCTTTGGCCTGAAACTGGACAGAATTGGCTC-CATGTCCGGCCTCGGCTGCC CTTCCCTGCGGGAC-CCTCGGCCCAATGCCCCTTCCACTAGCGCTTAA-3' (SEQ ID NO:10).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving cardiac function in a mammal with polycystic kidney disease, wherein said method comprises administering an AAV9 vector to said mammal with polycystic kidney disease,
   wherein said AAV9 vector comprises a nucleic acid sequence encoding a natriuretic polypeptide, and
   wherein cardiac function is improved at least two months following said administration when said AAV9 vector is administered to said mammal with polycystic kidney disease.

2. The method of claim 1, wherein said mammal is a human.

* * * * *

SEQUENCE LISTING

```
<160> NUMBER OF SEQ ID NOS: 15

<210> SEQ ID NO 1
<211> LENGTH: 76
<212> TYPE: PRT
<213> ORGANISM: Rattus norvegicus

<400> SEQUENCE: 1

Met Asp Leu Gln Lys Val Leu Pro Gln Met Ile Leu Leu Leu Leu Phe
```

```
                1               5                   10                  15
        Leu Asn Leu Ser Pro Leu Gly Gly His Ser His Pro Leu Gly Ser Pro
                        20                  25                  30

Ser Gln Ser Pro Glu Gln Ser Thr Met Gln Lys Leu Leu Glu Leu Ile
                        35                  40                  45

Arg Glu Lys Ser Glu Glu Met Ala Gln Arg Gln Leu Ser Lys Asp Gln
                        50                  55                  60

Gly Pro Thr Lys Glu Leu Leu Lys Arg Val Leu Arg
        65                      70                  75
```

<210> SEQ ID NO 2
<211> LENGTH: 45
<212> TYPE: PRT
<213> ORGANISM: Rattus norvegicus

<400> SEQUENCE: 2

```
        Ser Gln Asp Ser Ala Phe Arg Ile Gln Glu Arg Leu Arg Asn Ser Lys
        1               5                   10                  15

Met Ala His Ser Ser Cys Phe Gly Gln Lys Ile Asp Arg Ile Gly
                        20                  25                  30

Ala Val Ser Arg Leu Gly Cys Asp Gly Leu Arg Leu Phe
                        35                  40                  45
```

<210> SEQ ID NO 3
<211> LENGTH: 121
<212> TYPE: PRT
<213> ORGANISM: Rattus norvegicus

<400> SEQUENCE: 3

```
        Met Asp Leu Gln Lys Val Leu Pro Gln Met Ile Leu Leu Leu Leu Phe
        1               5                   10                  15

Leu Asn Leu Ser Pro Leu Gly Gly His Ser His Pro Leu Gly Ser Pro
                        20                  25                  30

Ser Gln Ser Pro Glu Gln Ser Thr Met Gln Lys Leu Leu Glu Leu Ile
                        35                  40                  45

Arg Glu Lys Ser Glu Glu Met Ala Gln Arg Gln Leu Ser Lys Asp Gln
                        50                  55                  60

Gly Pro Thr Lys Glu Leu Leu Lys Arg Val Leu Arg Ser Gln Asp Ser
        65                      70                  75                  80

Ala Phe Arg Ile Gln Glu Arg Leu Arg Asn Ser Lys Met Ala His Ser
                        85                  90                  95

Ser Ser Cys Phe Gly Lys Ile Asp Arg Ile Gly Ala Val Ser Arg
                        100                 105                 110

Leu Gly Cys Asp Gly Leu Arg Leu Phe
                        115                 120
```

<210> SEQ ID NO 4
<211> LENGTH: 102
<212> TYPE: PRT
<213> ORGANISM: Homo sapiens

<400> SEQUENCE: 4

```
        Met Asp Pro Gln Thr Ala Pro Ser Arg Ala Leu Leu Leu Leu Leu Phe
        1               5                   10                  15

Leu His Leu Ala Phe Leu Gly Gly Arg Ser His Pro Leu Gly Ser Pro
                        20                  25                  30

Gly Ser Ala Ser Asp Leu Glu Thr Ser Gly Leu Gln Glu Gln Arg Asn
                        35                  40                  45
```

-continued

His Leu Gln Gly Lys Leu Ser Glu Leu Gln Val Gln Thr Ser Leu
         50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg
            100

<210> SEQ ID NO 5
<211> LENGTH: 104
<212> TYPE: PRT
<213> ORGANISM: Rattus norvegicus

<400> SEQUENCE: 5

Met His Leu Ser Gln Leu Leu Ala Cys Ala Leu Leu Thr Leu Leu
 1               5                  10                  15

Ser Leu Arg Pro Ser Glu Ala Lys Pro Gly Ala Pro Lys Val Pro
                20                  25                  30

Arg Thr Pro Pro Ala Glu Glu Leu Ala Glu Pro Gln Ala Ala Gly Gly
                 35                  40                  45

Gly Gly Lys Lys Gly Asp Lys Ala Pro Gly Gly Gly Ala Asn Leu
 50                  55                  60

Lys Gly Asp Arg Ser Arg Leu Leu Arg Asp Leu Arg Val Asp Thr Lys
 65                  70                  75                  80

Ser Arg Ala Ala Trp Ala Arg Leu Leu Gly Glu His Pro Asn Ala Arg
                 85                  90                  95

Lys Tyr Lys Gly Ala Asn Lys Lys
            100

<210> SEQ ID NO 6
<211> LENGTH: 37
<212> TYPE: PRT
<213> ORGANISM: Artificial Sequence
<220> FEATURE:
<223> OTHER INFORMATION: chimeric peptide

<400> SEQUENCE: 6

Gly Leu Ser Lys Gly Cys Phe Gly Leu Lys Leu Asp Arg Ile Gly Ser
 1               5                  10                  15

Met Ser Gly Leu Gly Cys Pro Ser Leu Arg Asp Pro Arg Pro Asn Ala
                20                  25                  30

Pro Ser Thr Ser Ala
            35

<210> SEQ ID NO 7
<211> LENGTH: 139
<212> TYPE: PRT
<213> ORGANISM: Artificial Sequence
<220> FEATURE:
<223> OTHER INFORMATION: chimeric peptide

<400> SEQUENCE: 7

Met Asp Pro Gln Thr Ala Pro Ser Arg Ala Leu Leu Leu Leu Phe
 1               5                  10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
                 35                  40                  45

His Leu Gln Gly Lys Leu Ser Glu Leu Gln Val Gln Thr Ser Leu
         50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Gly Leu Ser Lys Gly Cys Phe Gly Leu Lys
             100                 105                 110

Leu Asp Arg Ile Gly Ser Met Ser Gly Leu Gly Cys Pro Ser Leu Arg
         115                 120                 125

Asp Pro Arg Pro Asn Ala Pro Ser Thr Ser Ala
         130                 135

<210> SEQ ID NO 8
<211> LENGTH: 141
<212> TYPE: PRT
<213> ORGANISM: Artificial Sequence
<220> FEATURE:
<223> OTHER INFORMATION: chimeric peptide

<400> SEQUENCE: 8

Met His Leu Ser Gln Leu Leu Ala Cys Ala Leu Leu Thr Leu Leu
 1               5                  10                  15

Ser Leu Arg Pro Ser Glu Ala Lys Pro Gly Ala Pro Pro Lys Val Pro
                 20                  25                  30

Arg Thr Pro Pro Ala Glu Glu Leu Ala Glu Pro Gln Ala Ala Gly Gly
             35                  40                  45

Gly Gln Lys Lys Gly Asp Lys Ala Pro Gly Gly Gly Ala Asn Leu
         50                  55                  60

Lys Gly Asp Arg Ser Arg Leu Leu Arg Asp Leu Arg Val Asp Thr Lys
 65                  70                  75                  80

Ser Arg Ala Ala Trp Ala Arg Leu Leu Gln Glu His Pro Asn Ala Arg
                 85                  90                  95

Lys Tyr Lys Gly Ala Asn Lys Lys Gly Leu Ser Lys Gly Cys Phe Gly
             100                 105                 110

Leu Lys Leu Asp Arg Ile Gly Ser Met Ser Gly Leu Gly Cys Pro Ser
         115                 120                 125

Leu Arg Asp Pro Arg Pro Asn Ala Pro Ser Thr Ser Ala
         130                 135                 140

<210> SEQ ID NO 9
<211> LENGTH: 420
<212> TYPE: DNA
<213> ORGANISM: Artificial Sequence
<220> FEATURE:
<223> OTHER INFORMATION: codon-optimized

<400> SEQUENCE: 9
atggacccac agacagctcc cagtagggct tgcttctttt gcttttcct gcacctggct      60 tttctgggcg acgatccca tccactgggt agccctggct ccgcctcaga tctggagact     120
agtggactgc aggagcagcg caatcacttg cagggcaaac tgtccgagct gcaggtggaa    180
caaacgagcc tcgagcccct gcaggagagc cctagaccta ccggggtgtg gaagtctcga    240
gaggtagcga cagaaggcat tagagggcac aggaagatgg tactgtatac tctgagggcc    300 ccaagggac tgagcaaggg ctgttttggc ctgaagctgg atcggattgg cagcatgtcc     360
ggcctgggct gcccttccct gcgggaccca cggccaaatg ccccctccac cagcgcctaa   420

<210> SEQ ID NO 10
<211> LENGTH: 426
<212> TYPE: DNA
<213> ORGANISM: Artificial Sequence
<220> FEATURE:
<223> OTHER INFORMATION: codon-optimized

<400> SEQUENCE: 10

```
atgcatctgt cccaactgct ggcttgtgct ctcctgctga ctctgctgag cctccggcct      60
agcgaggcca agcctggagc accacctaag gtccccagga ctcctccagc cgaagaactg     120
gctgagcctc aggctgccgg gggcgggcag aagaaaggag acaaagcccc tggagggggc     180
ggggctaatc tcaagggcga taggtccaga ctgctgaggg atctgagagt ggacacaaag     240
tccagggccg cctgggcacg gctcctgcaa gagcacccta cgctcggaa gtacaaaggg     300 gccaataaga agggcctcag caaaggctgc tttggcctga aactggacag aattggctcc     360
atgtccggcc tcggctgccc ttccctgcgg gaccctcggc ccaatgcccc ttccactagc     420
gcttaa                                                                426
```

<210> SEQ ID NO 11
<211> LENGTH: 32
<212> TYPE: PRT
<213> ORGANISM: Homo sapiens

<400> SEQUENCE: 11

```
Ser Pro Lys Met Val Gln Gly Ser Gly Cys Phe Gly Arg Lys Met Asp
  1               5                  10                  15

Arg Ile Ser Ser Ser Gly Leu Gly Cys Lys Val Leu Arg Arg His
             20                  25                  30
```

<210> SEQ ID NO 12
<211> LENGTH: 134
<212> TYPE: PRT
<213> ORGANISM: Homo sapiens

<400> SEQUENCE: 12

```
Met Asp Pro Gln Thr Ala Pro Ser Arg Ala Leu Leu Leu Leu Leu Phe
  1               5                  10                  15

Leu His Leu Ala Phe Leu Gly Gly Arg Ser His Pro Leu Gly Ser Pro
             20                  25                  30

Gly Ser Ala Ser Asp Leu Glu Thr Ser Gly Leu Gln Glu Gln Arg Asn
         35                  40                  45

His Leu Gln Gly Lys Leu Ser Glu Leu Gln Val Glu Gln Thr Ser Leu
     50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
            115                 120                 125

Lys Val Leu Arg Arg His
        130
```

<210> SEQ ID NO 13
<211> LENGTH: 151

<212> TYPE: PRT
<213> ORGANISM: Homo sapiens

<400> SEQUENCE: 13

```
Met Ser Ser Phe Ser Thr Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150
```

<210> SEQ ID NO 14
<211> LENGTH: 163
<212> TYPE: PRT
<213> ORGANISM: Homo sapiens

<400> SEQUENCE: 14

```
Met Ser Ser Phe Ser Thr Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr Arg Ile Thr Ala Arg Glu Asp Lys Gln
145                 150                 155                 160

Gly Trp Ala
```

<210> SEQ ID NO 15
<211> LENGTH: 492
<212> TYPE: DNA

```
<213> ORGANISM: Artificial Sequence
<220> FEATURE:
<223> OTHER INFORMATION: codon-optimized

<400> SEQUENCE: 15
atgagctcct tttccactac tactgtgtcc tttctgctgc tgctggcctt ccagctgctg       60
ggccaaaccc gggctaaccc aatgtacaac gccgtcagca atgctgatct gatggatttt     120
aagaatctgc tggatcacct ggaggaaaag atgcctctgg aagacgaagt ggtccctcct     180
caagtcctgt ccgaacctaa cgaggaagcc ggcgctgccc tgagccctct ccctgaagtc     240
ccaccctgga caggggaggt cagccccgca cagagggacg gaggggcact gggaagaggc     300
ccatgggata gctccgaccg gagcgctctg ctgaaaagca aactgagggc tctgctgacc     360
gcccctagaa gcctcaggag aagctcctgc ttcggcggaa ggatggaccg gattggggca     420
caaagcggcc tgggatgtaa ctccttccgg tataggatta cagctagaga agataaacag     480
ggctgggctt aa                                                         492
```